United States Patent
Helson et al.

(10) Patent No.: US 10,532,045 B2
(45) Date of Patent: *Jan. 14, 2020

(54) LIPOSOMAL MITIGATION OF DRUG-INDUCED INHIBITION OF THE CARDIAC $I_{Kr}$ CHANNEL

(71) Applicant: SignPath Pharma Inc., Quakertown, PA (US)

(72) Inventors: Lawrence Helson, Quakertown, PA (US); George M. Shopp, Boulder, CO (US); Annie Bouchard, Stoke (CA)

(73) Assignee: Signpath Pharma, Inc., Sandy, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/575,644

(22) Filed: Dec. 18, 2014

(65) Prior Publication Data

US 2015/0164878 A1 Jun. 18, 2015

Related U.S. Application Data

(60) Provisional application No. 61/917,426, filed on Dec. 18, 2013, provisional application No. 61/977,417, filed on Apr. 9, 2014.

(51) Int. Cl.
| | |
|---|---|
| *A61K 31/4545* | (2006.01) |
| *A61K 9/127* | (2006.01) |
| *A61K 31/506* | (2006.01) |
| *A61K 31/445* | (2006.01) |
| *A61K 31/12* | (2006.01) |

(52) U.S. Cl.
CPC .......... *A61K 31/4545* (2013.01); *A61K 9/127* (2013.01); *A61K 31/12* (2013.01); *A61K 31/445* (2013.01); *A61K 31/506* (2013.01)

(58) Field of Classification Search
None
See application file for complete search history.

(56) References Cited

U.S. PATENT DOCUMENTS

| | | | |
|---|---|---|---|
| 4,812,312 A | 3/1989 | Lopez-Berestein et al. | |
| 5,023,087 A | 6/1991 | Yao-Young | |
| 5,679,864 A | 10/1997 | Krackov et al. | |
| 6,143,276 A | 11/2000 | Unger | |
| 6,143,321 A | 11/2000 | Needham | |
| 6,787,132 B1 * | 9/2004 | Gabizon | A61K 9/1271 424/85.1 |
| 6,946,475 B1 | 9/2005 | Lloyd | |
| 7,060,733 B2 | 6/2006 | Pandol et al. | |
| 7,067,159 B2 | 6/2006 | Katz et al. | |
| 7,507,864 B2 | 3/2009 | Miller et al. | |
| 7,674,820 B2 | 3/2010 | Fedida et al. | |
| 7,723,515 B1 | 5/2010 | Dimauro | |
| 7,871,609 B2 | 1/2011 | Ziff et al. | |
| 7,968,115 B2 | 6/2011 | Kurzrock et al. | |
| 8,062,663 B2 | 11/2011 | Wang et al. | |
| 8,202,839 B1 | 1/2012 | Sung | |
| 8,153,172 B2 | 4/2012 | Antony | |
| 8,207,219 B2 | 6/2012 | Fedida et al. | |
| 8,642,074 B2 | 2/2014 | Mei et al. | |
| 8,747,890 B2 | 6/2014 | Nelson | |
| 8,753,674 B2 | 6/2014 | Nelson | |
| 9,138,411 B2 | 9/2015 | Ranjan et al. | |
| 9,682,041 B2 | 6/2017 | Helson | |
| 10,117,881 B2 | 11/2018 | Helson | |
| 10,238,602 B2 | 3/2019 | Helson | |
| 10,258,691 B2 | 4/2019 | Helson | |
| 10,349,884 B2 | 7/2019 | Helson | |
| 10,357,458 B2 | 7/2019 | Helson | |
| 2001/0051184 A1 | 12/2001 | Heng | |
| 2002/0048598 A1 | 4/2002 | Malik | |
| 2002/0110586 A1 | 8/2002 | Madden et al. | |
| 2005/0101674 A1 | 5/2005 | Maurer et al. | |
| 2005/0181036 A1 | 8/2005 | Aggarwal et al. | |
| 2005/0233970 A1 | 10/2005 | Garnick | |
| 2005/0266067 A1 | 12/2005 | Sengupta et al. | |

(Continued)

FOREIGN PATENT DOCUMENTS

| | | |
|---|---|---|
| CA | 2584279 A1 | 4/2005 |
| CN | 104758255 | 7/2015 |

(Continued)

OTHER PUBLICATIONS

Sun, M., et al., "Enhancement of transport of curcumin to brain in mice by poly(n-butylcyanoacrylate) nanoparticle," J. Nanopart Res., vol. 12, 2010, pp. 3111-3122.

Tonnesen, Hanne, H., et al, "Studies on curcumin and curcuminoids: XXV. Inhibition of primaquine-induced lysis of human red blood cells by curcumin," International Journal of Pharmaceutics 110 (1994) 161-167.

U.S. Department of Health and Human Services, "Guidance for Industry, S7B Nonclinical Evaluation of the Potential for Delayed Ventricular Repolarization (QT Interval Prolongation) by Human Pharmaceuticals," Oct. 2005, pp. 1-13.

(Continued)

*Primary Examiner* — Celeste A Roney
(74) *Attorney, Agent, or Firm* — Edwin S. Flores; Chalker Flores, LLP

(57) ABSTRACT

Compositions and methods are provided for preventing one or more cardiac channelopathies or conditions resulting from irregularities or alterations in cardiac patterns, or both, in a human or animal subject comprising: one or more pharmacologically active agents that causes at least one of $I_{Kr}$ channel inhibition or QT prolongation by inhibiting the activity of an ether-a-go-go-related gene (hERG); and one or more liposomes, wherein the liposomes are empty liposomes and administered prior to, concomitantly, or after administration of the pharmacologically active agent.

13 Claims, 17 Drawing Sheets

(56) References Cited

U.S. PATENT DOCUMENTS

| | | | |
|---|---|---|---|
| 2006/0067998 A1 | 3/2006 | Kurzrock et al. | |
| 2006/0147512 A1 | 7/2006 | Sabin | |
| 2006/0269595 A1 | 11/2006 | Madden | |
| 2007/0048284 A1 | 3/2007 | Donahue et al. | |
| 2008/0075671 A1 | 3/2008 | Dimauro | |
| 2008/0103213 A1* | 5/2008 | Kurzrock | A61K 9/1271 514/679 |
| 2008/0107749 A1 | 5/2008 | Maitra et al. | |
| 2008/0138400 A1 | 6/2008 | Kurzrock et al. | |
| 2008/0253961 A1 | 10/2008 | Braden et al. | |
| 2008/0255464 A1 | 10/2008 | Vincent | |
| 2009/0143433 A1 | 6/2009 | Hendrix | |
| 2009/0246770 A1 | 10/2009 | Levy | |
| 2009/0291134 A1 | 11/2009 | Ateeq et al. | |
| 2009/0317387 A1 | 12/2009 | Paton et al. | |
| 2009/0324703 A1 | 12/2009 | Frautschy et al. | |
| 2010/0004549 A1 | 1/2010 | Kohls et al. | |
| 2010/0048957 A1 | 2/2010 | Kim | |
| 2010/0068251 A1 | 3/2010 | Ali et al. | |
| 2010/0093873 A1 | 4/2010 | Goldfischer | |
| 2010/0120890 A1 | 5/2010 | Fedida | |
| 2010/0151000 A1 | 6/2010 | Thomas et al. | |
| 2010/0179103 A1 | 7/2010 | Desai | |
| 2010/0239552 A1 | 9/2010 | Mayoux et al. | |
| 2010/0240581 A1 | 9/2010 | Tortoriello et al. | |
| 2010/0291043 A1 | 11/2010 | Medin et al. | |
| 2011/0117186 A1 | 5/2011 | Helson | |
| 2011/0200665 A1 | 8/2011 | Mei et al. | |
| 2011/0229555 A1 | 9/2011 | Helson et al. | |
| 2011/0287085 A1 | 11/2011 | Kurzrock et al. | |
| 2012/0021036 A1 | 1/2012 | Majeti et al. | |
| 2012/0003177 A1 | 2/2012 | Burke et al. | |
| 2012/0040014 A1 | 2/2012 | Settineri et al. | |
| 2012/0058208 A1 | 3/2012 | Jacob | |
| 2012/0237590 A1 | 9/2012 | Helson | |
| 2012/0308643 A1* | 12/2012 | Helson | A61K 9/127 424/450 |
| 2013/0310351 A1 | 11/2013 | Milan et al. | |
| 2013/0337488 A1 | 12/2013 | Helson | |
| 2014/0050780 A1 | 2/2014 | Cerundolo et al. | |
| 2015/0343063 A1 | 12/2015 | Helson | |
| 2016/0193149 A1 | 7/2016 | Helson | |
| 2017/0035887 A1 | 2/2017 | Helson | |
| 2017/0095489 A1 | 4/2017 | Helson | |
| 2017/0246110 A1 | 8/2017 | Helson | |
| 2017/0312366 A1 | 11/2017 | Helson | |
| 2018/0055770 A1 | 3/2018 | Helson et al. | |

FOREIGN PATENT DOCUMENTS

| | | |
|---|---|---|
| DE | 10029770 A1 | 12/2001 |
| EP | 3144006 | 9/2017 |
| JP | 10279487 A | 10/1998 |
| JP | H10191927 A | 7/2010 |
| WO | 2000070949 A1 | 11/2000 |
| WO | 2001093683 A1 | 12/2001 |
| WO | 2002002582 A1 | 1/2002 |
| WO | 2004047717 A2 | 6/2004 |
| WO | 2004080396 A2 | 9/2004 |
| WO | 2006061101 A2 | 6/2006 |
| WO | 2006131737 A2 | 12/2006 |
| WO | 200706028 A2 | 5/2007 |
| WO | 2007103435 A2 | 9/2007 |
| WO | 2007129062 A1 | 11/2007 |
| WO | 2008045534 A1 | 4/2008 |
| WO | 2008063513 A2 | 5/2008 |
| WO | 2008128123 A1 | 10/2008 |
| WO | 2009051837 A2 | 4/2009 |
| WO | 2009073050 | 6/2009 |
| WO | 2010009186 A1 | 1/2010 |
| WO | 2010033692 A1 | 3/2010 |
| WO | 2010057332 A1 | 5/2010 |
| WO | 2011063178 A1 | 5/2011 |
| WO | 2011001351 A1 | 6/2011 |
| WO | 2011119588 A1 | 9/2011 |
| WO | 2012125830 A2 | 9/2012 |
| WO | 2012167212 A2 | 12/2012 |
| WO | 2013041894 | 3/2013 |
| WO | 2013166249 A1 | 11/2013 |
| WO | 2013188767 | 12/2013 |
| WO | 2013188767 A1 | 12/2013 |
| WO | 2015095576 A1 | 6/2015 |

OTHER PUBLICATIONS

Verma, Richa, et al., "Structural and functional changes in a syntheitic S5 segment of KvLQT1 channel as a result of a conserved amino acid substitution that occurs in LQT1 syndrome of human," Biochimica et Biophysica Acta, 1798, Jan. 2010, pp. 461-470.

Vidal, Alessandra Teixeira, et al., "Prolonged cardioprotective effect of pyridostigmine encapsulated in liposomes," Life Sciences, vol. 86, 2010, pp. 17-23.

Wang, Timothy C., et al., "Pancreatic Gastrin Stimulates Islet Differentiation of Transforming Growth Factor a-Induced Ductular Precursor Cells," The Journal of Clinical Investigation, Inc., Sep. 1993, vol. 92, pp. 1349-1356.

Wesley, Umadevi V., et al., "Role for Dipeptidyl Peptidase IV in Tumor Suppression of Human Non Small Cell Lung Carcinoma Cells," Int. J. Cancer, (2004), 109:855-866.

Wesley, Umadevi V., et al., "Dipeptidyl Peptidase Inhibits Maignant Phenotype of Prostate Cancer Cells by Blocking Basic Fibroblast Growth Factor Signaling Pathway," Cancer Res. (2005), a65:1325-1334.

Wu, Aiguo, et al., "Brain and Spinal Cord Interaction: A Dietary Curcumin Derivative Counteracts Locomotor and Cognitive Deficits After Brain Trauma," Neurohabil Neural Repair, May 2011, 25(4):332-342.

Xu, Ying, et al., "Curcumin Reverses Impaired Hippocampal Neurogenesis and Increases Serotonin Receptor 1A mRNA and Brain-Derived Neurotrophic Factor Expression in Chronically Stressed Rats," Brain Research, (2007), 1162, pp. 9-18.

Zhang, et al., Self-Assembled Lipd—Polymer Hybrid Nanoparticles; A Robust Drug Delivery Platform.

FDA Pharmacology Review of Xalkori (crizotinib), IND No. 202570, 2011a, www.accessdata.fda.gov/drugsatfda_docs/nda/2011/202570Orig1s000PharmR.pdf (accessed Oct. 9, 2013).

FDA Pharmacology of Tasigna® (nilotinib), IND No. 22-068, 2007a, www.accessdata.fda.gov/drugsatfda_docs/nda/2007/022068s000_PharmR_P1.pdf and www.accessdata.fda.gov/drugsatfda_docs/nda/2007/022068s000_MedR_P2.pdf, (accessed Oct. 25, 2013).

Helson, et al., "Liposome mitigation of curcumin inhibition of cardiac potassium delayed-rectifier current," Journal of Receptor, Ligand and Channel Research, Nov. 15, 2012, vol. 5, pp. 108.

Konwarh, R., et al., "Poly(ethylene glycol)-magnetic nanoparticles-curcumin trio: Directed morphogenesis and synergistic free-radical scavenging," Colloids and Surfaces B: Biointerfaces, vol. 81, Aug. 7, 2010, pp. 578-586.

Layton, D, et al., "Prolongation of the QT interval and cardiac arrhythmias associated with cisapride: limitations of the pharmacoepidemiological studies conducted and proposals for the future," Pharmacoepidemiol Drug Saf., 12(1), Nov. 13, 2002, pp. 31-40.

Lee, et al., "Electrophysiological Effects of the Anti-Cancer Drug Lapatinib on Cardiac Repolarization," Basic & Clinical Pharmacology & Toxicology, vol. 107, Dec. 21, 2009, pp. 614-618.

Mehta, RT, et al., "Formulation, toxicity, and antifungal activity in vitro of liposomal-encapsulated nystatin as therapeutic agent for systemic candidiasis," Antimicrob Agents Chemother., 31(12), Dec. 1987, pp. 1897-1900.

Moha, H, et al., "Curcumin blocks the recombinant human cardiac KCNQ 1/KCNE 1 channels (IKs) stably expressed in HEK 293 cells," Abstract of 12th Annual Meeting of the French Society of Pharmacology and Therapeutics, Fund. & Clin. Pharma., vol. 22:1, Jun. 2008.

Mosse, et al., "Safety and activity of crizotinib for pediatric patients with refractory solid tumours of anaplastic large-cell lymphoma: a Children's Oncology Group phase 1 consortium study," Lancet Oncol., May 2013, vol. 14(6), pp. 472-480.

(56) References Cited

OTHER PUBLICATIONS

Naseem, et al., "Bupivacaine Extended Release Lipsome Injection Does not Prolong Qtc Interval in a Thorough QT/QTc Study in Healthy Volunteers," Journal of Clin. Pharma., 2012, vol. 52, pp. 1441-1447.
Segman, RH., et al., "Peripheral Blood Mononuclear Cell Gene Expression Profiles Identify Emergent Post-Traumatic Stress Disorder Among Trauma Survivors," Molecular Psychiatry, (2005), vol. 10, pp. 500-513.
Shah, et al., "Cardiovascular Safety of Tyrosine Kinase Inhibitors: With a Special Focus on Cardiac Repolarisation (QT Interval)," Drug Saf., Apr. 26, 2013, vol. 36, pp. 295-316.
Shimizu, Wataru, et al., "Sodium Channel Block with Mexiletine is Effective in Reducing Dispersion of Repolarization and Preventing Torsade de Pointes in LQT2 and LQT3 Models of the Long-QT Syndrome," vol. 96, Apr. 28, 1997, pp. 2038-2047.
Tasigna Package insert, Novartis Pharmaceuticals, Revised Sep. 2013.
Van De Water, et al., "An Improved Method to Correct the QT Interval of the Electrocardiogram for Changes in Heart Rate," Journal of Pharmacological Methods, Apr. 1989, vol. 22, pp. 207-217.
Witchel, "Drug-induced hERG Block and Long QT Syndrome," Cardiovascular Therapeutics, 2011, vol. 29, pp. 251-259.
Xalkori Package insert, Pfizer Laboratories, revised Feb. 2013, 10 pp.
Yap, Y. G., et al., "Drug Induced QT Prolongation and Torsades de Pointes," Heart, vol. 89, Nov. 2003, pp. 1363-1372.
Zachariae, U., et al., "Side chain flexabilities in the human ether-a-go-go related potassium channel (hERG) together with matched-pair binding studies suggest a new binding mode for channel blockers," J. Med. Chem., vol. 52 (14),Jan. 2, 2009, pp. 4266-4276.
Zhou, L., et al., "Nilotinib for Imatinib-Resistant or -Intolerant Chronic Myeloid Leukemia in Chronic Phase, Accelerated Phase, or Blast Crisis: A Single- and Multiple-Dose, Open-Label Pharmacokinetic Study in Chinese Patients," Clinical Therapeutics, vol. 31:7, Jul. 2009, pp. 1568-1575.
Zhou, et al., "Correction of Defectrive Protein Trafficking of a Mutant HERG Potassium Channel in Human Long QT Syndrome," The Journal of Biological Chemistry, vol. 274:44, Oct. 29, 1999, pp. 31123-31126.
Kessler, Ronald C., et al., "Posttraumatic Stress Disorder in the national Comorbidity Survey," Archives of General Psychiatry, vol. 52, No. 12, pp. 1049-1060.
Kim, So Jung, et al., "Curumin Stimulates Proliferation of Embryonic Neural Progenitor Cells and Neurogenesis in the Adult Hippocampus," The Journal of Biological Chemistry, May 23, 2008, vol. 283, No. 21, pp. 14497-14505.
Koehler, Jacqueline A., et al., "Glucagon-Like Peptide-1 Receptor Activation Modulates Pancreatitis-Associated Gene Expression Bud Does Not Modify the Susceptibility to Experimental Pancreatitis in Mice," Diabetes, Sep. 2009, vol. 58, pp. 2148-2161.
Kourelis, Taxiarchis V., et al., "Metformin and Cancer: New Applications for an Old Drug," Med. Oncol., Feb. 8, 2011, 14 pages.
Extended and Supplemental European Search Report for EPO 11760055.1 dated Jun. 13, 2014, 7 pages.
Extended European Search Report and Europeean Search Opinion for EPO 12757689.0 dated Oct. 22, 2014, 7 pages.
Extended European Search Report and European Search Opinion for 12792560.0 dated Oct. 30, 2014, 11 pages.
International Search Report and Written Opinion for PCT/US2011/029393, dated Jun. 23, 2011, 17 pages.
International Search Report and Written Opinion for PCT/US2013/057744 dated Dec. 12, 2013, 14 pages.
Anderson, Corey, et al., "Most LQT2 Mutations Reduce Kv11.1 (hERG) Current by a Class 2 (Trafficking-Deficient) Mechanism," Circuilation, Nov. 11, 2005, pp. 365-373.
International Search Report and Written Opinion for PCT/US2014/071246, dated Mar. 27, 2015, 14 pages.
Rajamani, S., et al., "Drug-induced long QT syndrome: hERG K+ channel block and disruption of protein trafficking by fluoxetine and norfluoxetine," British Journal of Pharmacology, Sep. 11, 2006, vol. 149, pp. 481-489.
Ranjan, A. P., et al, "Efficacy of Liposomal Curcumin in a Human Pancreatic Tumor Xenograft Model: Inhibition of Tumor Growth and Angiogenesis," Anticancer Research, vol.. 33, Jul. 26, 2013, pp. 3603-3610.
Ravindran, J., et al., "Curcumin and Cancer Cells: How Many Ways Can Curry Kill Tumor Cells Selectively?," The AAPS Journal, vol. 11, No. 3, Jul. 10, 2009, pp. 495-510.
Yang, Ping, et al., "Allelic Variants in Long-QT Disease Genese in Patients with Drug-Associated Rosades de Pointes," Circulation, Apr. 23, 2002, pp. 1943-1948.
Begum, A.N., et al., "Curcumin Structure-Function, Bioavailibility, and Efficacy in Models of Neuroinflammation and Alzheimer's Disease," The Journal of Pharmacoloby and Experimental Therapeutics, vol. 326:1, Apr. 15, 2008, pp. 196-208.
Grama, C.N., et al., "Poly(lactide--glycolide) nanoparticles for peroral delivery of bioactives," Current Opinion in Colloid and Interface Science, London, GB, vol. 16, No. 3, Nov. 24, 2010, pp. 238-245.
Harish, G., et al., "Bioconjugates of curcumin display improved protection against glutathione depletion mediated oxidative stress in a dopaminergic neuronal cell line: Implications for Parkinson's disease," Bioorgaic & Medicinal Chemistry, vol. 18, Feb. 20, 2010, pp. 2631-2638.
Kim, K-P., et al., "Nilotinib in Patients with GIST who failed imatinib and sunitinib: importance of prior surgery on drug bioavailability," Jul. 12, 2010, Cancer Chemother. Pharmacol., vol. 68, pp. 285-291.
Kowluru, Renu A., et al., "Effects of Curcumin on Retinal Oxidative Stress and Inflammation in Diabetes," Nutrition & Metabolism, Apr. 16, 2007, 8 pages.
Kulkarni, S.K., et al., "An Overview of Curcumin in Neurological Disorders," Indian J. Pharm. Sci, Jul. 1, 2010, 72:2, pp. 149-154.
Kumar, T. Peeyush, et al., "Curcumin Modulates Dopaminergic Receptor, CREB and Phospholipase C Gene Expression in the Cerebral Cortex and Cerebellum of Streptozotocin Induced Diabetic Rats," Journal of Biomedical Science, (2010), 2:43, 11 pages.
Lamont, Benjamin J., et al., "Differential Antidiabetic Efficacy of Incretin Agonists Versus DPP-4 Inhibition in High Fat-Fed Mice," Diabetes, Jan. 2008, vol. 57, pp. 190-198.
Leung, et al., "Effective stablization of curcumin by association to plasma proteins: human serum albumin and fibronogen," Langmuir, 2009, vol. 25, Issue 10, pp. 5773-5777.
Li, Yu-Cheng, et al., "Antidepressant-Like Effects of Curcumin on Serotonergic Receptor-Coupled Ac-cAMP Pathway in Chronic Unpredictable Mild Stress of Rats," Progress in Neuro-Psychophamacoloby & Biological Psychiatry, (2009), vol. 33, pp. 435-449.
Li, Lan, et al., "Liposome-Encapsulated Curcumin In Vitro and In Vivo Effects on Proliferation, Apoptosis, Signaling, and Angiogenesis," Cancer, May 4, 2005, 104:1322-1331.
Lim, Kah Jing, et al., "A Polymeric Nanoparticle Formulation of Curcumin Inhibits Growth, Clonogenicity and Stem-Like Fraction in Malignant Brain Tumors," Cancer Biology & Therapy, Mar. 1, 2011, 11:5, pp. 464-473.
Logan-Smith, Melanie J., et al., "Curcumin, a Molecule that Inhibits the Ca2+-ATPase of Sarcoplasmic Reticulum but Increases the Rate of Accumulation of Ca2+," The Journal of Biological Chemistry, (2001), vol. 276, No. 50, pp. 46905-46911.
Mach, Claire M., et al., "Determination of Minimum Effective Dose and Optimal Dosing Schedule for Liposomal Curcumin in a Xenograft Human Pancreatic Cancer Model," (2009), Anticancer Research, 29:1895-1900.
Maciel, NR, et al., "Reduced Cardiovascular Alterations of Tarter Emetic Administered in Long-Circulating Liposomes in Rats," Toxicology Letters, 2010; 199(3):234-238.
Marino, Silvia, et al., "Sertaline in the Treatment of Depressive Disorders in Patients with Parkinson's Disease," Neurological Sciences, Nov. 2008, 29:391-395.
Matsushita, Yuichi, et al., "Activation of Peroxisome Proliferator-Activated Receptor d Inhibits Streptozotocin-Induced Diabetic

(56) References Cited

OTHER PUBLICATIONS

Nephropathy Through Anti-Inflammatory Mechanisms in Mice," Diabetes, Mar. 2011, vol. 60, pp. 960-968.
Mayer, Lawrence D., et al., "Intravenous Pretreatment with Empty pH Liposomes Alters the Pharmacokinetics and Toxicity of Doxorubicin through In Vivo Active Drug Encapsulation," Journal of Pharmaceutical Sciences, vol. 88, No. 1, Nov. 25, 1998, pp. 96-102.
Mishra, S., et al., "The effect of curcumin (turmeric) on Alzheimer's disease: An overview," Annals of Indian Academy of Neurology, vol. 11:1, 2008, pp. 13-19.
Mukerjee, Anindita, et al., "Formulation, Characterization and Evaluation of Curcumin-Loaded PLGA Nanospheres for Cancer Therapy," (2009), Anticancer Research 29:3867-3876.
Murphy, Eric, A., et al., "Targeted Nanogels: A Versatile Platform for Drug Delivery to Tumors," Molecular Cancer Therapeutics, Apr. 25, 2011; 10:972-982.
Nam, et al., "Curcumin-Loaded PLGA Nanoparticles Coating onto Metal Stent by Electrophoretic Deposition Techniques," Bull. Korean Chem. Soc., Jan. 2007, vol. 28, No. 3, pp. 397-402.
Narala, Venkata R., et al., "Curcumin is not a Ligand for Peroxisome Proliferator-Activated Receptor-Y," Gene Therm. Mol. Biol., Apr. 1, 2009, 13(1):20-25.
Nousiainen, T., et al., "QT dispersion and late potentials during doxorubicin therapy for non-Hodgkin's lymphoma," Journal of Internal Medicine, 245, 1999, pp. 359-364.
Olansky, Leann, "Do Incretin-Based Therapies Cause Acute Pancreatitis?" Journal of Diabetes Science and Technology, Jan. 2010, vol. 4, Issue 1, pp. 228-229.
Pitman, Roger K., et al., "Conceptually Driven Pharmacologic Approaches to Acute Trauma," CNS Spectrums, Feb. 2005, vol. 10, No. 2, pp. 99-106.
Quan, Xiao-Qing, et al., "Increasing Gap Junction Coupling Reduces Transmural Dispersion of Repolarization and Prevents Torsade de Pointes in Rabbit LQT3 Model," J. Cardiovasc. Electrophysiol., vol. 18, Nov. 2007, pp. 1184-1189.
Rajeswari, A., et al., "Inhibition of monoamine oxidase-B by the polyphenolic compound, curcumin and its metabolite tetrahydrocurcumin, in a model of Parkinson's disease induced by MPTP neurodegeneration in mice," Inflammopharmacology, vol. 16, 2008, pp. 96-99.
Roberts, A.N., et al., "Molecular and Functional Characterization of Amylin, a Peptide Associated with Type 2 Diabetes Mellitus," Proc. Natl. Acad. Sci. USA, Dec. 1989, vol. 86, pp. 9662-9666.
Rosi, S., et al., "Chemokine Receptor 5 Antagonist d-Ala-Peptide T-Amide Reduces Microglia and Astrocyte Activation Within the Hippocampus in a Neuroinflammatory Rat Model of Alzheimer's Disease," Neuroscience, (2005), vol. 134, pp. 671-676.
Rui, Pan, et al., "Curcumin Improves Learning and Memory Ability and its Neuroprotective Mechanism in Mice," Chin. Med. J., (2008), vol. 121, No. 9, pp. 832-839.
Rusinek, Henry, et al., "Hippocampal Blood Flow in Normal Aging Measured with Arterial Spin Lavelin at 3T," Magnetic Resonance in Medicine, (2011), 65:128-137.
Schena, Francesco P., et al., "Pathogenetic Mechanisms of Diabetic Nephropathy," J. Am. Soc. Nephrol., (2005), 16: S30-S33.
Segman, RH., et al., "Association Between the Dopamine Transporter Gene and Posttraumatic Stress Disorder," Molecular Psychiatry, (2002), vol. 7, pp. 903-907.
Shaikh, J., et al, "Nanoparticle encapsulation improves oral bioavailability of curcumin by at least 9-fold when compared to curcumin administered with piperine as absorption enhancer," European Journal of Pharmaceutical Sciences, Elsevier, Amsterdam, NL, vol. 37, No. 3-4, Jun. 28, 2009, pp. 223-230.
Shimizu, Wataru, et al. "Effects of a K+ Channel Opener to Reduce Transmural Dispersion of Repolarization and Prevent Torsade de Pointes in LQT1, LQT2, and LQT3 Models of the Long-QT Syndrome," Circulation, 2000, 102:706-712.
Singh, Sonal, et al., "Long-Term Risk of Cardovascular Events with Rosiglitazone," JAMA, Sep. 12, 2007, vol. 298, No. 10, pp. 1189-1195.

Smith, Judith A., et al., "Abstract A29: Development of Liiposomal Curcumin as a New Potential Anticancer Agent," Molecular Cancer Therapeutics, Dec. 2009, vol. 8, Issue 12, Supplement 1, 1 page.
Stansfeld, Phillip, J., et al., "Drug Block of the hERG Potassium Channel: Insight From Modeling," Proteins: Structure, Function and Bioinformatics, Apr. 19, 2007, 68:568-580.
Stein, Murray B., et al., "Genetic and Environmental Influences on Trauma Exposure and Posttraumatic Stress Disorder Symptoms: A Twin Study," Am. J. Psychiatry, Oct. 2002, vol. 159, No. 10, pp. 1675-1681.
Crouch, et al., "Clinical Relevance and Management of Drug-Related QT Interval Prolongation," Pharmacotherapy, Nov. 7, 2003, vol. 23:7, pp. 881-908.
Doherty, K., et al., "Multi-parameter in vitro toxicity testing of crizotinib, sunitinib, erlotinib, and nilotinib in human cardiomyocytes," Toxicoloty and Applied Pharmacology, Apr. 28, 2003, vol. 272, pp. 245-255.
Extended European Search Report and Europeean Search Opinion for EPO 10832224.9 dated Feb. 26, 2013.
International Search Report and Written Opinion for PCT/US2010/057332, dated Aug. 2, 2011, 12 pages.
International Search Report and Written Opinion for PCT/US2012/029230, dated Sep. 21, 2012, 14 pages.
International Search Report and Written Opinion for PCT/US2012/040637, dated Dec. 12, 2012, 13 pages.
Abel, Ted., et al., "Epigenetic Targets of HDAC Inhibition in Neurodegenerative and Psychiatric Disorders," Current Opinion in Pharmacology, (2008), vol. 8, pp. 57-64.
Aggarwal, et al., "The Molecular Targets and Therapeutic Uses of Curcumin in Health and Disease," (2006), Springer, 515 pages.
Anderson, P., et al., "The Hippocampus Book," Oxford University Press, 2006, 102 pages.
Arbiser, Jack L., et al., "Curcumin is an In Vivo Inhibitor of Angiogenesis," Moledular Medicine, (1998), 4:376-383.
Ataie, Amin, et al., "Neuroprotective Effects of the Polyphenolic Antioxidant Agnet, Curcumin, Against Homocysteine-Induced Cognitive Impairment and Oxidative Stress in the Rat," Pharmacology, Biochemistry and Behavior, (2010), vol. 96, pp. 378-385.
Bala, Kiran, et al., "Neuroprotective and Anti-Aging Effects of Curcumin in Aged Rat Brain Regions," Biogerontology, (2006), vol. 7, pp. 81-89.
Bentzen, Peter J., et al., "Curcumin Induced Suicidal Erythrocyte Death," Cellular Physiology and Biochemistry, (2007), 19:153-164.
Bisht, Savita, et al., "Polymeric Nanoparticle-Encapsulated Curcumin ("Nanocurcumin"): A Novel Strategy for Human Cancer Therapy," Journal of Nanobiotechnology, (2007), 18 pages.
Bisht, Savita, et al., "Systemic Administration of Polymeric Nanoparticle-Encapsulated Curcumin (NanoCurcTM) Blocks Tumor Growth and Metastases in Preclinical Models of Pancreatic Cancer," Mol. Cancer Ther., (Aug. 2010), 9(8):2255-2264.
Blomgren, Kerstin, et al., "Obesity and Treatment of Diabetes with Glyburide may Both be Risk Factors for Acute Pancreatitis," Diabetes Care, (2002), 25:298-302.
Brownlee, Michael, "Biochemistry and Molecular Cell Biology of Diabetic Complications," Nature, Dec. 13, 2001, vol. 414, pp. 813-820.
Chao, Chun C., et al., "Glia: The Not So Innocent Bystanders," Journal of NeuroVirology, (1996), 2:234-239.
Chen, Shali, et al., "High glucose-induced, endothelin-dependent fibronectin synthesis is mediated via NF-kB and AP-1," Am J. Physiol. Cell Physiol., Sep. 18, 2002, 284:C263-C272.
Chen, et al., "An in vitro study of liposomal curcumin: stability, toxicity and biological activity in human lymphocytes and epstein-barr virus-transformed human B-cells," International Journal of Pharmaceutics, Jan. 2009, vol. 366, Issue 1-2, pp. 133-139.
Chiu, Jane, et al., "Curcumin Prevents Diabetes-Associated Abnormalities in the Kidneys by Inhibiting p300 and Nuclear Factor-kB," Nutrition, (2009), 25:964-972.
Compton, SJ, et al., "Genetically Defined Therapy of Inherited Long-QT Syndrome. Correction of Abnormal Repolarization by Potassium," Circulation, 1996; 94:1018-1022.
Crack, Peter J., et al., "Glutathione Peroxidase-1 Contributes to the Neuroprotection Seen in the Superoxide Dismutase-1 Transgenic

(56) References Cited

OTHER PUBLICATIONS

Mouse in Response to Ischemia/Reperfusion Injury," Journal of Cerebral Blood Flow and Metabolism, (2003), vol. 23, No. 1, pp. 19-22.
D'Amico, Michele, et al., "Long-Term Inhibition of Dipeptidyl Peptidase-4 in Alzheimer's Prone Mice," Experimental Gerontology 45,3, (2010), 24 pages.
Djeddi, D, et al., "A: Effect of Domperidone on QT Interval in Neonates," J Pediatrics, 2008; 153(5):596-598.
Ducroq, J, et al., "Printemps R, Le Grand M.: Additive Effects Ziprasidone and D,L-Sotalol on the Action Potential in Rabbit Purkinje Fibers and on the hERG Potassium Current," J.Pharmacol. Toxicol Methods, 2005; 52:115-122.
Etheridge, SP, et al., "A New Oral Therapy for Long QT Syndrome: Long Term Oral Potassium Improves Repolarization in Patients with hERG Mutations," J AM Coll Cardiol, 2003; 42:1777-1782.
Everett, Peter C., et al., "Preclinical Assessment of Curcumin as a Potential Therapy for B-CLL," American Journal of Hematology, (2006), 8 pages.
Fahn, Stanlex, "Medical Treatment of Parkinson's Disease," Journal of Neurology, 1998, 245 (Supplement 3): p. 15-p. 24.
Fauchier, L, et al.,"JP: Effect of Verapamil on QT Interval Dynamicity," AM J Cardiol., 1999; 83(5):807-808 A10-1.
Fowler, NO, et al., "Electrocardiographic Changes and Cardiac Arrhythmias in Patients Receiving Psychotropic Drugs," Am J Cardiol, 1976; 37(2):223-230.
Garcia-Alloza, M., et al., "Curcumin Labels Amyloid Pathology In Vivo, Disrupts Existing Plaques, and Partially Restroes distorterneurites in an Alzheimer Mouse Model," Journal of Neurochemistry, (2007), vol. 102, pp. 1095-1104.
Gukovsky, Ilya, et al., "Curcumin Ameliorates Ethanol and Nonethanol Experimental Pancreatitis," Am. J. Physiol. Gastrointest. Liver Physiol., (2003), 284:G85-G95.
Helson, et al., "Infusion pharmacokinetics of lipocure (liposomal curcumin) and its metabolite tetrahydrocurcumin in beagle dogs," Anticancer Research, Oct. 2012, vol. 32, No. 10, pp. 4365-4370.
Hernandez-Fonseca, Juan P., et al., "Structural and Ultrastructural Analysis of Cerebral Cortex, Cerebellum, and Hypothalamus from Diabetic Rats," Experimental Diabetes Research Oct. 1, 2009: 2009: 329632.
Ireson, Christopher, et al., "Characterization of Metabolites of the Chemopreventive Agent Curcumin in Human and Rat Hepatocytes and in the Rat in Vivo, and Evaluation of Their Ability to Inhibit Phorbol Ester-induced Prostaglandin E2 Production," Cancer Research 61:1058-1064, 2001, pp. 1059-1062.
Jacob, Asha, et al., "Mechanism of the Anti-Inflammatory Effect of Curcumin: PPAR-γ Activation," Hindawi Publishing Corporation, PPAR Research, (2007), Article ID 89369, 5 pages
Jervell, A, et al., "Congenital Deaf-Mutism, Functional Heart Disease with Prolongation of the QT Interval and Sudden Death," Am Heart J., 1957; 54(1):59-68.
Kang, J, et al., "Discovery of a Small Molecule Activator of the Human Ether-a-go-go —Related Gene(HERG) Cardiac K+ Channel," Mol Pharmacol, 2005(3); 67:827-836.
Katchman, AN, et al., "Comparative Evaluation of Herg Currents and QT Intervals Following Challenge with Suspected Torsadogenic and Nontorsdogenic Drugs," J Pharmacol Exp Ther., 2006; 316(3):1098-1106.
International Search Report and Written Opinion for PCT/US2015/034078, dated Aug. 31, 2015, 17 pp.
Wang, Jingxiong, et al., "Phospholipid metabolite 1-palmitoyl-lysophosphatidylcholine enhances human ether-a-go-go-related gene (HERG) K+ channel function", Circulation, 2001, vol. 104, No. 22, pp. 2645-2648.
Rodrigues, C., et al., "Derivative Spectrophotmetry as a Tool for the Determination of Drug Partition Coefficients in water/dimyristoyl-L-α-phosphatidylglycerol (DMPG) Liposomes," Biophysical Chemistry (2001); 94:97-106.
Van Dijck, P.W.M., et al., "Influence of $Ca^{2+}$ and $Mg^{2+}$ on the thermotropic behaviour and permeability properties of liposomes prepared from dimyristoyl phosphatidylglycerol and mixtures of dimyristoyl phosphatidylglycerol and limyristoyl phosphatidylcholine," Biochimica et Biophysica Acta (1975); 406:465-478.
Chartrand, et al., "Potential role of the membrane in hERG channel functioning and drug-induced long QT syndrome," Biochimica et Biophysica Acta, May 25, 2010, vol. 1798, pp. 1651-1662.
Chayanupatkul, "Cirrhotic cardiomyopathy: review of pathophysiology and treatment." Hepatol Int., Jul. 2014, vol. 8, No. 3, pp. 308-315.
Dhandapani, K. M., et al., "Curcumin suppresses growth and chemoresistance of human glioblastoma cells via AP-1 and NFkB transcription factors," J. Neurochem (2007) 102:522-538.
Dhule, S.S., et al., "The Combined Effect of Encapsulating Curcumin and C6 Ceramide in Liposomal Nanoparticles against Osteosarcoma," Molecular Pharmaceutics, vol. 11, No. 2, Dec. 31, 2013, pp. 417-427.
Extended European Search Report and European Search Opinion for 14864686.2 dated May 4, 2017, 8 pages.
Extended European Search Report and European Search Opinion for 16188460.6 dated Nov. 16, 2016, 12 pages.
Gilenya (Fingolimod) Full Prescribing Information, Novartis: T2016-22, Feb. 2016, 25 pp.
Gou, M., et al., "Curcumin-loaded biodegradable polymeric micelles for colon cancer therapy in vitro and in vivo," Nanoscale, vol. 3, No. 4, Oct. 2010, pp. 1558-1567.
International Search Report and Written Opinion for PCT/US2013/045898, dated Sep. 6, 2013, 12 pages.
Leung, et al., "Effective stablization of curcumin by association to plasma proteins: human serum albumin and fibronogen," Langmuir, Mar. 25, 2009, vol. 25, Issue 10, pp. 5773-5777.
National Biodiversity Authority, Secretary of Government of India, Third Party Observation for Application No. EP20110760055, submitted for observation on Jul. 20, 2017, 7 pp.
Pisarik, et al., "Reduction of free amphothericin B Acute Toxicity in Mice after intravenous administration of empty liposomes," Journal of Infectious Diseases, May 1990, 161(5), pp. 1042-1044.
Ramachandran, C., et al., "Potentiation of Etoposide and Temozolomide Cytotoxicity by Curcumin and Turmeric Force in Brain Tumer Cell Lines," Journal of Complementary and Integrative Medicine (2012), 9(1):Article 20.
Ranjan, A.P., et al., "Efficacy of Liposomal Curcumin in a Human Pancreatic Tumor Xenograft Model: Inhibition of Tumor Growth and Angiogensis," Anticancer Research, vol. 33, No. 9, Jul. 26, 2013, pp. 3603-3609.
Ravindran, J., et al., "Curcumin and Cancer Cells: How Many Ways Can Cunly Kill Tumor Cells Selectively?," The MPS Journal, vol. 11:3, Sep. 2009, pp. 495-510.
Tudor, B-A, et al., "Amphotericin B® treatment causes QT prolongation in lung transplant-pateints," Intensive Care Medicine Experimental, Oct. 2015, 3(Suppl 1):A213 poster presentation.
Vincenzi, Frank F., et al., "Citalopram-Induced Long QT Syndrome and the Mammalian Dive Reflex," Drug Saf—Case Rep, vol. 2:12, Aug. 1, 2015, 5 pp.
WHO Model List of Essential Medicines, World Health Organization, Oct. 2013. pp. 1-47.
Wong-Beringer, Annie, et al., "Lipid Formulations of Amphotericin B: Clinical Efficacy and Toxicities," Clinical Infectious Diseases, May 4, 1998, vol. 27, pp. 603-618.
Yagi, Y., et al., "Analysis of Onset Mechanisms of a Sphingosine 1-Phosphate Receptor Modulator Fingolimod-Induced Atrioventricular Conduction Block and QT-Interval Prolongation," Toxicology and Applied Pharmacology, Sep. 16, 2014, 281, pp. 39-47.
Zeltser et al., "Drug-induced atrioventricular block: prognosis after discontinuation of the culprit drug." Journal of the American College of Cardiology, Jul. 2004, vol. 44, No. 1, pp. 105-108.
International Search Report and Written Opinion for PCT/US2017/057446, dated Dec. 29, 2017, 13 pp.
Rawal, et al., "Paclitaxel Induced Acute ST Elevation Myocardial Infarction: A Rare Case Report," Journal of Clinical and Diagnostic Research, Oct. 2016, vol. 10(10), pp. XD01-XD02.
Shopp, G.M., et al., "Liposomes ameliorate Crizotinib- and Nilotinib-induced inhibition of the cardiac IKr channel and Qtc prolongation," Anticancer Research, 2014, vol. 34, pp. 4733-4740.

(56) References Cited

OTHER PUBLICATIONS

International Search Report and Written Opinion of Korean Intellectual Property Office for PCT/US2017/060936 dated Feb. 20, 2018, 13 pp.
Tang, H., et al., "Curcumin Polymers as Anticancer Conjugates," Biomaterials, vol. 31, No. 27, Jun. 29, 2010, pp. 7139-7149.
Chinthalapally, et al., "Inhibition by dietary curcumin of azoxymethane-induced ornithine decarboxylase, tyrosine protein kinase, arachidonic acid metabolism and aberrant crypt foci formation in the rat colon," Carcinogensis, vol. 14, Iss. 11, Nov. 1, 1993, pp. 2219-2225.
Hasima, N., et al., "Cancer-linked targets modulated by curcumin," Int. J. Biochem. Mol. Bio., Dec. 30, 2012, vol. 3(4), pp. 328-351.
Hong, et al., "Curcumin inhibits tyrosine kinase activity of p195neu an also depletes p185neu," Clinical Cancer Research, Mar. 22, 1999, 5(7), pp. 1884-1891.
Webster, G., et al., "Contemporary reviews in cardiovascular medicine, An Update on Channelopathies," Jan. 2013, vol. 127, pp. 126-140.
WIKIPEDIA2, https://en.wikipedia.org/wiki/Atrioventricular_block (downloaded on Jul. 26, 2018).
Gilhotra, N. et al., "GABAergic and nitriergic modulation by curcumin for its antianxiety-like activity in mice," Brain Research 1352 (2010), pp. 167-175.
Xu, Ying, et al., "Curcumin Reverses Impaired Cognition and neuronal plasticity induced by chronic stress," Neuropharmacology, 57.4 (2009), pp. 463-471.

\* cited by examiner

LIPOSOMAL MITIGATION OF DRUG-INDUCED INHIBITION OF THE CARDIAC $I_{Kr}$ CHANNEL

CROSS-REFERENCE TO RELATED APPLICATIONS

This application claims priority to U.S. Provisional Application Ser. No. 61/917,426, filed Dec. 18, 2013, and U.S. Provisional Application Ser. No. 61/977,417, filed Apr. 9, 2014, and is a continuation-in-part application of U.S. patent application Ser. No. 14/268,376 filed May 2, 2014, which is a continuation patent application of U.S. patent application Ser. No. 13/487,233, filed Jun. 3, 2012, now U.S. Pat. No. 8,753,674 issued on Jun. 17,2014, which is a non-provisional application of U.S. Provisional Application Ser. No. 61/493,257 filed Jun. 3, 2011, the entire contents of each are incorporated herein by reference.

TECHNICAL FIELD OF THE INVENTION

The present invention relates in general to pharmacology and cardiology, and more particularly to liposomal based compositions and methods to therapeutically alter a genetic, drug-induced inhibition of the cardiac $I_{Kr}$ channel.

STATEMENT OF FEDERALLY FUNDED RESEARCH

None.

REFERENCE TO A SEQUENCE LISTING

None.

BACKGROUND OF THE INVENTION

Without limiting the scope of the invention, its background is described in connection with compositions and methods for controlling the duration of repolarization of the cardiac ventricle QT in a subject comprising administering to subject in need thereof of a modification of or functional interference with a therapeutic agent, or congenital defect, which if unmodified, can induce prolongation of repolarization in the heart myocyte action potential, torsade de points, and the long QT syndrome. The present invention comprises of either binding a QT prolonging drug with a liposome prior to parenteral (intravenous or subcutaneous) administration, or administration of an empty liposome prior to or concomitantly with therapeutic agents known to have a high risk of QT prolongation, or immediately following an envenomation.

The beating of the heart is due to precisely controlled regularly spaced waves of myocardial excitation and contraction. The electrical currents during ion-based depolarization and repolarization can be measured by electrical leads placed on the body in specific locations (the electrocardiogram) which measure electrical waves. The P-wave represents a wave of depolarization in the atrium. When the entire atria becomes depolarized, the wave returns to zero. After 0.1 seconds the ventricle is entirely depolarized resulting in the QRS complex. The three peaks are due to the way the current spreads in the ventricles. This is followed by the T-wave or repolarization of the ventricle. The QT interval measured from the beginning of the QRS complex to the end of the T-wave on the standard ECG represents the duration till the completion of the repolarization phase of the cardiac myocyte (or the depolarization and repolarization of the ventricle). The duration of this interval can vary due to genetic variation, cardiac disease, electrolyte balance, envenomation, and drugs. Prolongation of the QT interval, can result in ventricular arrhythmias, and sudden death.

Drug induced long QTc Syndrome (LQTS) i.e., a prolongation of the action potential duration is a common cause of governmental mandated drug withdrawal. QTc prolongation is an unpredictable risk factor for Torsades de Pointes (TdP), a polymorphic ventricular tachycardia leading to ventricular fibrillation. Drug induced LQTS comprises about 3% of all prescriptions which when followed by TdP may constitute a lethal adverse reaction. Patients taking one or more than one QTc-prolonging drug concomitantly, have an enhanced risk of TdP. While the overall occurrence of TdP is statistically rare but clinically significant for the affected individual, assay for this drug effect is a mandatory requirement prior to allowing a drug to enter clinical trials.

Common structurally diverse drugs block the human ether-a-g-go-related gene (KCNH2 or hERG) coded K$^+$ channel and the cardiac delayed-rectifier potassium current $I_K$ (KV11.1) resulting in acquired LQTS. Drug-associated increased risk of LQTS is a major drug development hurdle, and many drugs have been withdrawn during pre-clinical development, or assigned black box warnings following approval, or withdrawn from the market. Autosomal recessive or dominant LQTS based upon 500 possible mutations in 10 different genes coding for the potassium channel has an incidence of 1:3000 or about 100,000 persons in the US. Prolonged QT intervals or risk of LQTS occur in 2.5% of the asymptomatic US population. This syndrome when expressed can lead to severe cardiac arrhythmia and sudden death in untreated patients. The probability of cardiac death in patients with asymptomatic congenital LQTS who are medicated with LQTS-inducing drugs is increased.

The majority of the acquired LTQS drug withdrawals are due to obstruction of the potassium ion channels coded by the human ether-a-go-go related gene (hERG). High concentrations of hERG blocking drugs generally induce a prolonged QTc interval and increase the probability of TdP. Up to 10% of cases of drug-induced TdP can be due to 13 major genetic mutations, 471 different mutations, and 124 polymorphisms (Chig, C 2006).

Systems and methods for detection of LQTS have been described previously. For example U.S. Patent Publication No. 2010/0004549 (Kohls et al. 2010) discloses a system and method of detecting LQTS in a patient by comparing a collected set of ECG data from the patient to a plurality of databases of collected ECG data. The plurality of databases will include a database containing previous ECGs from the patient, a known acquired LQTS characteristics database, and a known genetic LQTS characteristics database. Comparing the patients ECG to these databases will facilitate the detection of such occurrences as changes in QT interval from success of ECGs, changes in T-wave morphology, changes in U-wave morphology and can match known genetic patterns of LQTS. The system and method is sensitive to patient gender and ethnicity, as these factors have been shown to effect LQTS, and is furthermore capable of matching a QT duration to a database of drug effects. The system and method is also easily integrated into current ECG management systems and storage devices.

A system and method for the diagnosis and treatment of LQTS is described in U.S. Patent Publication No. 2008/0255464 (Michael, 2008). The Michael invention includes a system for diagnosing Long QT Syndrome (LQTS) derives a QT/QS2 ratio from an electrical systole (QT) and a mechanical systole (QS2) to detect a prolonged QT interval in a patient's cardiac cycle. A processor acquires the systoles from a microphone and chest electrodes, calculates the QT/QS2 ratio, and outputs the result to a display. The processor may compare the QT/QS2 ratio to a threshold value stored in memory for diagnosing LQTS in the patient. A user interface provides for programming, set-up, and customizing the display. A mode selector allows the system to operate alternatively as a phonocardiograph, a 12 lead electrocardiograph, or a machine for diagnosing LQTS. A related method for diagnosing cardiac disorders such as LQTS includes measuring QT and QS2 during a same cardiac cycle, calculating a QT/QS2 ratio, and comparing the result to a threshold value derived from empirical data. The method may include measuring systoles both at rest and during exercise, and may be used for drug efficacy, dosage optimization, and acquired LQTS causality tests.

A method for the treatment of cardiac arrhythmias is provided in U.S. Patent Publication No. 2007/0048284 (Donahue and Marban, 2007). The method includes administering an amount of at least one polynucleotide that modulates an electrical property of the heart. The polynucleotides of the invention may also be used with a microdelivery vehicle such as cationic liposomes and adenoviral vectors.

Methods, compositions, dosing regimes, and routes of administration for the treatment or prevention of arrhythmias have been described by Fedida et al. (2010) in U.S. Patent Publication No. 2001/00120890. In the Fedida invention, early after depolarizations and prolongation of QT interval may be reduced or eliminated by administering ion channel modulating compounds to a subject in need thereof. The ion channel modulating compounds may be cycloalkylamine ether compounds, particularly cyclohexylamine ether compounds. Also described are compositions of ion channel modulating compounds and drugs which induce early after depolarizations, prolongation of QT interval and/or Torsades de Pointes. The Fedida invention also discloses antioxidants which may be provided in combination with the ion channel modulating compounds, non-limiting examples of the antioxidants include vitamin C, vitamin E, beta-carotene, lutein, lycopene, vitamin B2, coenzyme Q10, cysteine as well as herbs, such as bilberry, turmeric (curcumin), grape seed or pine bark extracts, and ginkgo.

SUMMARY OF THE INVENTION

Crizotinib (Xalkori®) and nilotinib (Tasigna®) are tyrosine kinase inhibitors approved for the treatment of non-small cell lung cancer and chronic myeloid leukemia, respectively. Both have been shown to result in QT prolongation in humans and animals. Liposomes have been shown to ameliorate drug-induced effects on the IKr (KV11.1) channel, coded by the human ether-a-go-go-related gene (hERG). This study was done to determine if liposomes would also decrease the effect of crizotinib and nilotinib on the IKr channel. Crizotinib and nilotinib were tested in a standard in vitro IKr assay using human embryonic kidney (HEK) 293 cells stably transfected with the hERG. Dose-responses were determined and 50% inhibitory concentrations ($IC_{50}$s) were calculated. When the HEK 293 cells were treated with crizotinib and nilotinib that were mixed with liposomes, there was a significant decrease in the IKr channel inhibitory effects of these two drugs. The use of liposomal encapsulated QT-prolongation agents, or just mixing these drugs with liposomes, e.g., empty liposomes, was found to decrease their cardiac liability.

In one embodiment, the present invention includes a composition for preventing one or more cardiac channelopathies or conditions resulting from irregularities or alterations in cardiac patterns, or both, in a human or animal subject comprising: one or more pharmacologically active agents that causes at least one of IKr channel inhibition or QT prolongation by inhibiting the activity of an ether-a-go-go-related gene (hERG); and one or more liposomes, wherein the liposomes are empty liposomes and administered prior to, concomitantly, or after administration of the pharmacologically active agent. In one aspect, the cardiac channelopathy or the condition resulting from the irregularity or alteration in the cardiac pattern is inhibition of an ion channel responsible for the delayed-rectifier K+ current in the heart, polymorphic ventricular tachycardia, prolongation of the QTc, LQT2, LQTS, or torsades de pointes. In another aspect, the composition is used for the treatment or prevention of prolongation of the IKr channel inhibition or QT prolongation induced by administration of one or more drugs used in the treatment of cardiac or non-cardiac related diseases. In another aspect, the one or more active agents is selected from at least one of crizotinib, nilotinib, terfenadine, astemizole, gripafloxacin, terodilene, droperidole, lidoflazine, levomethadyl, sertindoyle or cisapride. In another aspect, the one or more active agents is selected from at least one of: Aloxi; Amiodarone; Arsenic trioxide; Astemizole; Bepridil; Chloroquine; Chlorpheniramine; Chlorpromazine (Thorazine); Cisapride; Celaxa; Citalopram; Clarithromycin; Erythromycin; Curcumin; Disopyramide; Dofetilide; Domperidone; Doxorubicin; Dronedarone; Droperidol; Grepafloxacin; Haldol; Haloperidol; Halofantrine; Ibutilide; Levomethadyl; Lidoflazine; Loratidine; Lovostatin; Mesoridazone; Methadone; Methanesulphonanilide; Moxifloxacin; Palonasitron; Pentamadine; Pimozide; Prenylamine; Probucol; Procainamide; Propafenone; Pyrilamine; Quinidine; Terfenidine; Sertindole; Sotalol; Sparfloxacin; Thioridazine; or Vandetanib. In another aspect, the composition is adapted for enteral, parenteral, intravenous, intraperitoneal, or oral administration. In one aspect, the composition consists essentially of the therapeutically effective amount of a composition comprising: one or more pharmacologically active agents that cause cardiac channelopathies or conditions resulting from irregularities or alterations in cardiac patterns and the empty liposomes, wherein the amount of empty liposomes is sufficient to reduce the cardiac channelopathies or conditions resulting from irregularities or alterations in cardiac patterns caused by the active agent. In another aspect, the active agent and the liposomes may be bound or conjugated together. In another aspect, the liposomes comprise anionic, cationic, or neutral liposomes. In another aspect, the liposomes comprises a lipid or a phospholipid wall, wherein the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In another aspect, the composition further comprises a pharmaceutically acceptable dispersion medium, solvent, or vehicle, wherein the active agent, the liposome or both are dissolved, dispersed, or suspended in the medium, the solvent, or the vehicle. In another aspect, the liposomes comprise DMPC (1,2-dimyristoil-sn-glycero-3-phosphocholine) and DMPG (1,2-dimyristoyl-sn-glycero-3-phospho-rac-[1-glycerol]). In another aspect, the liposomes comprise a 9.7:1 ratio of DMPC (1,2-dimyristoil-sn-glycero-3-phosphocholine) and DMPG (1,2-dimyristoyl-sn-glycero-3 -phospho-rac-[1-glycerol]).

In one embodiment, the present invention includes a composition for preventing or treating one or more adverse reactions arising from administration of a therapeutically active agent or a drug in a human that causes at least one of IKr channel inhibition or QT prolongation by inhibiting the activity of an ether-a-go-go-related gene (hERG) comprising: one or more pharmacologically active agents that causes at least one of IKr channel inhibition or QT prolongation and one or more liposomes, wherein the liposomes are empty liposomes and administered prior to, concomitantly, or after administration of the therapeutically active agent or the drug and the liposomes are provided in an amount sufficient to reduce or eliminate the IKr channelopathy or QT prolongation. In one aspect, the therapeutically active agent or a drug is used in a prevention or a treatment of one or more cardiac or non-cardiac diseases in the human or animal subject. In another aspect, the cardiac channelopathy or the condition resulting from the irregularity or alteration in the cardiac pattern is inhibition of an ion channel responsible for the delayed-rectifier K+ current in the heart, polymorphic ventricular tachycardia, prolongation of the QTc, LQT2, LQTS, or torsades de pointes. In another aspect, the composition is used for the treatment or prevention of prolongation of the IKr channel inhibition or QT prolongation induced by administration of one or more drugs used in the treatment of cardiac or non-cardiac related diseases. In another aspect, the one or more active agents is selected from at least one of crizotinib, nilotinib, terfenadine, astemizole, gripafloxacin, terodilene, droperidole, lidoflazine, levomethadyl, sertindoyle or cisapride. In another aspect, the one or more active agents is selected from at least one of: Aloxi; Amiodarone; Arsenic trioxide; Astemizole; Bepridil; Chloroquine; Chlorpheniramine; Chlorpromazine (Thorazine); Cisapride; Celaxa; Citalopram; Clarithromycin; Erythromycin; Curcumin; Disopyramide; Dofetilide; Domperidone; Doxorubicin; Dronedarone; Droperidol; Grepafloxacin; Haldol; Haloperidol; Halofantrine; Ibutilide; Levomethadyl; Lidoflazine; Loratidine; Lovostatin; Mesoridazone; Methadone; Methanesulphonanilide; Moxifloxacin; Palonasitron; Pentamadine; Pimozide; Prenylamine; Probucol; Procainamide; Propafenone; Pyrilamine; Quinidine; Terfenidine; Sertindole; Sotalol; Sparfloxacin; Thioridazine; or Vandetanib. In another aspect, the composition is adapted for enteral, parenteral, intravenous, intraperitoneal, or oral administration. In another aspect, the active agent and the liposomes may be bound or conjugated together. In another aspect, the liposomes comprise anionic, cationic, or neutral liposomes. In another aspect, the liposomes comprises a lipid or a phospholipid wall, wherein the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In another aspect, the liposomes are spherical liposomes with a diameter ranging from 10 nm-200 nm. In another aspect, the liposomes comprise DMPC (1,2-dimyristoil-sn-glycero-3-phosphocholine) and DMPG (1,2-dimyristoyl-sn-glycero-3-phospho-rac-[1-glycerol]). In another aspect, the liposomes comprise a 9.7:1 ratio of DMPC (1,2-dimyristoil-sn-glycero-3-phosphocholine) and DMPG (1,2-dimyristoyl-sn-glycero-3 -phospho-rac-[1-glycerol]).

In another embodiment, the present invention includes a method for preventing or treating one or more cardiac channelopathies, irregularities or alterations in cardiac patterns, or both in a human or animal subject comprising the steps of: identifying the human or animal subject in need of prevention or treatment of the one or more cardiac channelopathies, irregularities or alterations in cardiac patterns, or both; and administering to the human or animal subject a therapeutically effective amount of a composition comprising: one or more pharmacologically active agents that causes at least one of IKr channel inhibition or QT prolongation by inhibiting the activity of an ether-a-go-go-related gene (hERG); one or more liposomes, wherein the liposomes are empty liposomes and administered prior to, concomitantly, or after administration of the pharmacologically active agent in an amount sufficient to prevent or treat one or more cardiac channelopathies, irregularities or alterations in cardiac patterns; and an optional pharmaceutically acceptable dispersion medium, solvent, or vehicle, wherein the active agent, the liposome or both are dissolved, dispersed, or suspended in the medium, the solvent, or the vehicle. In one aspect, the composition consists essentially of the therapeutically effective amount of a composition comprising: one or more pharmacologically active agents that causes at least one of IKr channel inhibition or QT prolongation by inhibiting the activity of an ether-a-go-go-related gene (hERG) and the empty liposomes, wherein the amount of empty liposomes is sufficient to reduce the IKr channel inhibition or QT prolongation. In one aspect, the cardiac channelopathy or the condition resulting from the irregularity or alteration in the cardiac pattern is inhibition of an ion channel responsible for the delayed-rectifier K+ current in the heart, polymorphic ventricular tachycardia, prolongation of the QTc, LQT2, LQTS, or torsades de pointes. In another aspect, the one or more active agents is selected from at least one of crizotinib, nilotinib, terfenadine, astemizole, gripafloxacin, terodilene, droperidole, lidoflazine, levomethadyl, sertindoyle or cisapride. In another aspect, the liposomes comprise DMPC (1,2-dimyristoil-sn-glycero-3-phosphocholine) and DMPG (1,2-dimyristoyl-sn-glycero-3-phospho-rac-[1-glycerol]). In another aspect, the liposomes comprise a 9.7:1 ratio of DMPC (1,2-dimyristoil-sn-glycero-3-phosphocholine) and DMPG (1,2-dimyristoyl-sn-glycero-3-phospho-rac-[1-glycerol]). In another aspect, the one or more active agents is selected from at least one of: Aloxi; Amiodarone; Arsenic trioxide; Astemizole; Bepridil; Chloroquine; Chlorpheniramine; Chlorpromazine (Thorazine); Cisapride; Celaxa; Citalopram; Clarithromycin; Erythromycin; Curcumin; Disopyramide; Dofetilide; Domperidone; Doxorubicin; Dronedarone; Droperidol; Grepafloxacin; Haldol; Haloperidol; Halofantrine; Ibutilide; Levomethadyl; Lidoflazine; Loratidine; Lovostatin; Mesoridazone; Methadone; Methanesulphonanilide; Moxifloxacin; Palonasitron; Pentamadine; Pimozide; Prenylamine; Probucol; Procainamide; Propafenone; Pyrilamine; Quinidine; Terfenidine; Sertindole; Sotalol; Sparfloxacin; Thioridazine; or Vandetanib.

In yet another embodiment, the present invention includes a method for preventing or treating one or more adverse reactions arising from administration of a therapeutically active agent or a drug in a human or animal subject comprising the steps of: identifying the human or animal subject in need of prevention or treatment of the one or more adverse reactions arising from the administration of the therapeutically active agent or the drug that causes at least one of IKr channel inhibition or QT prolongation by inhibiting the activity of an ether-a-go-go-related gene (hERG); and administering to the human or animal subject a therapeutically effective amount of a composition comprising one or more liposomes, wherein the liposomes are empty liposomes and administered prior to, concomitantly, or after administration of the therapeutically active agent or the drug or are liposomes loaded with the therapeutically active agent or the drug; and measuring the effect of the combination of the liposomes and the therapeutically active agent or the drug on the drug-induced channelopathy, wherein the composition reduces or eliminated the channelopathy induced by the therapeutically active agent or the drug. In one aspect, the one or more active agents or drugs is selected from at least one of: Aloxi; Amiodarone; Arsenic trioxide; Astemizole; Bepridil; Chloroquine; Chlorpheniramine; Chlorpromazine (Thorazine); Cisapride; Celaxa; Citalopram; Clarithromycin; Erythromycin; Curcumin; Disopyramide; Dofetilide; Domperidone; Doxorubicin; Dronedarone; Droperidol; Grepafloxacin; Haldol; Haloperidol; Halofantrine; Ibutilide; Levomethadyl; Lidoflazine; Loratidine; Lovostatin; Mesoridazone; Methadone; Methanesulphonanilide; Moxifloxacin; Palonasitron; Pentamadine; Pimozide; Prenylamine; Probucol; Procainamide; Propafenone; Pyrilamine; Quinidine; Terfenidine; Sertindole; Sotalol; Sparfloxacin; Thioridazine; or Vandetanib.

In another embodiment, the present invention includes a method for preventing or treating at least one of IKr channel inhibition or QT prolongation arising from administration of crizotinib, nilotinib, or any other active agent that causes a drug-induced channelopathy in a human or animal subject comprising the steps of: identifying the human or animal subject in need of prevention or treatment at least one of IKr channel inhibition or QT prolongation that results from the administration of crizotinib, nilotinib, or any other active agent that causes a drug-induced channelopathy; and administering to the human or animal subject a therapeutically effective amount of a composition comprising one or more liposomes, wherein the liposomes are empty liposomes and administered prior to, concomitantly, or after administration of the crizotinib, nilotinib, or any other active agent that causes a drug-induced channelopathy, wherein the composition reduces or eliminated the channelopathy induced by the therapeutically active agent or the drug. In one aspect, the active agent has previously failed a clinical trial due to drug-induced IKr channel inhibition or QT prolongation. In another aspect, the method further comprises the step of identifying a drug in a clinical trial that failed or has limited clinical use due to drug-induced IKr channel inhibition or QT prolongation side-effects. In one aspect, the one or more active agents is selected from at least one of: Aloxi; Amiodarone; Arsenic trioxide; Astemizole; Bepridil; Chloroquine; Chlorpheniramine; Chlorpromazine (Thorazine); Cisapride; Celaxa; Citalopram; Clarithromycin; Erythromycin; Curcumin; Disopyramide; Dofetilide; Domperidone; Doxorubicin; Dronedarone; Droperidol; Grepafloxacin; Haldol; Haloperidol; Halofantrine; Ibutilide; Levomethadyl; Lidoflazine; Loratidine; Lovostatin; Mesoridazone; Methadone; Methanesulphonanilide; Moxifloxacin; Palonasitron; Pentamadine; Pimozide; Prenylamine; Probucol; Procainamide; Propafenone; Pyrilamine; Quinidine; Terfenidine; Sertindole; Sotalol; Sparfloxacin; Thioridazine; or Vandetanib.

In another embodiment, the present invention includes a method of evaluating a candidate drug that reduces a channelopathy caused by a pharmacologically active agent, the method comprising: (a) administering a candidate drug to a first subset of the patients, and a placebo to a second subset of the patients, wherein the composition is provided in conjunction with the pharmacologically active agent that causes at least one of $I_{Kr}$ channel inhibition or QT prolongation and one or more liposomes, wherein the liposomes are empty liposomes and administered prior to, concomitantly, or after administration of the therapeutically active agent or the drug; (b) measuring the channelopathy from a suspected of having a drug-induced channelopathy from a set of patients; (c) repeating step (a) after the administration of the candidate drug or the placebo; and (d) determining if the composition reduces the drug-induced channelopapthy that is statistically significant as compared to any reduction occurring in the second subset of patients, wherein a statistically significant reduction indicates that the candidate drug is useful in treating said disease state. In one aspect, the drug has previously failed a clinical trial due to drug-induced IKr channel inhibition or QT prolongation. In another aspect, the one or more active agents is selected from at least one of: Aloxi; Amiodarone; Arsenic trioxide; Astemizole; Bepridil; Chloroquine; Chlorpheniramine; Chlorpromazine (Thorazine); Cisapride; Celaxa; Citalopram; Clarithromycin; Erythromycin; Curcumin; Disopyramide; Dofetilide; Domperidone; Doxorubicin; Dronedarone; Droperidol; Grepafloxacin; Haldol; Haloperidol; Halofantrine; Ibutilide; Levomethadyl; Lidoflazine; Loratidine; Lovostatin; Mesoridazone; Methadone; Methanesulphonanilide; Moxifloxacin; Palonasitron; Pentamadine; Pimozide; Prenylamine; Probucol; Procainamide; Propafenone; Pyrilamine; Quinidine; Terfenidine; Sertindole; Sotalol; Sparfloxacin; Thioridazine; or Vandetanib. In one aspect, the method is conducted in vitro.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
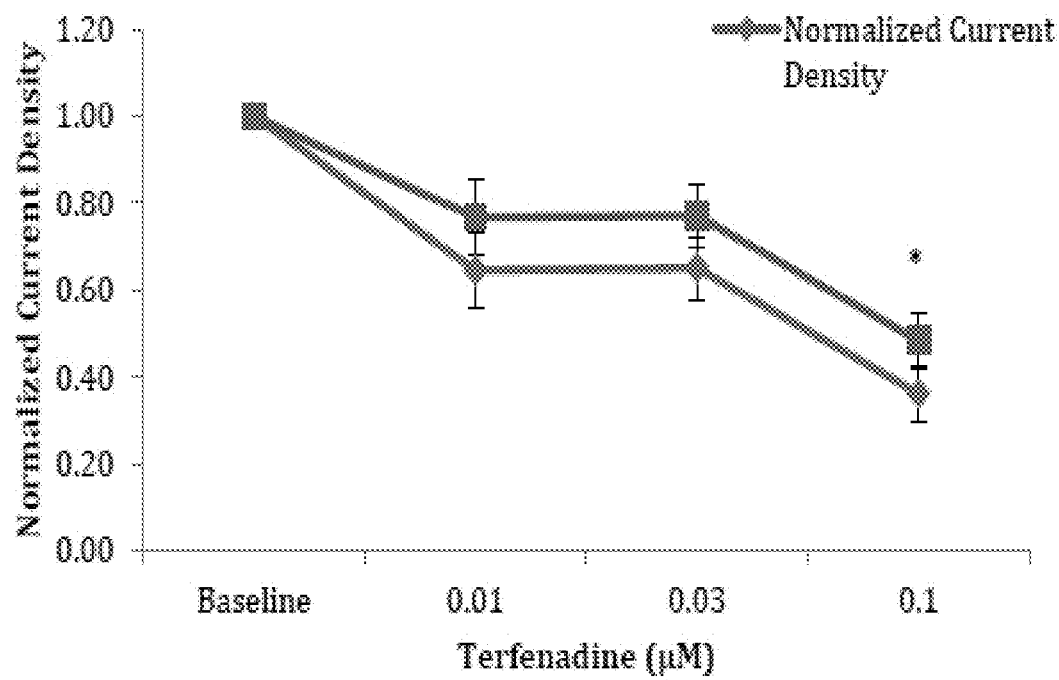
FIG. 1 is a graph that shows the effect of terfenadine on hERG current density from transfected HEK 293 cells at 20 mV.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "Curcumin", "diferuloylmethane", or "1,7-bis(4-hydroxy-3-methoxyphenyl)-1,6-heptadiene-3,5-dione)" is a naturally occurring compound which is the main coloring principle found in the rhizomes of the plant *Curcuma longa* (see e.g., U.S. Pat. No. 5,679,864, Krackov et al.).

The term "liposome" refers to a capsule wherein the wall or membrane thereof is formed of lipids, especially phospholipid, with the optional addition therewith of a sterol, especially cholesterol.

As used herein, the term "in vivo" refers to being inside the body. The term "in vitro" used as used in the present application is to be understood as indicating an operation carried out in a non-living system.

As used herein, the term "receptor" includes, for example, molecules that reside on the surface of cells and mediate activation of the cells by activating ligands, but also is used generically to mean any molecule that binds specifically to a counterpart. One member of a specific binding pair would arbitrarily be called a "receptor" and the other a "ligand." No particular physiological function need be associated with this specific binding. Thus, for example, a "receptor" might include antibodies, immunologically reactive portions of antibodies, molecules that are designed to complement other molecules, and so forth. Indeed, in the context of the present invention, the distinction between "receptor" and "ligand" is entirely irrelevant; the invention concerns pairs of molecules, which specifically bind each other with greater affinity than either binds other molecules. However, for ease of explanation, the invention method will be discussed in terms of target receptor (again, simply a molecule for which a counterpart is sought that will react or bind with it) and "ligand" simply represents that counterpart.

As used herein, the term "treatment" refers to the treatment of the conditions mentioned herein, particularly in a patient who demonstrates symptoms of the disease or disorder.

As used herein, the term "treating" refers to any administration of a compound of the present invention and includes (i) inhibiting the disease in an animal that is experiencing or displaying the pathology or symptomatology of the diseased (i.e., arresting further development of the pathology and/or symptomatology); or (ii) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The terms "effective amount" or "therapeutically effective amount" described herein means the amount of the subject compound that will elicit the biological or medical response of a tissue, system, animal or human that is being sought by the researcher, veterinarian, medical doctor or other clinician.

The terms "administration of" or "administering a" compound as used herein should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

As used herein the term "intravenous administration" includes injection and other modes of intravenous administration.

The term "pharmaceutically acceptable" as used herein to describe a carrier, diluent or excipient must be compatible with the other ingredients of the formulation and not deleterious to the recipient thereof The term "hERG" as used herein refers to the human Ether-a-go-go-Related Gene, which is encoded by the KCNH2 gene (see www.genecards.com). The KCNH2 gene encodes a protein also known as Kvl 1.1, which is the alpha subunit of a potassium ion channel that contributes to the electrical activity of the heart that coordinates the heart's beating. Specifically, the hERG-containing channel mediates the repolarizing IKr current in the cardiac action potential.

Inhibition of the ion channel's ability to conduct electrical current across the cell membrane results in a potentially fatal disorder called long QT syndrome. A number of clinically successful drugs in the market have been found to inhibit hERG, thus creating a risk of sudden death. This drug-induced side-effect has caused hERG inhibition a key target to be avoided during drug development.

The term "$I_{Kr}$" channel" as used herein refers to the 'rapid' delayed rectifier current Oa that conducts potassium ($K^-$) ions out of the muscle cells of the heart (cardiac myocytes). This current is critical in correctly timing the return to the resting state (repolarization) of the cell membrane during the cardiac action potential. Often, the terms "hERG channels" and $I_{Kr}$ are used interchangeably, although hERG forms part of naturally occurring channels in the body, which are more commonly referred to by the name of the electrical current that has been measured in that cell type, which in the case of the heart is $I_{Kr}$.

EXAMPLE 1

Compositions and Methods for Controlling the Duration of Repolarization of the Cardiac Ventricle QT Interval Compositions and methods for controlling the duration of repolarization of the cardiac ventricle QT interval are disclosed herein. The method of the present invention comprises comprising administering to subject in need thereof of a modification of or a functional interference with a therapeutic agent, or a congenital defect which if unmodified can induce prolongation of repolarization in the heart myocyte action potential, torsade de points, and the long QT syndrome. The present invention comprises of either binding a QT prolonging drug with a liposome prior to parenteral (intravenous or subcutaneous) administration, or empty liposomal administration prior to or concomitantly with one or more therapeutic agents known to have a high risk of QT prolongation, or immediately following an envenomation. The findings of the present invention indicate that the adverse effect of curcumin and other QT prolonging drugs is abrogated with liposomal curcumin, and with vortexed mixtures of empty liposomes in a dose dependent manner.

Ion channels are pore-forming integral membrane proteins that establish and control the electrochemical gradient (the action potential) across the plasma membrane, and intracellular organelles of cells by modulating ion. The channels are assembled as a circular arrangement of proteins packed around a water-filled pore. The ions passage through the channel in single file, which may be open or closed by chemical, electrical signals, temperature, or mechanical force. Ion channel dysfunction may be associated with mutations in the genes coding these channels or with drugs interfering with ion flow. Dysfunction in cardiac electrolyte potassium, calcium, and sodium channels in the cardiac myocyte membrane induces defects in electrical currents, and the normal action potential which are necessary for coordinated myocyte contraction and maintenance of normal blood circulation resulting in clinical cardiac symptoms. The central roles of the 40 members, and 12 subfamilies of voltage gated potassium channel's (Kv) role are to repolarize the cell membrane following action potentials. The flux of potassium ions in the cardiac myocyte $K^+$ channels modulates electrolytic currents, levels of depolarization and repolarization. Congenital and/or drug-induced channel defects are associated with morbidity and mortality in otherwise asymptomatic individuals. The channel proper coded by the gene KCNH2 or hERG (human ether-a-go-go-related gene) contains proteins designated as Kv11.1 and the Lv11.1 α-subunit of the rapidly activating rectifier $K^+$ current $I_{Kr}$. This cell membrane channel mediates the "rapid" delayed rectifier current $I_{Kr}$ by conducting $K^+$ ions out of the cardiac myocytes and is a critical mechanism to allow the cardiac potential to return to the resting state (repolarization).

Even though the hERG channel pore-domain lacks a known three-dimensional structure, insight into its putative structure has been gained from site-directed mutagenesis data (Stansfeld P J, 2007). Within the hERG channel pore cavity, ion flux and currents can be modified depending upon the open or closed states, and by drug interactions at key high affinity drug binding sites. These sites are the aromatic amino-acid residues (Y652 and F656) on the inner helices of the pore. The most important currents mediated by drugs, the sensitive delayed, $I_{Kr}$ (rapid) current which repolarizes the myocardial cells and the $I_{Ks}$ (slow) rectifier currents are exhibited on the standard electrocardiogram (ECG) as the QT interval which when corrected for heart rate this is conventionally defined as QTc.

Congenital defects in ion channels first described by Jervell A, (1957), alter the balance of currents determining repolarization of the action potential and predispose to LQTS arrhythmias.and sudden cardiac death. Mutations have been identified giving rise to subtypes of congenital LQTS, familial arrhythmogenic syndromes characterized by abnormal ion channel function, delayed repolarization, prolonged QT interval on the electrocardiogram and a life-threatening polymorphic ventricular tachycardia known as torsade de points. Different mutations in the hERG gene and its coded proteins translate to defects in channel function and a number of clinical syndromes. Type 2 congenital long-QT syndrome (LQT2) results from A614V missense mutations in the KCNH gene and is characterized by four classes of loss of Kv11.1 protein and consequent channel dysfunction. These abnormal Kv11.1 channels include (Class 1), a dominant—intracellular trafficking-deficient ion channel protein: usually due to missense mutations, (Class 2), a correctible phenotype when cells are incubated for 24 hours at 27° temperature, or with exposure to the drugs E-4031 (Zhou Z 1999 (Class 3)), channel gating, and (Class 4) permeation)(Anderson C.L, 2006). Blockade by any of these and particularly the "rapid" current prolongs the action potential and manifests on the ECG as a prolonged QT interval and emergence of other T or U wave abnormalities. Under such circumstances, activation of an inward depolarization current induces increased dispersion of repolarization. The latter results in a heterogeneous recovery of excitability, and induction of torsades de points (TdP) an early premature ventricular contraction (PVC). (R-On-T). This is where ventricular depolarization i.e, the R-wave occurs simultaneously with the relative refractory period at the end of repolarization (latter half of the T-wave) and initiates pathologic T-U waves and torsades. Sustained TdP leads to a zone of functional refractoriness in the myocardium, and cardiac arryhthmias. The ECG reading in torsades exhibits a rapid polymorphic ventricular tachycardia with a characteristic twist of the QRS complex around the isoelectric baseline. This is characterized by a rotation of the heart's electrical axis by as much as 180°, long and short RR-intervals, and clinically this leads to a fall in arterial blood pressure, syncope, degeneration into ventricular fibrillation and sudden death.

On the ECG, retardation of the $I_{Kr}$ current interval is synonymous with QT prolongation when greater than 440 ms in men and 460 ms in women. Pharmacological inhibition of hERG K$^+$ channels by structurally and therapeutically diverse drugs translates to the clinical acquired form of the long QT syndrome (LQTS). While QT prolonging drugs represent two to three percent of the total prescriptions in the developed world the reported incidence of QT prolongation and dosage varies significantly within different drug classes. The latter include Class 1A and Class III antiarrhythmics, antihistamines, antimicrobials, antipsychotics, tricyclic antidepressants, prokinetics, and anti-anginals. Recently, curcuminoids were reported to block human cardiac K$^+$ channels. (Moha ou Maati H, 2008).

Increased incidence of QT prolongation may also occur in the presence of hypomagnesemia, hypokalemia, hypocalcemia, hypoxia, acidosis, heart failure, left ventricular hypertrophy, slow heart rate, female gender, hypothermia, and subarachnoid hemorrhage. The severity of arrhythmia at a given QT interval, and development of TdP varies from drug to drug and patient to patient and may not be linearly related to the dose or plasma concentration of a specific drug. However, antiarrhythmic cardiac drugs affecting the potassium (K$^+$) efflux (Class III) and non-cardiac drugs: that significantly alter repolarization, as measured by prolongation of the QT interval predispose the patient to torsades. Additional factors associated with an increased tendency toward TdP include familial long QT syndrome (LQTS). The most common causes of familial LQTS are mutations in genes.

KCNQ1 codes for KvLTQ1, the alpha subunit of the slow delayed potassium rectifier potassium channel is highly expressed in the heart. The current through the heteromeric channel when interacting with the minK beta subunit is known as $I_{Ks}$. When missense mutated it reduces the amount of repolarizing current needed to terminate the action potential. These LTQ1 mutations represent 35% of all cases, and are the least severe, usually causing syncope.

KCNH2 or the hERG gene when mutated represents 30% of all genetic cases, and is the subunit of the rapid delayed rectifier potassium channel hERG+MiRP 1. Current through this channel known as $I_{Kr}$ is responsible for termination of the action potential and the length of the QT interval. When reduced it leads to LQT2. The rapid current is not only the most drug sensitive, but also is associated with the pro-arrhythmic effect in His-Purkinje cells and M cells in the mid-ventricular myocardium. Drug induced LQTs occurs with anti-arrhythmic drugs, antihistamines, anti-psychotic and other drugs. The combination of genetic LQTS and LQTS-inducing drugs increase susceptibility to lethal side effects. Most drugs causing LKTS block the $I_{Kr}$ current via the hERG gene. This channel exhibits unintended drug binding at tyrosine 652 and phenylalanine 656 which when bound block current conduction. Uncommon but lethal mutations in gene SCN5A slow inactivation of the alpha subunit of the sodium channel, prolonging Na$^+$ influx and the current $I_{Na}$ during depolarization. Continued depolarizing current through the channel late in the action potential induces a late bursting current (LQT3).

L-type calcium channels re-open during the plateau phase of the action potential following LQTS as "early after depolarizations." Their activity is sensitive to adrenergic stimulation and increases the risk of sudden death during adrenergic states in the presence of impaired repolarization. In these subjects TdP can be precipitated following exercise, or emotional surprise unrelated to drugs. There are additional uncommon and rare mutations designated LQT4-13.

Apart from heart rate, the QT duration varies with recording and measurement techniques, sympatho-vagal activity, drugs, electrolyte disorders, cardiac or metabolic diseases, diurnal variation and genetic LQT2 mutations. These parameters cause the reported incidence of drug-induced TdP to be loosely associated with clinical studies during drug development, post-marketing surveillance, epidemiologic studies, and anecdotal case reports. Detection of QT prolongation during pre-clinical drug development can lead to abandonment and precludes any all-inclusive accounting of the actual incidence of drug related QT prolongation (Yap 2003). A number of QT-prolonging drugs have been withdrawn either during development or after being on the market. These include Terfenadine, Astemizole, Gripafloxacin, Terodilene, Droperidole, Lidoflazine, Levomethadyl, Sertindoyle, levomethadyl, and Cisapride.

Genetic and age related susceptibility: there are predispositions to QT-prolonging drug events: this includes patients with structural heart disease, taking hepatic C450 inhibitors, who have a genetic predisposition, or DNA polymorphisms. Old females generally are more susceptible than young females, while young males have increased susceptibility compared to elderly males.

Current Therapy for QT prolonging-drugs, and in genotypic QT sensitivity: Pharmacological therapy: first line treatment for LQTS, a potentially lethal disease with a 13% incidence of cardiac arrest and sudden death. (i) Dexrazoxane: (a piperazinedione cyclic derivative of edetic acid). It diminishes but does not eliminate the potential for anthracycline induced cardiotoxicity associated with over 300 mg/M$^2$ epirubicin administered to patients with breast cancer. Use of intravenous Dexrazoxane is limited to anthracyclines only, i.e. it is contraindicated in chemotherapy regimens that do not contain an anthracycline. (ii) β-blockers: propranolol as sympathetic stimulation therapy may decrease risk of cardiac events by 81% in LQT1, it may also suppress isoproteranolol augmentation of transmural dispersion of repolarization(TDR) and TdP, however on adequate propranolol treatment 10% still develop cardiac events. In LQT2 subjects, cardiac event risk is decreased 59%, however 23% still develop cardiac events. (iii) Sodium channel blockers: 32% of LQT3 subjects develop cardiac events on adequate propranolol. In these subjects with low heart rates, β-blockers may increase dispersion of repolarization and risk of TdP. LQT3 subjects with sodium channel mutations preventing inactivation and inducing persistent increase in late $I_{Na}$ during phase 2 of the action potential, a cause of QT prolongation using, mexiletine (Shimizu W, 1997) a Class IB sodium channel blocker abbreviates the QT interval by reduction of TDR. (iv) Potassium supplementation: both $I_{Kr}$ and $I_{K1}$ are sensitive to extracellular potassium levels. Raising plasma concentration by 1.5 mEq/L above baseline can reduce the QTc interval by 24% (Compton 1996 and Etheredge 2003), but there is no evidence that it translates in arrhythmia protection. (v) Potassium channel openers: Nicorandil, a potassium channel opener given intravenously at 2-20 umol/L appreviates the QT interval in LQT1 and LQT2 subjects.(Shimizu W 2000). (vi) hERG current enhancers: RPR 260243 reverses dofetalide-induced action potential prolongation in guinea pig myocytes (Kang J2005). (vii) Calcium channel blockers: Calcium influx through L-type calcium channels maintains the plateau phase, the duration of the action potential and the QT interval of the action potential. Verapamil an L-type calcium channel blocker, and inhibitor of $I_{Na}$ abbreviates the QT interval and suppresses TdP in LQTS models is used in patients with paroxysmal atria-ventricular nodal reentrant tachycardia with significantly shortened QT at low heart rates. The hERG inhibitory $EC_{50}$ is 83 uM. When verapamil is administered at appropriate dosage, torsades de points may be avoided (Fauchier L 1999). (viii) Trafficking defects correction: Defects in transport of proteins and glycoproteins forming trans-membrane ion pores in the cardiac cell membrane reduce the amplitude of corresponding currents and have a role in LQTS. Fexofenadine, a metabolite of terfenadine or thapsigargin can rescue such defective trafficking without blocking hERG current in selective missense mutations associated with LQT2. (ix) Gap Junction coupling enhancers: Gap junctions are intercellular channels allowing both small molecules and current to be transferred between cardiac cells. Heart failure and hypertrophy are associated with uncoupling of gap junctions. Enhancing gap junctions can produce an anti-arrhythmic effect where dispersion of repolarization is enhanced in LQTS. Infusion of a synthetic peptide, AAP10 a gap junction enhancer reduces the QT interval in the rabbit left ventricular preparation (Quan XQ, 2007).

This nonclinical laboratory study described in the present invention was conducted in accordance with the United States Food and Drug Administration (FDA) Good Laboratory Practice Regulations, 21 CFR Part 58, the Organization for Economic Cooperation and Development (OECD) Principals of Good Laboratory Practice [C(97) 186/Final], issued November 26, 1997, and the Japanese Ministry of Health, Labour and Welfare (MHLW) Good Laboratory Practice Standards Ordinance No. 21, Mar. 26, 1997.

Study Outline: 1) Test articles: Curcumin, Empty Liposomes, Liposomal curcumin, (0.014, 0.20, 3.4 and 11.4 μM); 2) Test System: hERG-expressing HEK 293 transfected cell line; 3) Test performed: Whole-cell patch-clamp current acquisition and analysis; 4) Experimental Temperature: 35±2° C.

Application of test article: 1) 5 minutes of exposure to each concentration in presence of closed circuit perfusion (2 mL/min); 2) 5 minutes for washout periods in presence of a flow-through perfusion (2mL/min) in addition to a closed circuit perfusion (2 mL/min); 3) The positive controls, (100nM E-4031, and Terfenadine (0.01, 0.03, 0.1 uM) were added to naive cells obtained from the same cell line and same passage for a period of 5 minutes in presence of a closed circuit perfusion (2 mL/min); 4) Curcumin, Terfenadine and E-4031 were each vortexed for 15 minutes with empty liposomes, and then tested. Cells were under continuous stimulation of the pulses protocol throughout the studies and cell currents were recorded after 5 minutes of exposure to each condition.

Data acquisition design: Acquisition Rate(s): 1.0 kHz. Design for acquisition when testing the compounds or the vehicle/solvent equivalent: 1 recording made in baseline condition, 1 recording made in the presence of concentration 1, 2, 3 or 4, and 1 recording made after washout (only after the fourth concentration). Design for acquisition when testing the positive controls: 1 recording made in baseline condition, 1 recording made in the presence of the positive control, and n =number of responsive cells patched on which the whole protocol above could be applied.

Statistical analysis: Statistical comparisons were made using paired Student's t-tests. For the test articles, the currents recorded after exposure to the different test article concentrations were statistically compared to the currents recorded in baseline conditions. Currents, recorded after the washout, were statistically compared to the currents measured after the highest concentration of test article. In the same way, currents recorded after the positive control, were compared to the currents recorded in baseline conditions. Differences were considered significant when p≤0.05.

Data Exclusion criteria: 1) Timeframe of drug exposure not respected; 2) Instability of the seal; 3) No tail current generated by the patched cell; 4) No significant effect of the positive control; and 5) More than 10% variability in capacitance transient amplitude over the duration of the study.

The in vitro effects of curcumin, liposomal curcumin, empty liposome and positive controls E-4031 and Terfenadine were determined on the human delayed rectifier current using human embryonic kidney (HEK) 293 cells transfected with the human ether-a-go-go-related gene (hERG).

$I_{Kr}$ channel inhibition and cardiac toxicity has become a major liability for some classes of drugs, in particular, those that trigger $I_{Kr}$ channel inhibition and/or in vivo QT prolongation. Many drugs have been found to have this activity during preclinical drug development, which has led to the abandonment of many promising drug classes. A number of QT-prolonging drugs have been withdrawn or have very limited use as a result of this activity. Examples include, but are not limited to: crizotinib, nilotinib, terfenadine, astemizole, gripafloxacin, terodilene, droperidole, lidoflazine, levomethadyl, sertindoyle and cisapride.

There are a great number of drugs that are currently marketed with increased risk of LQTS and TdP. Some non-limiting examples are presented below:

Aloxi or palonasitron HCL: 5-hydroxytryptamine-3 receptor antagonist, an intravenous drug for post-operative nausea and vomiting.(Eisai Corp. Helsinn, Switz.) AE's include >2% EKG, 5% QT prolongation, 4% bradycardia, at doses above 2.25 mg.

Amiodarone (cordorone X) a Class III antiarrhythmic agent, for WPW syndrome, for ventricular arrhythmias: Females>males risk regarded as low. 1-3% have predominantly Class III effects. SA node dysfunction, and enhanced cardiac arrhythmias. MOA is prolongation of myocardial cell—action potential duration, and refractory period, a 10% increase in QT intervals associated with worsening of arrhythmias and TdP, and noncompetitive α- and β-adrenergic inhibition. QTc prolongation with and without TdP with concomitant administration of fluoroquinolones, macrolide antibiotics or azoles. TEVA Pharmaceuticals IND.Ltd.

Arsenic trioxide: an ineffective hERG blocker($IC_{50}$>300 uM), may have an indirect effect on hERG current, an anti-cancer drug. The manufacturer is Cephalon, Inc.

Astemizole*: a second generation histamine H1 and H3 receptor antagonist, and antmalarial marketed by Janssen. Structurally similar to terfenidine and haloperidol. Originally used for allergic rhinitis: no longer available in U.S. because of rare but fatal arrhythmias. $IC_{50}$ is 50 nM hERG tail current.

Bepridil: is a low potency long-acting calcium channel blocking agent(EC50 is 10 uM). Both K+ channels are sensitive targets to calcium channel blockers. It blocks the rapid component hERG in a concentration-dependent manner (EC50 is 0.55 uM) and also inhibits the KvLQT1/IsK K+ channel which generates the slow components of the cardiac delayed rectifier K+ current. These changes can lead to long QT. It is also a calmodulum antagonist with significant anti-effort associated angina, and antihypertensive activity. Manufacturer TOCRIS Bioscience Inc.

Chloroquine: antimalarial: Novartis Pharma AG. Inhibits hERG channels in a concentration and time manner. The half maximal inhibitory concentration ($IC_{50}$) 2.5 uM.

Chlorpheniramine: a low potency first generation antihistamine H1 blocker, which induces QT prolongation, i.e., a hERG blocker in a concentration dependent manner. It affects the channels in the activated and inactivated states but not in the closed states. Overdose of first and second generation antihistamines exert arrhythmic effects by affecting k+ currents.

Chlorpromazine (Thorazine): anti-psychotic/antiemetic/schizophrenia developed by Rhone-Poulec in 1950. It causes cardiac arrhythmias (Fowler NO 1976).

Cisapride: used as gastroprokinetic agent by Janssen Inc.: It was withdrawn in 2000 due to its Long QT side effect (Layton D 2003).

Celaxa (citalopram) a QT prolonger Forest Labs: A selective serotonin reuptake inhibitor (SSRI) which prolongs the QTc interval via direct blockade of the potassium hERG channel, disrupts hERG protein expression in the cell membrane effectively decreasing the number of hERG potassium channels and blocks the I-type calcium current leading to prolonged depolarization. (Witchel, et al).

Clarithromycin and Erythromycin: Antibiotics, females are more sensitive than males. Both cause QT prolongation and TdP. Erythromycin reductes hERG current in a concentration dependent manner with an $IC_{50}$ of 38.9, and clarithromycin 45.7 uM at clinically relevant concentrations.

Curcumin (diferuloylmethane): Inhibits hERG current (Moha ou Maati H, 2008). Curcumin at $IC_{50}$ of 3.5 uM is a moderate potency molecule (Katchman A N, 2005).

Disopyramide: A class 1 antiarrythmic drug (Vaughan Williams Classification) associated with acquired LQTS. Prolongs the QT interval and widens the QRS complex QT in a dose dependent fashion ($IC_{50}$ 7.23 uM). Blocks both sodium and potassium channels depresses phase "O" depolarization and prolongs duration of action potential of normal cardiac cells in atrial and ventricular tissues.

Dofetilide: A Class III antiarrhythmic agent marked by Pfizer as Tikosyn oral capsules used for maintenance of sinus rhythm and atrial fibrillation. Selectively blocks IKr, the delayed rectifier outward potassium current. TdP is a serious side effect with a dose related incidence of 0.3-10.5%. This is a twofold increase in death risk if pre-treatment QTc is greater than 479 ms. A high potency hERG blocker: $IC_{50}$ is 10 nM.

Domperidone: An antidopaminergic drug used as an antinausea agent. By Janssen Pharmaceuticals, not available in the U.S. Associated with cardiac arrest and arrhythmias, and increased QT prolongations in neonates (Djeddi D 2008).

Doxorubicin: 30 uM prolongs QTc by 13%; causes acute QT prolongation without significantly blocking hERG channels but inhibits IKs ($IC_{50}$: 4.78 uM).

Dronedarone: A non-iodinated analogue of amiodarone. (blocks hERG at $IC_{50}$ of 70 nM), used for over 40,000 patients with atrial fibrillation. Wild type hERG tails measured at −40 mV following activation at +30 mV were blocked with $IC_{50}$ values of 59 nM. hERG inhibition followed channel gating, with block developing on membrane depolarization independent of channel activation High external [K+] (94 mM) reduced potency of I(hERG) inhibition and is independent of Y652 and F656 aromatic acid residues. Manufactured by Chemsky (Shanghai) International, and Sanofi-Avantis Inc as (Muttag). The UK NIH blocked this drug in 2010 based upon cost.

Droperidol: A central sedative, anti-nausea, anesthesia adjunct, Associated with prolongation of the QT interval, TdP and sudden death. hERG tail currents following test pulses to 50 mV were inhibited with an $IC_{50}$ of 77.3 nM. hERG channels were affected in their open and inactivated states. Potency was decreased with mutation of Phe-656 to thr or Ser-631 to Ala. Fourteen companies are listed for this compound.

Grepafloxacin: An oral fluoroquinolone antibiotic caused a number of severe cardiovascular events including PQTS and was voluntarily withdrawn from the market. (WHO 1999).

Haldol, Haloperidol: A high potency hERG blocker, antipsychotic schizophrenia, agitation, when given intravenously or at higher than recommended doses, risk of sudden death, QT prolongation and TdP increases. Janssen-Silag Ltd.

Halofantrine: Antimalarial, associated with cardiac arrhythmias and significant QT prolongation.females more sensitive than males. Glaxo-Smith-Kline.

Ibutilide: Corvert by Pfizer, a pure class III antiarrythmic for atrial flutter and fibrillation, females more sensitive than males. Induces slow inward sodium current. Does not block K current, but prolongs action potential.

Levomethadyl: Opiate agonist/pain control, narcotic dependence. Similar to methadone. Roxanne Labs removed from market because of ventricular rhythm disorders.

Lidoflazine: A piperazine calcium channel blocker with anti-arrhythmic activity. high potency hERG blocker ($IC_{50}$ of 16 nM) of the alpha sub-unit of the potassium channel. Preferentially inhibits open activated channels. 13 fold more potent than Verapamil against hERG.

Loratidine, Claritin: A second generation antihistamine, a hERG blocker at an $IC_{50}$ of 173 nM. may have an indirect effect on hERG repolarization current. Marked by Schering-Plough.

Lovostatin: A low-potency hERG blocker synthetic.

Mesoridazone: Antipsychotic schizophrenia.

Methadone: Interacts with the voltage—gated myocardial potassium channels in a concentration dependent manner causing serious cardiac arrhythmias, and deaths from TdP and ventricular fibrillation in patients taking methadone. $IC_{50}$ is 4.8 uM (compared with 427 uM for heroin) an antidopaminergic drug. Methadone related predispositions to TdP are female, high dosages, CYP2 B6 slow metabolizer of S-methadone and DNA polymorphisms. Parenterol methadone and chlorobutanol combinations are contraindicated. QT prolonging activity is mainly due to S-methadone which blocks hERG current 3-5 fold more potently than R-methadone.

Methanesulphonanilide (E-4031): An extremely high potency compound, inhibits hERG at nM concentrations. Used as positive control in standard assays.

Moxifloxacin: A hERG channel blocker: at 100 uM prolonged QTc by 22% not prevented by dexrazoxane.

Pentamidine: An ineffective hERG blocker ($IC_{50}$>300 uM), anti-infective, pneumocystis pneumonia. Associated with QT interval lengthening and TdP, hence may have an unknown indirect effect on hERG repolarization.

Pimozide: Antipsychotic, Tourette's tics.

Prenylamine: A moderate hERG blocker.

Probucol: Antilipemic, anticholesterolemic, no longer available in the U.S.

Procainamide: Anti-arrythmic.

Propafenone: A low-potency hERG blocker($IC_{50}$>1 uM).

Pyrilamine: A low potency hERG blocker.

Quinidine: Anti-arrythmic females>males.

Seldane (Terfenidine): A high potency hERG blocker.

Sertindole: A moderate potency hERG blocker.

Sotalol: A LQT2 model, action is prevented by nicorandil a potassium channel opener. It can act as an antiarrythmic, β-blocker for ventricular tachycardia, atrial fibrillation (DucroqJ 2005). Two (2) % of 1288 patients exhibited QT prolongation, and a QTc greater than 455 ms lead to TdP.

Sparfloxacin: Antibiotic.

Thioridazine: A moderate potency hERG blocker.

Vandetanib: An oral kinase inhibitor marketed by AstraZeneca is approved for progressive metastatic or locally advanced medullary thyroid cancer. QT prolongation, TdP and sudden death are included in a boxed warning. The most common (>5%) grade ¾ adverse reactions include QT prolongation fatigue and rash.

Terfenadine an antihistamine prodrug for the active form fexofenadine, and E-4031 were selected as a reference compounds for this study. Terfenadine has reported ventricular arrhythmias cardiotoxic effects, particularly if taken in combination with macrolide antibiotics or ketoconazole. An $IC_{50}$ hERG inhibitory effect value of 99 nM was calculated from data obtained in the same cell line as that used for the test article in this study. E-4031, a Class III antiarrhythmic drug is a synthetic toxin used solely for research purposes with one clinical exception (Okada Y., 1996). Its mechanism of action is to block the hERG voltage-gated potassium channels. At 100 nM E-4031 inhibited 90.6% of the current density. The inhibitions observed are in line with internal validation data generated in identical conditions, and agree with published inhibition values for this compound. These results confirm the sensitivity of the test system to hERG-selective inhibitors, in this case, Terfenadine and E-4031.

The effect of Curcumin on whole-cell IKr hERG currents: whole-cell currents elicited during a voltage pulse were recorded in baseline conditions, following the application of the selected concentrations of curcumin and following a washout period. As per protocol, 4 concentrations of curcumin were analyzed for hERG current inhibition. The cells were depolarized for one second from the holding potential (−80 mV) to a maximum value of +40 mV, starting at −40 mV and progressing in 10 mV increments. The membrane potential was then repolarized to −55 mV for one second, and finally returned to −80 mV.

Whole-cell tail current amplitude was measured at a holding potential of −55 mV, following activation of the current from −40 to +40 mV. Current amplitude was measured at the maximum (peak) of this tail current. Current density was obtained by dividing current amplitude by cell capacitance measured prior to capacitive transient minimization.

Current run-down and solvent effect correction: all data points have been corrected for solvent effect and time-dependent current run-down. Current run-down and solvent effects were measured simultaneously by applying the experimental design in test-article free conditions (DMSO) over the same time frame as was done with the test article. The loss in current amplitude measured during these so-called vehicle experiments (representing both solvent effects and time-dependent run-down) was subtracted from the loss of amplitude measured in the presence of the test article to isolate the effect of the test article, apart from the effect of the solvent and the inevitable run-down in current amplitude over time.

The study presented herein quantified the effect of curcumin solubilized in DMSO on IKr. The concentrations of curcumin (0.014, 0.2, 3.4 and 11.4 µM) were based on information available at the time of the design of this study. The concentrations were selected based on: (1) the predicted human plasma levels at the planned lowest Phase 1 dose level; (2) the predicted human plasma concentrations at the planned highest Phase 1 dose level; (3) 30-fold over the predicted human therapeutic plasma levels; and (4) 100-fold over the predicted human therapeutic plasma levels. These selected concentrations are considered to provide valuable predictions of the effect of curcumin on human cardiac electrophysiology. Curcumin 99.2% pure, was synthesized under GMP conditions in Sami Labs, Bangalore, India and stored at 4° C. in the absence of light. One mL aliquot of each curcumin concentration used to expose the cells included in this study were independently analyzed for curcumin content. For the subsequent studies GMP grade liposomal curcumin was formulated at Polymun GmbH, Vienna Austria, and stored at 4° C. The liposomes were obtained from Polymun GmbH, terfenadine and E04031 were purchased from Sigma Aldrich Fine Chemicals.

TABLE 1

Effect of terfenadine, a positive control on hERG current density from transfected HEK 293 cells at 20 mV.

| | Normalized Current Density | Corrected Normalized Current Density | SEM | p value | n = |
|---|---|---|---|---|---|
| Baseline | 1.000 | 1.000 | n/a | n/a | 3 |
| Terfenadine, 0.01 µM* | 0.645 | 0.767 | 0.090 | 0.122 | 3 |
| Terfenadine, 0.03 µM** | 0.650 | 0.772 | 0.073 | 0.088 | 3 |
| Terfenadine, 0.1 µM** | 0.362 | 0.483* | 0.063 | 0.015 | 3 |

*10 nM,
**30 nM,
***100 nM.
Terfenadine inhibited IKr with an $IC_{50}$ of 0.065 umolar (65 nM) potency.

TABLE 2

Effect of Terfenadine on hERG current density from transfected HEK 293 cells at 20 mV.

| | Normalized Current Density | Corrected Normalized Current Density | SEM | p value | n = |
|---|---|---|---|---|---|
| Baseline | 1.000 | 1.000 | n/a | n/a | 3 |
| Terfenadine, 30 nM | 0.469 | 0.548 | 0.080 | 0.111 | 2 |
| Terfenadine, 100 nM | 0.399 | 0.478* | 0.072 | 0.018 | 3 |
| Terfenadine, 300 nM | 0.043 | 0.122* | 0.004 | 0.000 | 3 |

*The current recorded after exposure to the test article concentration was statistically different from the current recorded in baseline condition. Difference was considered statistically significant when p ≤ 0.05.

Figure 2:
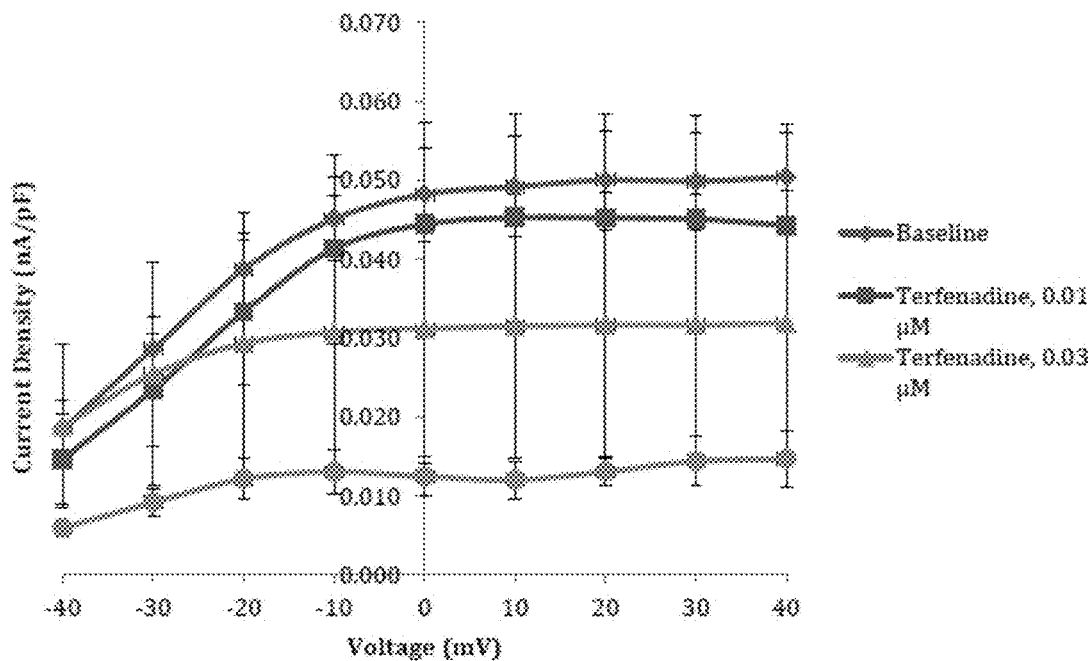
FIG. 2 is a graph that shows the current-voltage (I-V) relationship of hERG current amplitude from transfected HEK 293 cells exposed to terfenadine.
Figure 3:
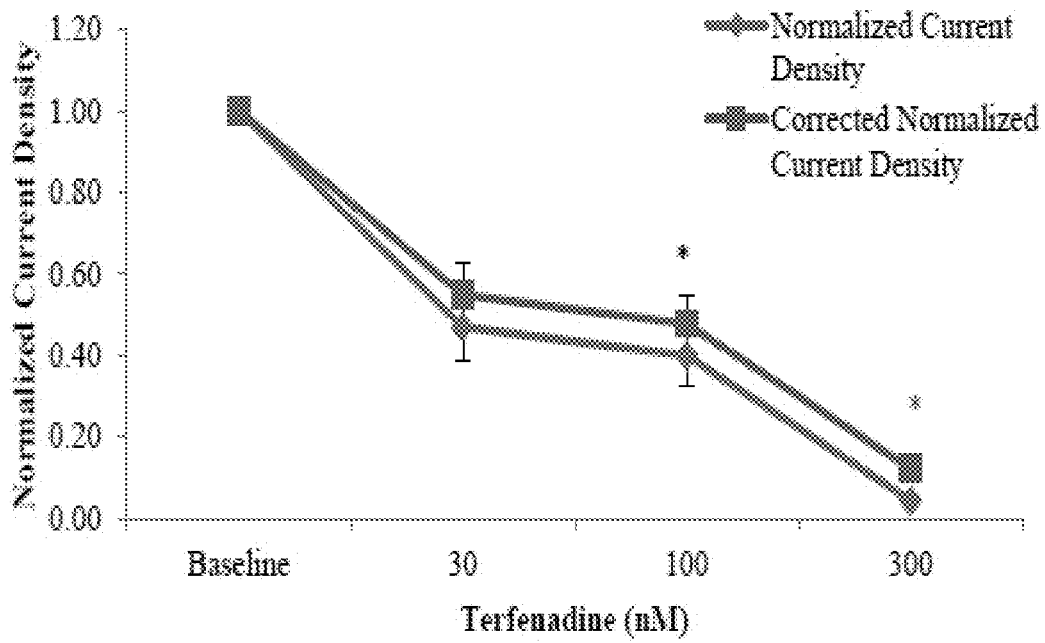
FIG. 3 is a graph that shows the effect of terfenadine on hERG current density from transfected HEK 293 cells at 20 mV.
Figure 4:
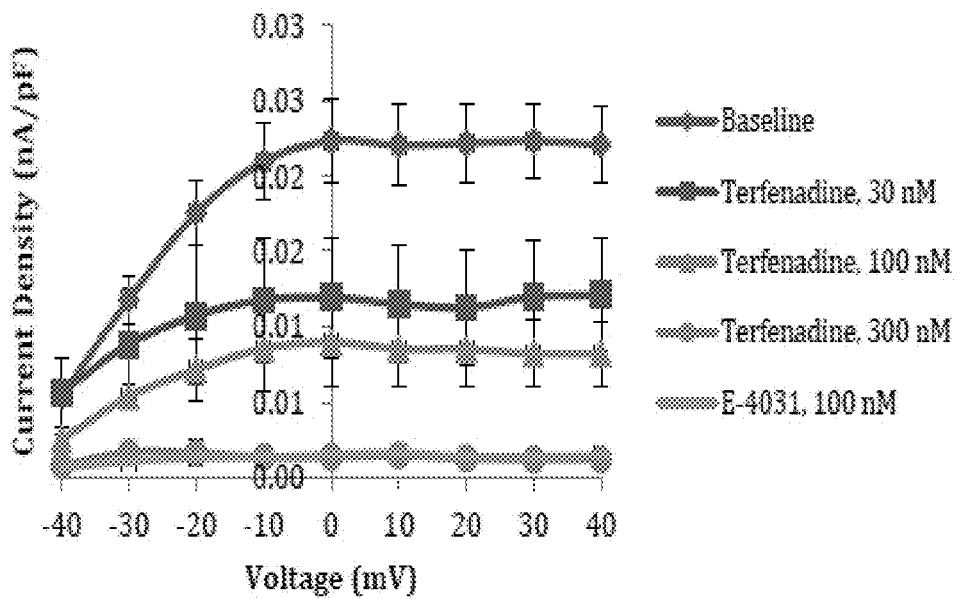
FIG. 4 is a graph that shows the I-V relationship of hERG current amplitude from transfected HEK 293 cells exposed to terfenadine.

FIG. 1 is a graphical representation of the data presented in Table 2. FIG. 2 is a graph of the current-voltage (I-V) relationship of hERG current amplitude from transfected HEK 293 cells exposed to terfenadine. FIG. 3 is a graph of the effect of terfenadine on hERG current density from transfected HEK 293 cells at 20 mV. FIG. 4 is a graph of the I-V relationship of hERG current amplitude from transfected HEK 293 cells exposed to terfenadine.

TABLE 3

Effect of E-4031 on hERG current density from transfected HEK 293 cells at 20 mV.

| | Normalized Current Density | Corrected Normalized Current Density | SEM | p value | n = |
|---|---|---|---|---|---|
| Baseline | 1.000 | 1.000 | n/a | n/a | 3 |
| E-4031, 100 nM | 0.124 | 0.094* | 0.067 | 0.0055 | 3 |

Figure 5:
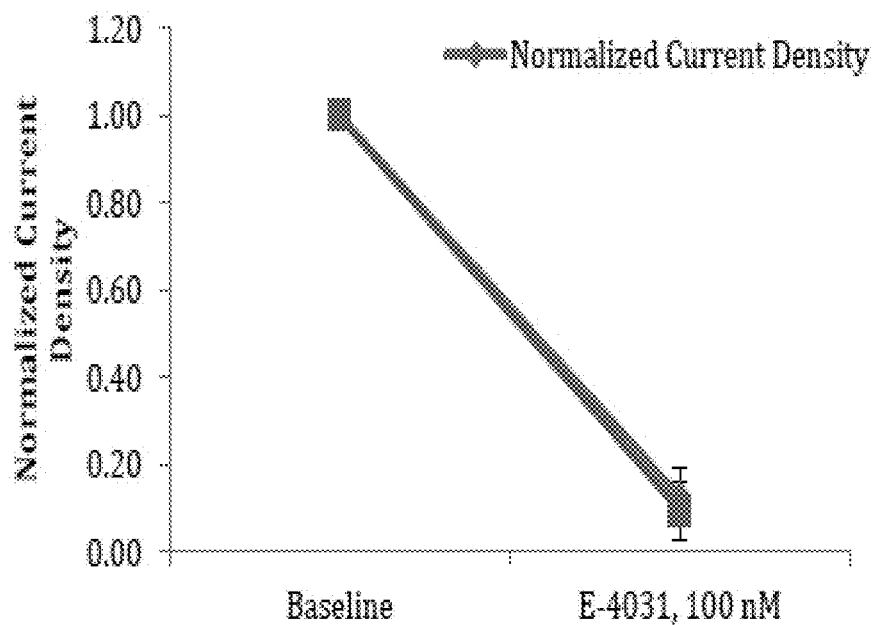
FIG. 5 is a graph that shows the effect of E-4031 on hERG current density from transfected HEK 293 cells at 20 mV.

E-4031 inhibited IKr with an IC50 of 50 nM. FIG. 5 is a graph showing the effect of E-4031 on hERG current density from transfected HEK 293 cells at 20 mV.

TABLE 4

Effect of Curcumin on hERG current density from transfected HEK 293 cells at 20 mV.

| | Normalized Current Density | Corrected Normalized Current Density | SEM | p value | n = |
|---|---|---|---|---|---|
| Baseline | 1.000 | 1.000 | n/a | n/a | 7 |
| Curcumin, 0.014 µM | 0.892 | 0.862 | 0.084 | 0.1521 | 7 |
| Curcumin, 0.2 µM | 0.773 | 0.744* | 0.070 | 0.0107 | 7 |
| Curcumin, 3.4 µM | 0.642 | 0.612* | 0.095 | 0.0064 | 7 |

TABLE 4-continued

Effect of Curcumin on hERG current density from transfected HEK 293 cells at 20 mV.

| | Normalized Current Density | Corrected Normalized Current Density | SEM | p value | n = |
|---|---|---|---|---|---|
| Curcumin, 11.4 µM | 0.234 | 0.204* | 0.016 | 0.0000 | 7 |
| Washout | 0.489 | 0.459 | 0.127 | 0.2036 | 3 |

Figure 6:
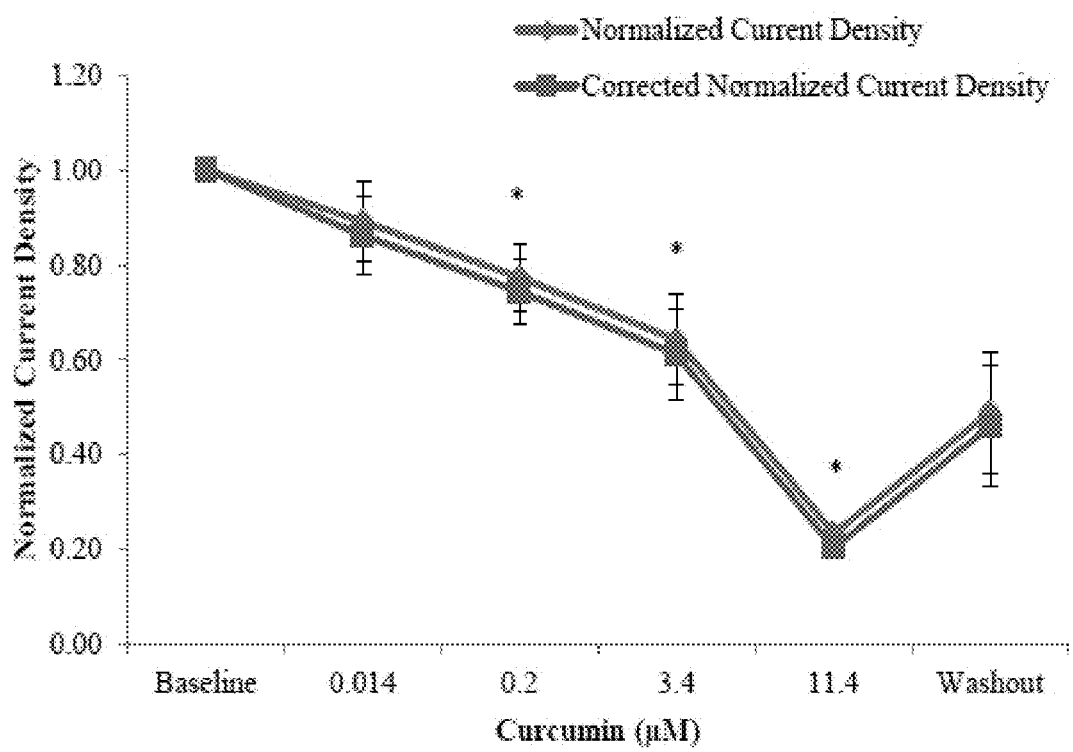
FIG. 6 is a graph that shows the effect of curcumin on hERG current density from transfected HEK 293 cells at 20 mV.
Figure 7:
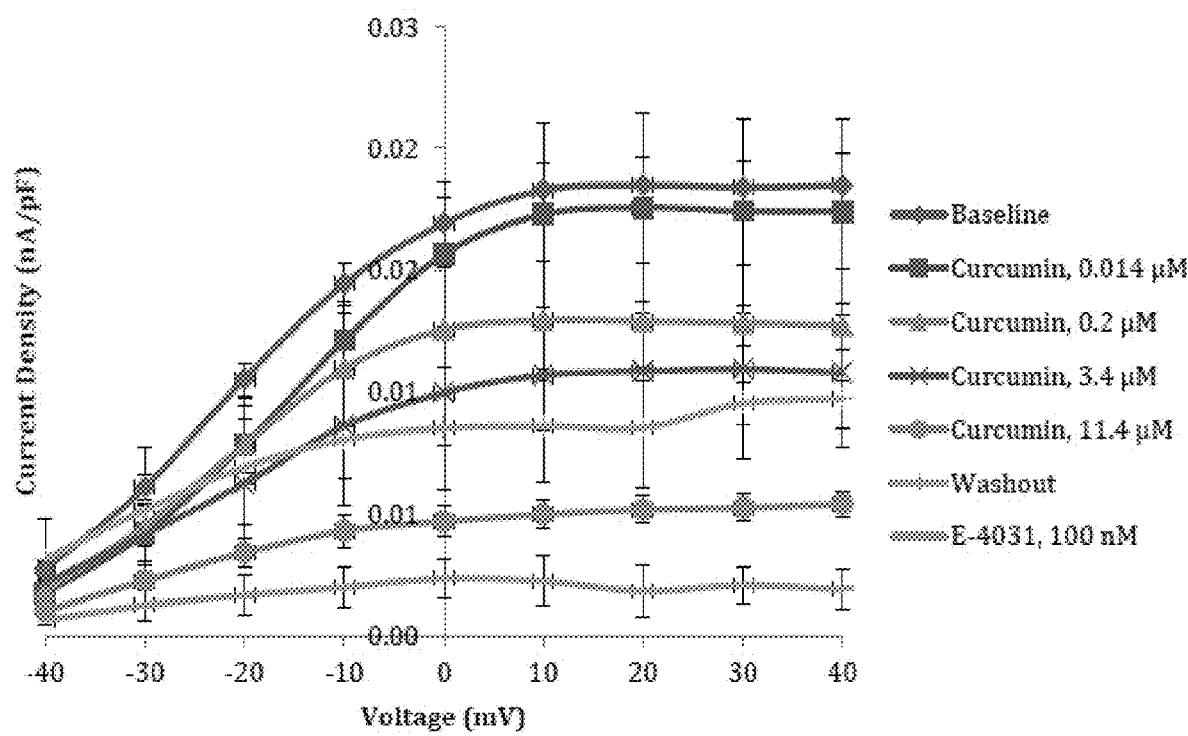
FIG. 7 is a graph that shows the I-V relationship of hERG current amplitude from transfected HEK 293 cells exposed to curcumin.

At a concentration of 11.4 µM curcumin caused 79.6% inhibition of the hERG tail current density at 1+20 (n=7). Paired student's t-tests confirmed that the difference in normalized current density measured at baseline and in the presence of 0.2 to 11.4 µM of curcumin reached the selected threshold for statistical significance (p 0.05). Table 3 provides p-values obtained from statistical analysis. Fifty percent inhibition of the current was achieved within the range of concentrations (0.014 to 11.4 µM) selected for this study. An $IC_{50}$ value of 4.9 µM was calculated from the data obtained. FIG. 6 is a graph of data shown in Table 4. FIG. 7 is a graph of the I-V relationship of hERG current amplitude from transfected HEK 293 cells exposed to curcumin.

TABLE 5

Effect of Curcumin (as liposomal curcumin) on hERG current density from transfected HEK 293 cells at 20 mV.

| | Normalized Current Density | Corrected Normalized Current Density | SEM | p value | n = |
|---|---|---|---|---|---|
| Baseline | 1.000 | 1.000 | n/a | n/a | 7 |
| Curcumin (liposomal curcumin), (0.014 µM) | 0.854 | 0.934 | 0.039 | 0.142 | 7 |
| Curcumin (liposomal curcumin), (0.2 µM) | 0.838 | 0.918 | 0.092 | 0.408 | 7 |
| Curcumin (liposomal curcumin), (3.4 µM) | 0.769 | 0.848 | 0.072 | 0.079 | 7 |
| Curcumin (liposomal curcumin), (11.4 µM) | 0.716 | 0.795* | 0.082 | 0.046 | 7 |
| Washout | 0.474 | 0.554* | 0.101 | 0.020 | 4 |

P-values obtained from statistical analysis indicates borderline significant differences of current density from baseline at 11.4 uM, however the extent of current inhibition was less than the $IC_{50}$.

Figure 8:
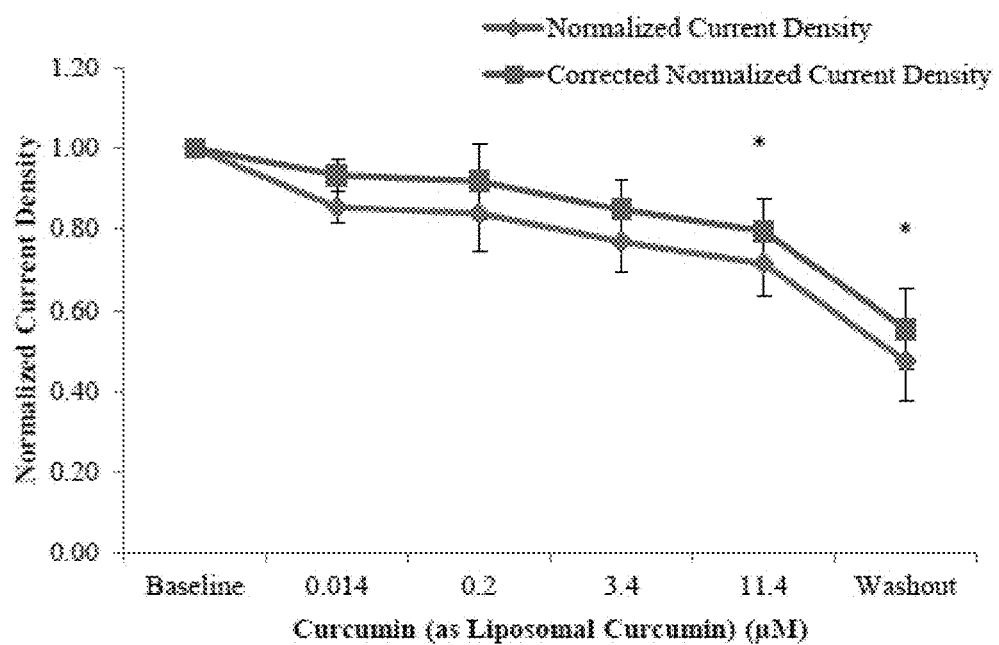
FIG. 8 is a graph that shows the effect of curcumin (as liposomal curcumin) on hERG current density from transfected HEK 293 cells at 20 mV.
Figure 9:
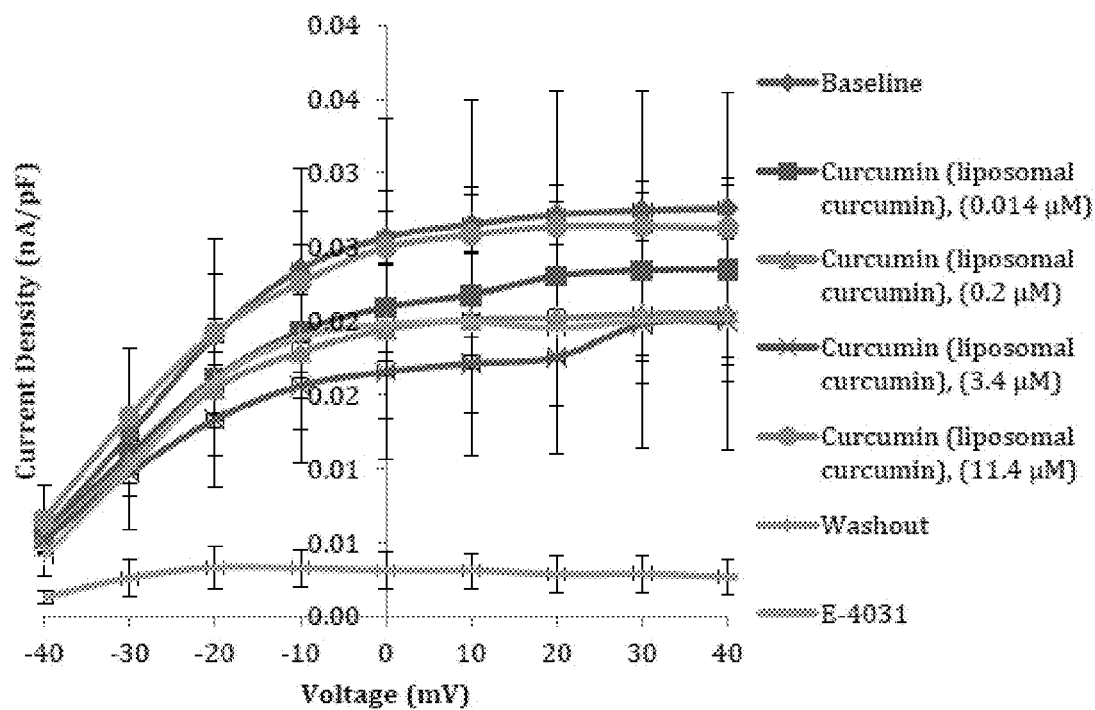
FIG. 9 is a graph that shows the I-V relationship of hERG current amplitude from transfected HEK 293 cells exposed to Curcumin (as liposomal curcumin)

FIG. 8 is a graph showing the effect of curcumin (as liposomal curcumin) on hERG current density from transfected HEK 293 cells at 20 mV and FIG. 9 is a graph showing the I-V relationship of hERG current amplitude from transfected HEK 293 cells exposed to Curcumin (as liposomal curcumin).

In Table 5 the rectifying inward current showed that the inhibition effect of curcumin on the hERG tail current is voltage dependent with higher potency at positive holding potentials. The currents recorded after washout were compared statistically to the currents recorded after the highest concentration of Curcumin (liposomal curcumin) (11.4 µM).

TABLE 6

Effect of empty liposome vortexed with curcumin on hERG current density from transfected HEK 293 cells at 20 mV.

| | Normalized Current Density | Corrected Normalized Current Density | SEM | p value | n = |
|---|---|---|---|---|---|
| Baseline | 1.000 | 1.000 | n/a | n/a | 3 |
| Curcumin (Lipo-Curc.), 0.2 μM | 0.937 | 0.994 | 0.073 | 0.946 | 3 |
| Curcumin (Lipo-Curc.), 3.4 μM | 0.738 | 0.796 | 0.055 | 0.064 | 3 |
| Curcumin (Lipo-Curc.), 11.4 μM | 0.498 | 0.555 | 0.119 | 0.064 | 3 |
| Washout | 0.479 | 0.536 | 0.145 | 0.899 | 3 |

Liposome concentration was 0.7,12,41 ng/ml. No significant difference from curcumin at any dose level.

Figure 10:
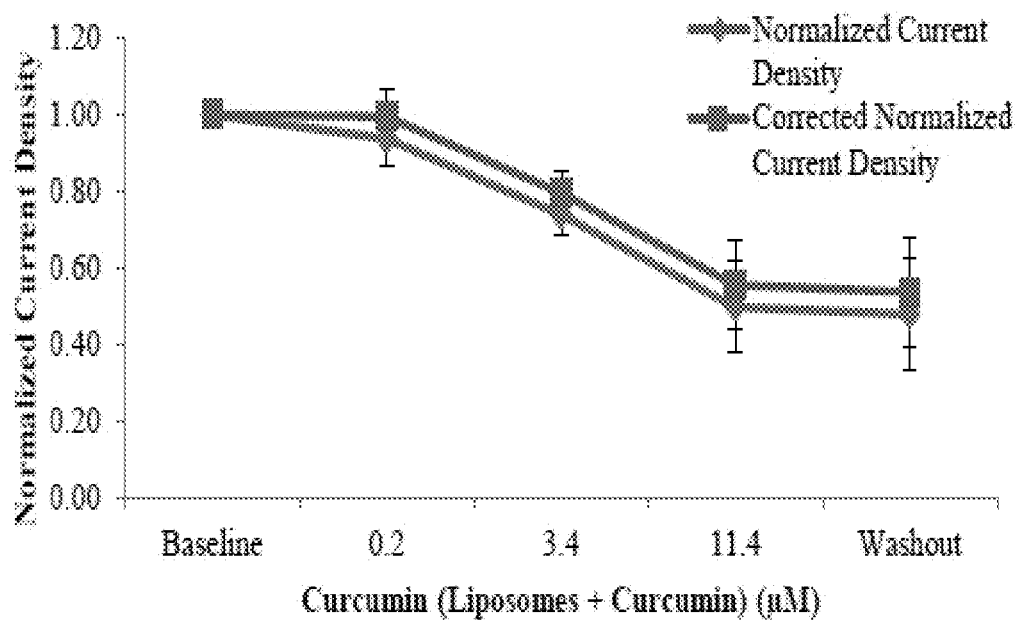
FIG. 10 is a graph that shows the effect of Curcumin (Liposomes+Curcumin) on hERG current density from transfected HEK 293 cells at 20 mV.
Figure 11:
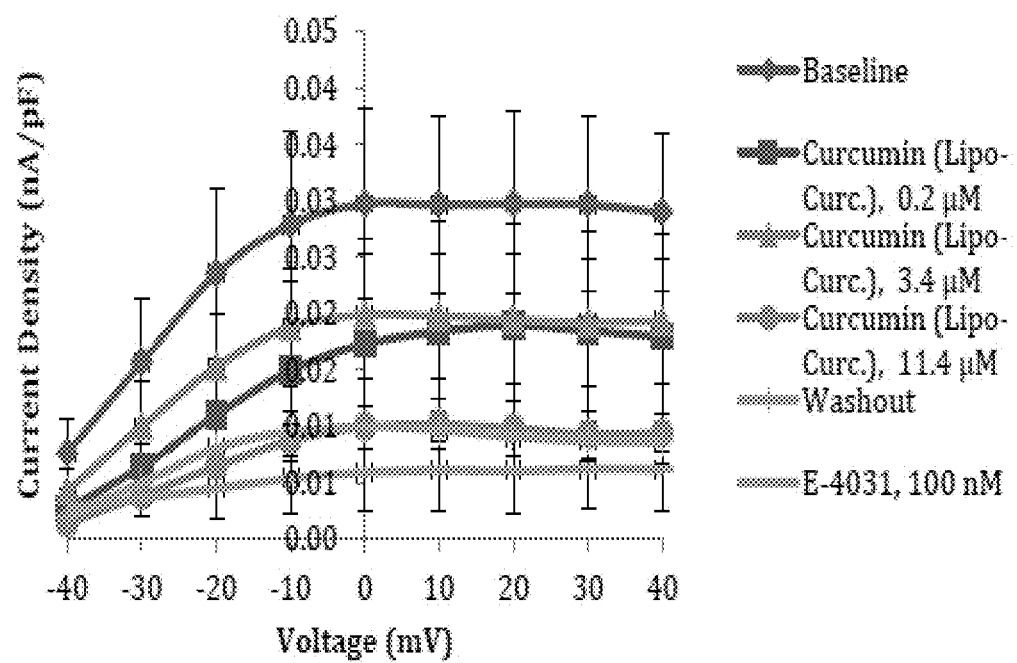
FIG. 11 is a graph that shows the I-V relationship of hERG current amplitude from transfected HEK 293 cells exposed to Curcumin (Liposomes+Curcumin)

FIG. 10 is a graph showing the effect of Curcumin (Liposomes+Curcumin) on hERG current density from transfected HEK 293 cells at 20 mV, and FIG. 11 is a graph of the I-V relationship of hERG current amplitude from transfected HEK 293 cells exposed to Curcumin (Liposomes+Curcumin). The current recorded after washout was compared and similar statistically to the currents recorded after the highest concentration of curcumin at 11.4 uM. The current $IC_{50}$ was not reached.

TABLE 7

Effect of Liposomes on hERG current density from transfected HEK 293 cells at 20 mV.

| | Normalized Current Density | Corrected Normalized Current Density | SEM | p value | n = |
|---|---|---|---|---|---|
| Baseline | 1.000 | 1.000 | n/a | n/a | 3 |
| Liposome, 0.7227 ng/mL | 0.921 | 1.041 | 0.037 | 0.379 | 3 |
| Liposome, 12.285 ng/mL | 0.805 | 0.926 | 0.065 | 0.374 | 3 |
| Liposome, 41.193 ng/mL | 0.888 | 1.009 | 0.075 | 0.919 | 3 |
| Washout | 0.817 | 0.938 | 0.151 | 0.734 | 3 |

Figure 12:
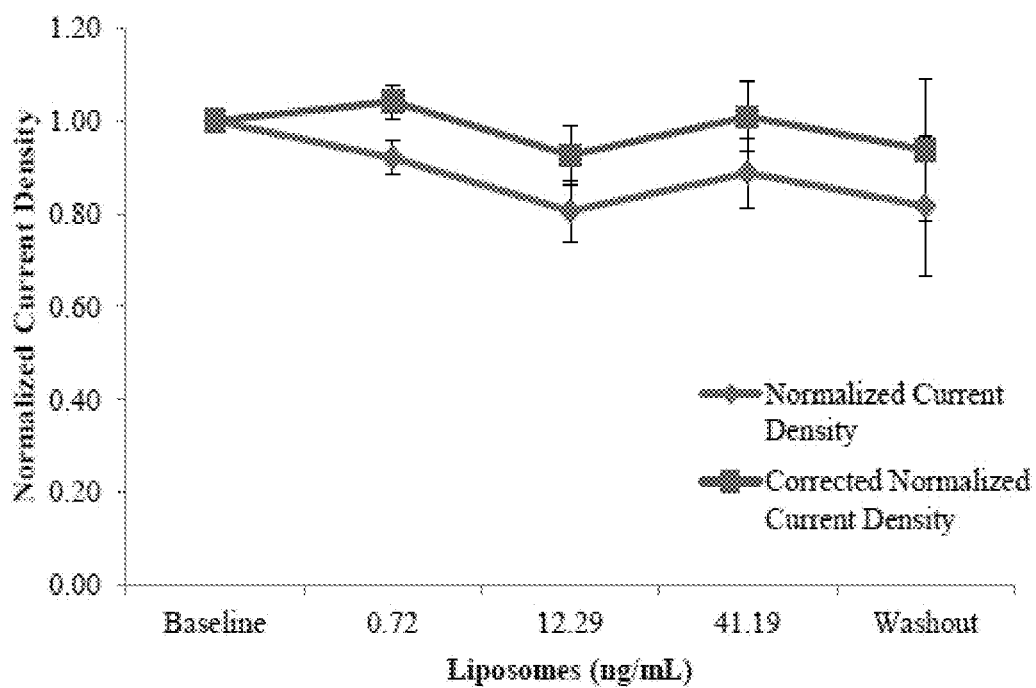
FIG. 12 is a graph that shows the effect of liposomes on hERG current density from transfected HEK 293 cells at 20 mV.
Figure 13:
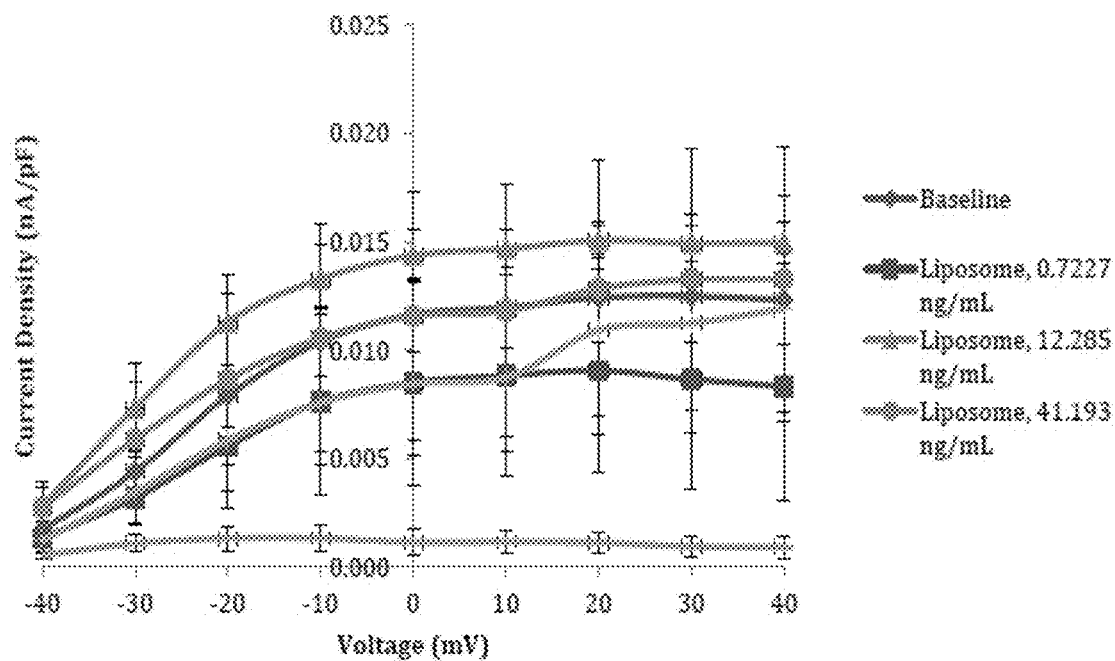
FIG. 13 is a graph that shows the I-V relationship of hERG current amplitude from transfected HEK 293 cells exposed to liposomes.

Liposomes do not exhibit an inhibitory effect on the in vitro hERG channel. The current recorded after washout was comparable statistically to the currents recorded after the highest concentration of Liposomes (41.193 ng/mL). FIG. 12 is a graph of the data presented in Table 7, and FIG. 13 is a graph of the I-V relationship of hERG current amplitude from transfected HEK 293 cells exposed to liposomes.

TABLE 8

Effect of Liposomes + E-4031 on hERG current density from transfected HEK 293 cells at 20 mV.

| | Normalized Current Density | Corrected Normalized Current Density | SEM | p value | n = |
|---|---|---|---|---|---|
| Baseline | 1.000 | 1.000 | n/a | n/a | 3 |
| Liposome, 0.72 ng/mL + E-4031, 30 nM | 0.489 | 0.610 | 0.115 | 0.077 | 3 |
| Liposome, 12.29 ng/mL + E-4031, 100 nM | 0.219 | 0.339* | 0.067 | 0.010 | 3 |
| Liposome, 41.19 ng/mL + E-4031, 300 nM | 0.171 | 0.292* | 0.022 | 0.001 | 3 |
| Washout | 0.130 | 0.251 | 0.037 | 0.675 | 2 |

*the current recorded after exposure to the test article concentration was statistically different p ≤ 0.05 from the current recorded in baseline condition.

Figure 14:
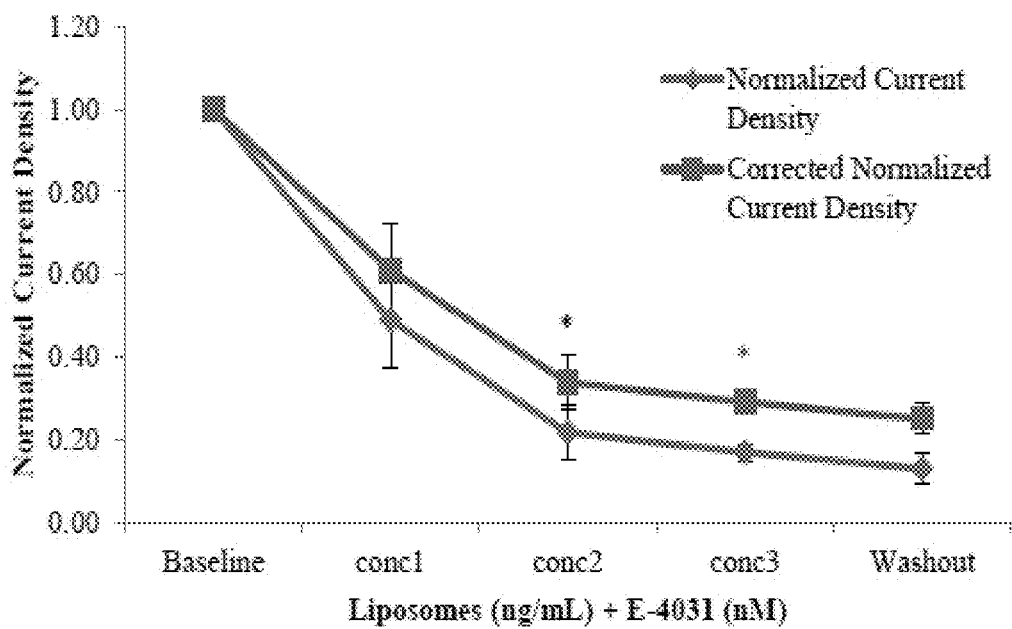
FIG. 14 is a graph that shows the of liposomes+E-4031 on hERG current density from transfected HEK 293 cells at 20 mV.
Figure 15:
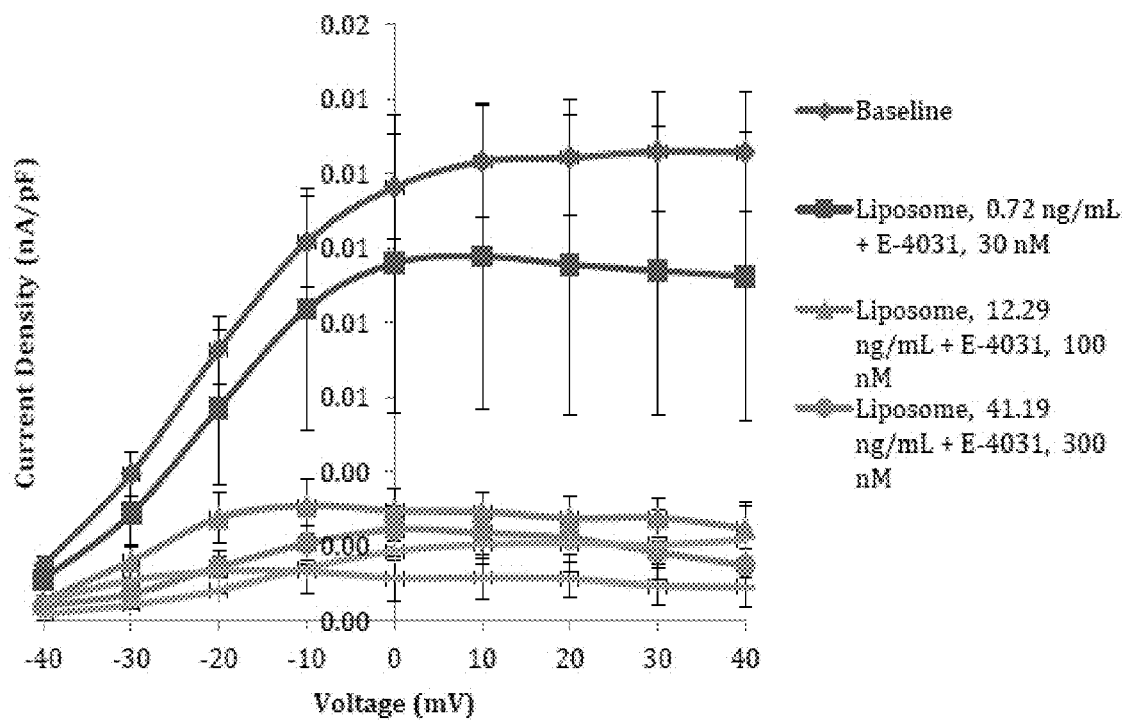
FIG. 15 is a graph that shows the I-V relationship of hERG current amplitude from transfected HEK 293 cells exposed to Liposomes+E-4031.

FIG. 14 is a graph showing the effect of liposomes+E-4031 on hERG current density from transfected HEK 293 cells at 20 mV. FIG. 15 is a graph of the I-V relationship of hERG current amplitude from transfected HEK 293 cells exposed to Liposomes+E-4031.

Empty Liposomes when vortexed with E-4031 at 30-300 nM concentrations do not prohibit the anti-hERG effect of E-4031. E-4031 inhibition. The current recorded after washout was compared statistically to the currents recorded after the highest concentration of Liposomes+E-4031.

TABLE 9

Effect of Liposomes + Terfenadine on hERG current density from transfected HEK 293 cells at 20 mV.

| | Normalized Current Density | Corrected Normalized Current Density | SEM | p value | n = |
|---|---|---|---|---|---|
| Baseline | 1.000 | 1.000 | n/a | n/a | 3 |
| Terfenadine (Liposome + Terfenadine), 30 nM | 0.298 | 0.392* | 0.065 | 0.011 | 3 |
| Terfenadine (Liposome + Terfenadine), 100 nM | 0.122 | 0.216* | 0.073 | 0.008 | 3 |
| Terfenadine (Liposome + Terfenadine), 300 nM | 0.117 | 0.211* | 0.032 | 0.000 | 4 |
| Washout | 0.276 | 0.369 | 0.017 | 0.081 | 2 |

*Mean that the current recorded after exposure to the test article concentration was statistically different from the current recorded in baseline condition. Difference was considered statistically significant when p ≤ 0.05.

Figure 16:
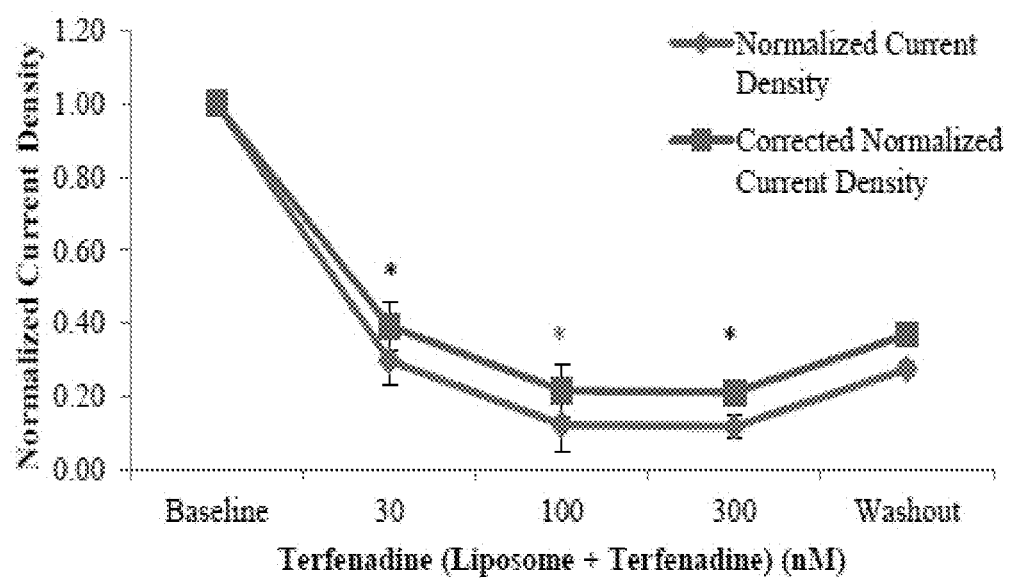
FIG. 16 is a graph that shows the effect of liposomes+terfenadine on hERG current density from transfected HEK 293 cells at 20 mV.
Figure 17:
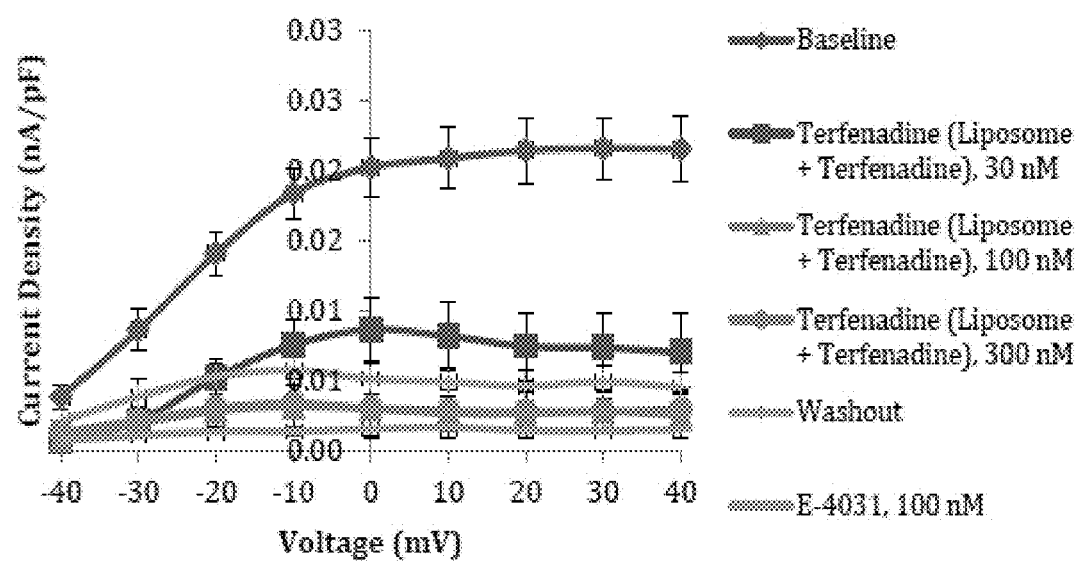
FIG. 17 is a graph that shows the I-V relationship of hERG current amplitude from transfected HEK 293 cells exposed to liposomes+terfenadine.

The data presented in Table 9 hereinabove is represented graphically in FIG. 16, and FIG. 17 is a graph showing the I-V relationship of hERG current amplitude from transfected HEK 293 cells exposed to liposomes+terfenadine. There was no effect of empty liposomes when vortexed with Terfenadine at 30-300 nM the Terfenadine inhibition of hERG current density.

The data presented hereinabove suggest that curcumin, within the range of concentrations tested and in the specific context of this study down-modulates the IKr current, i.e., it interacts with the proteins encoded by the hERG gene and activates channel gating functions decreasing ion flow. A similar observation with a curcuminoid mixture (78% curcumin) was published (Moha ou Matti, 2008). These data support their initial observation, and emphasize that the curcumin (diferuloylmethane) molecule exhibits the predominant if not all the IKr inhibition.

The findings of the present invention that liposomal curcumin or vortexed mixtures of liposomes with curcumin prohibited IKr down modulation by curcumin allowing normal gating functions to occur suggest that liposome encapsulation of curcumin is not necessary to prevent interactions with channel drug receptor sites. The empty liposome did not appear to interact with the protein encoded by the hERG gene in the absence of curcumin, or in the presence of E-4031 and terfenadine relates to questions regarding the specificity and degree of affinities or preferential interactions of the receptors in the K+ channel (Zachariae U 2009).

Ikr/hERG suppression induced by curcumin is mitigated when the curcumin is incorporated within a liposome or simply vortexed with it prior to exposure. Combined intravenous administration of this liposome and intravenous QT prolonging drugs other than curcumin may mitigate delayed QT in vivo.

EXAMPLE 2

Liposomes Ameliorate Drug-Induced Inhibition of the Cardiac $I_{Kr}$ Channel

Crizotinib (Xalkori®) and nilotinib (Tasigna®) are tyrosine kinase inhibitors approved for the treatment of non-small cell lung cancer and chronic myeloid leukemia, respectively. Both have been shown to result in QT prolongation in humans and animals. Liposomes have been shown to ameliorate drug-induced effects on the $I_{Kr}$ ($K_v11.1$) channel, coded by the human ether-a-go-go-related gene (hERG). A study was conducted to determine if liposomes would also decrease the effect of crizotinib and nilotinib on the $I_{Kr}$ channel. Crizotinib and nilotinib were tested in a standard in vitro $I_{Kr}$ assay using human embryonic kidney (HEK) 293 cells stably transfected with the hERG.ABose-responses were determined and 50% inhibitory concentrations ($IC_{50}$s) were calculated. When the HEK 293 cells were treated with crizotinib and nilotinib that were mixed with liposomes, there was a significant decrease in the $I_{Kr}$ channel inhibitory effects of these two drugs. The use of liposomal encapsulated QT-prolongation agents, or just mixing these drugs with liposomes, may decrease their cardiac liability.

Crizotinib (Xalkori®) is an anaplastic lymphoma kinase (ALK) inhibitor approved for the treatment of non-small cell lung cancer in patients with ALK-positive tumors. Nilotinib (Tasigna®) is a BCR-ABL kinase inhibitor approved for Philadelphia chromosome positive chronic myeloid leukemia. Both drugs inhibit the ion channel responsible for the delayed-rectifier K+ current in the heart ($k_r$, or $K_v11.1$), encoded by the human ether-a-go-go-related gene (hERG) Inhibition of the $I_{Kr}$ channel can result in prolongation of the QTc, which can lead to life-threatening polymorphic ventricular tachycardia, or torsades de pointes (1). Crizotinib causes QT prolongation in humans and animals, whereas nilotinib has only been shown to cause QT prolongation in humans.

$I_{Kr}$ channel inhibition and cardiac toxicity can be a major liability for some classes of drugs. Detection of $I_{Kr}$ channel inhibition and/or in vivo QT prolongation during preclinical drug development can lead to the abandonment of development of promising drugs classes. A number of QT-prolonging drugs have been withdrawn during development or after being on the market. Examples include terfenadine, astemizole, gripafloxacin, terodilene, droperidole, lidoflazine, levomethadyl, sertindoyle and cisapride.

During development, crizotinib was shown to inhibit the $I_{Kr}$ channel with a 50% inhibitory concentrations ($IC_{50}$) of 1.1 µM (2), indicating the potential for prolongation of QT interval. The $IC_{50}$ values were below or similar to the C. seen in humans at clinically-relevant doses. Dogs treated intravenously with crizotinib showed decreased heart rate and contractility, and increased left ventricular end diastolic pressure, and increased PR-, QRS- and QT-intervals (3). These preclinical findings correlate with clinical findings of QTc prolongation, bradycardia and cardiac arrest observed occasionally in clinical trials (3,4). Nilotinib was shown to inhibit the $I_{Kr}$ channel with an $IC_{50}$ of 0.13 µM (5). But, in contrast to crizotinib, dogs treated orally up to 600 mg/kg did not show QT prolongation (5). One difference between the crizotinib and nilotinib dog studies was crizotinib was given intravenously and nilotinib was given orally. As with crizotinib, clinical trials showed an association of therapeutic doses of nilotinib with QTc prolongation (6,7).

A study by Doherty et al (8) found multiple effects of crizotinib and nilotinib on human cardiomyocytes in vitro. These effects included cardiac cell death, increased caspase activation, and increase superoxide generation. Cardiac cell morphology was altered along with disruption of normal beat patterns of individual cardiac cells. For crizotinib, the cardiac ion channels $I_{Kr}$, NaV1.5 and CaV were inhibited with $IC_{50}$s of 1.7, 3.5 and 3.1 µM, respectively. For nilotinib, $IC_{50}$s were 0.7, >3 and >3 µM, respectively.

The present inventors have previously shown that liposomes mitigate curcumin-induced inhibition of the $I_{Kr}$ channel (9). The present study shows the result on the effects of crizotinib and nilotinib on the $I_{Kr}$ channel, and determine if the addition of liposomes will ameliorate these effects.

Figure 18A:
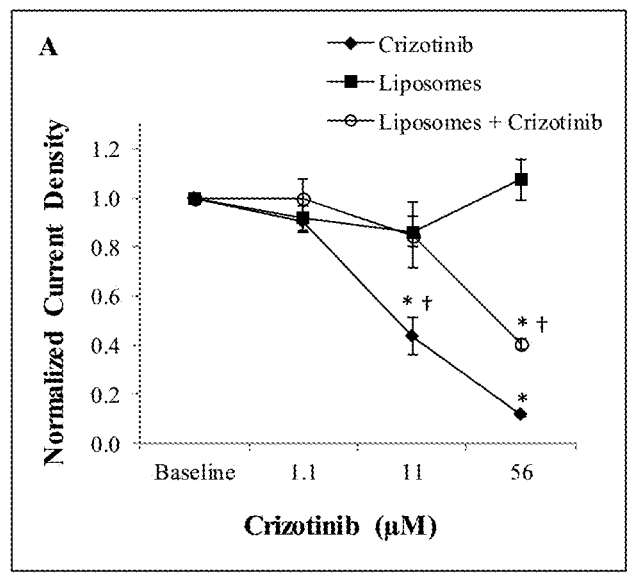
FIGS. 18A and 18B is a graph that shows the IKr tail current density averages and voltage dependency obtained by measuring the IKr tail peak amplitude and in the presence of crizotinib, liposomes alone, and crizotinib plus liposomes.

Crizotinib, at concentrations of 11 and 56 µM, caused 56 and 89% inhibition, respectively, of the $I_{Kr}$ tail current density at 20 mV (FIG. 18A). Paired student's t-tests confirmed that the difference in normalized current density measured at baseline and in the presence of 11 and 56 µM of crizotinib reached the selected threshold for statistical significance (p≤0.05). The $IC_{50}$ was 8.9 µM with crizotinib alone (Table 10). When crizotinib was vortexed for 10 minutes at room temperature with liposomes at a ratio of 9:1 (e.g., 56 µM [25 µg/mL] crizotinib with 225 µg/mL liposomes), only the highest concentration of 56 µM crizotinib reached a statistically significant inhibition (59%). The $IC_{50}$ was 44 µM (Table 10). The liposomes alone did not have any effects on the $I_{Kr}$ tail current density (FIG. 18A).

Figure 19A:
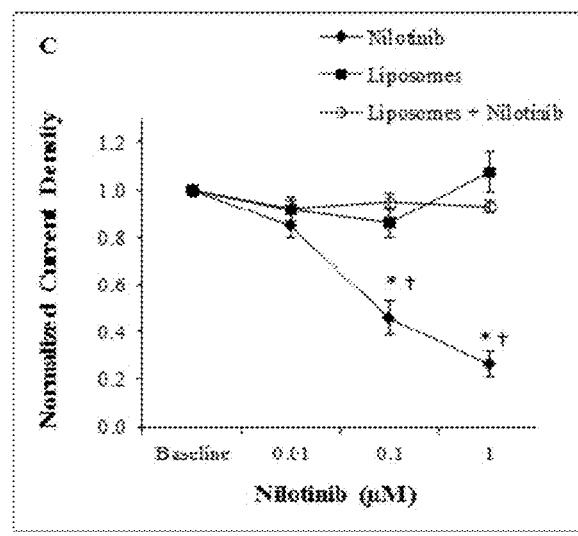
FIGS. 19A and 19B is a graph that shows the IKr tail current density averages and voltage dependency obtained by measuring the IKr tail peak amplitude and in the presence of nilotinib, liposomes alone, and nilotinib plus liposomes.

Nilotinib, at concentrations of 0.1 and 1 µM, caused statistically significant inhibition of the $I_{Kr}$ tail current density at 20 mV; 54 and 74%, respectively (FIG. 19A). The $IC_{50}$ was 0.08 µM with nilotinib alone (Table 10). When nilotinib was vortexed for 10 minutes at room temperature with liposomes at a ratio of 9:1 (e.g., 1 µM [0.5 µg/mL] nilotinib with 4.5 µg/mL liposomes), there were no effects of nilotinib on the $I_{Kr}$ channel, even at the highest concentrations of 1 µM. The $IC_{50}$ was >1 µM (Table 10). The liposomes alone did not have any effects on the $I_{Kr}$ tail current density (FIG. 19A).

Figure 18B:
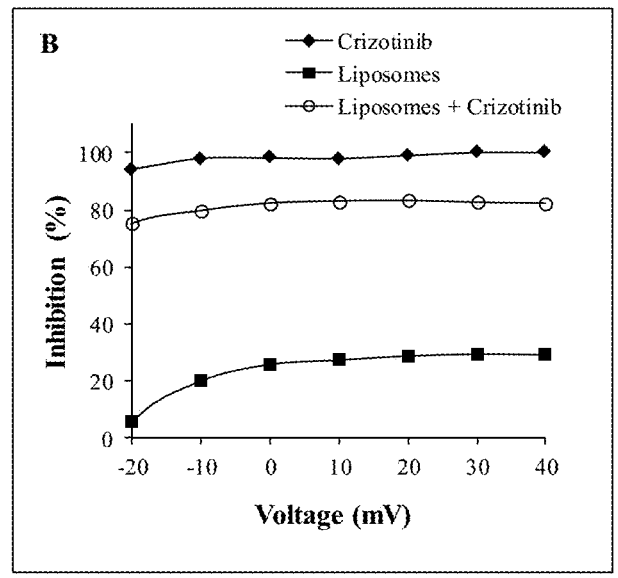
Figure 19B:
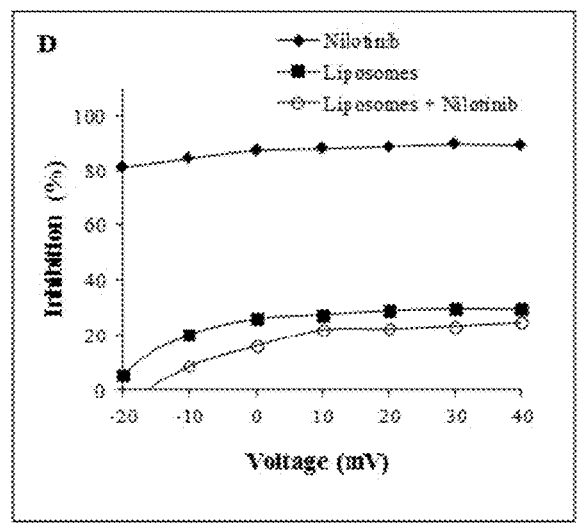

The current-voltage relationships of the rectifying inward current showed that the inhibitions observed on the tail current were not voltage dependent for both crizotinib and nilotinib (FIGS. 18B and 19B, respectively).

FIGS. 18A and 18B show $I_{Kr}$ tail current density averages and voltage dependency, respectively, obtained by measuring the $I_{Kr}$ tail peak amplitude at 20 mV in baseline conditions and in the presence of crizotinib, liposomes alone, and crizotinib plus liposomes. For crizotinib plus liposomes, the crizotinib was mixed with liposomes at 9:1 ratio and vortexed; e.g., 56 µM (25 µg/mL) crizotinib with 225 µg/mL liposomes. FIG. 18A is a graph that shows the current density measured from 3 to 4 cells, averaged, normalized against baseline current density, and corrected for time and solvent effects. The values plotted are the mean+standard error of the mean. Statistical comparisons between post-drug exposure and baseline current density levels were made using repeat paired Student's t-tests (*). Differences were considered significant when p≤0.05. FIG. 18B is a graph that shows the voltage dependency of the $I_{Kr}$ tail currents inhibition at the higher concentration of crizotinib tested (56 µM).

FIGS. 19A and 19B show $I_{Kr}$ tail current density averages and voltage dependency, respectively, obtained by measuring the $I_{Kr}$ tail peak amplitude at 20 mV in baseline conditions and in the presence of nilotinib, liposomes alone, and nilotinib plus liposomes. For nilotinib plus liposomes, the nilotinib was mixed with liposomes at 9:1 ratio and vortexed; e.g., 1 µM (0.5 µg/mL) nilotinib with 4.5 µg/mL liposomes. FIG. 19A is a graph of current density measured from 3 cells, averaged, normalized against baseline current density, and corrected for time and solvent effects. The values plotted are the mean±standard error of the mean. Statistical comparisons between post-drug exposure and baseline current density levels were made using repeat paired Student's t-tests (*). Differences were considered significant when p≤0.05. FIG. 19B is a graph that shows the voltage dependency of the $I_{Kr}$ tail currents inhibition at the higher concentration of nilotinib tested (1 µM).

TABLE 10

Concentrations that causes fifty percent inhibition ($IC_{50}$) of the $I_{Kr}$ current density in HEK 293 cells stably transfected with the hERG.

| Test Drug | Treatment | $I_{Kr}$ $IC_{50}$ (liposome concentration) |
|---|---|---|
| Crizotinib | Liposomes alone | >225 µg/mL |
|  | Crizotinib | 8.9 µM |
|  | Crizotinib plus liposomes | 44 µM (180 µg/mL) |
| Nilotinib | Liposomes alone | >4.5 µg/mL |
|  | Nilotinib | 0.08 µM |
|  | Nilotinib plus liposomes | >1 µM (>4.5 µg/mL) |

The positive control, E-4031, produced a statistically significant decreases in current density at a concentration of 100 nM. E-4031 was tested twice, with results of 67 and 79% inhibitions observed (data not shown). The results were within the range of internal validation data for this laboratory.

Reagents. Crizotinib and nilotinib were obtained from Reagents Direct. The positive control E-4031 (N-[4-[[1-[2-(6-methyl-2-pyridinyl)ethyl]-4-piperidinyl]carbon-yl]phenyl]methane sulfonamide dihydrochloride anhydrous) was obtained from Sigma-Aldrich. The empty liposomes were obtained from Polymun GmbH. The liposomes were made up of a 9.7:1 ratio of DMPC (1,2-dimyristoil-sn-glycero-3-phosphocholine) and DMPG (1,2-dimyristoyl-sn-glycero-3-phospho-rac-[1-glycerol]). For crizotinib or nilotinib plus liposomes, the crizotinib or nilotinib was mixed with liposomes at a 9:1 ratio and vortexed for 10 minutes at room temperature; e.g., 56 µM (25 µg/mL) crizotinib vortexed with 225 µg/mL liposomes. The internal pipette solution was composed of 140-mM KCl, 1.0-mM $MgCl_2$, 4.0-mM Mg-ATP, 5.0-mM EGTA, 10-mM HEPES, and 10-mM sucrose, pH 7.4±0.05. The hERG external solution was composed of 140.0-mM NaCl, 5.0-mM KCl, 1.8-mM $CaCl_2$, 1.0-mM MgCl2, 10.0-mM HEPES, and 10.0-mM dextrose, pH 7.3±0.05.

Cell Culture. HEK 293 cells stably transfected with the hERG were maintained in minimum essential medium complemented with 10% fetal bovine serum (Wisent Inc, St. Bruno, Quebec, Canada), 1% minimum essential medium sodium pyruvate, 1% nonessential amino acids, 1% L-glutamine, 1% penicillin/streptomycin, and 400 µg/mL G-418 (Geneticin) as the selection agent (all ingredients from Gibco/Invitrogen, Burlington, Ontario, Canada), and used between passages 12 and 16. Those cells from which a gigaohm (GD) seal could not be obtained or that did not generate currents with a distinctive tail current were eliminated during the equilibration period.

Procedure. The whole-cell patch-clamp technique was used to functionally evaluate drug interactions with the ionic channels. HEK 293 cells plated onto 35-mm petri dishes were washed twice with 1 mL of hERG external solution followed by the addition of 2 mL of hERG external solution. The petri dish was mounted on the stage of an inverted phase contrast microscope and maintained at constant temperature (35° C.±2° C.). A borosilicate glass micropipette filled with the internal pipette solution was positioned above a single cell using an Eppendorf PatchMan micromanipulator (Eppendorf Canada, Mississauga, Ontario, Canada). The micropipette was lowered to the cell until a close contact was achieved. The GD-range membrane-pipette seal was then created by applying a slight negative pressure (resistances were measured using a 5-mV square pulse). Cell capacitance was immediately measured to evaluate cell surface area, using a conversion factor of 1 pF/µm2. This cell surface area was later used to calculate net current density.

All currents were recorded following analog filtering using a 4-pole Bessel filter (Frequency Devices, Haverhill, Massachusetts) set at 1 kHz. Through the computer-controlled amplifier, the cell was depolarized to a maximum value of +40 mV (cultured cells), starting at −10 mV, in 10 mV increments, for 1 second. The membrane potential (mV) was then returned to −55 mV for 1 second, and finally repolarized to the resting potential value. This allowed the channels to go from activated to inactivated mode, and back to activated mode, to measure robust tail currents. All K+ selective currents passing through hERG channels were recorded using Axopatch-1D or Axopatch 200B amplifiers and digitized with Digidata 1322A or 1440A AD-DA interfaces (Axon instruments Inc, Foster City, Calif., now Molecular Devices Inc). The recording of the cell current started 500 ms before cell depolarization to −40 mV and lasted for 500 ms after the cell had been repolarized to −80 mV.

After baseline recordings were obtained, the increasing concentrations of the test agents crizotinib and nilotinib, alone or mixed with liposomes, were added in 20-4 aliquots directly to the experimental chamber and were allowed to disperse through a closed-circuit perfusion system using a mini-peristaltic pump (MP-1, Harvard Instruments, Holliston, Massachusetts). Exposure times for each concentration were limited to 5 minutes. Following the recording of currents in the presence of the highest concentrations of test agents a flow-through perfusion system was used to wash out the test article and obtain postexposure hERG currents in the same manner as previously described. Finally, three naïve cells were exposed to 100 nM of E-4031. The concentrations of E-4031 were added into the experimental chamber as was done with the test article.

The hERG currents generated by heterologous expression systems such as HEK 293 cells are known to run down over long periods of recording. Therefore, parallel experiments were run in the absence of the test agents and in the presence of the solvent to correct for the time-dependent decrease in current density, known as current rundown.

Statistical Analysis. The correction for the time-dependent decrease in current density involved averaging the changes in current density associated with time and solvents, and multiplying the "test-article" results with the resulting correction factor. All results were corrected for the effect of the vehicle and for time-dependent changes in current density.

hERG current amplitudes are expressed as current density (in anoamperes/picofarad [nA/pF]) to correct for variations in cell size within the population of cells used for this study. Currents were analyzed using the Clampfit 10.0 module of the pClamp 10.0 software (Axon Instruments Inc). The results obtained in the presence of each concentration were expressed as net current density, normalized against current density measured in baseline conditions.

The amplitude of the IKr tail current was calculated as the difference between the average current recorded before the depolarizing pulse to −40 mV and the maximum transient current recorded at the beginning of the repolarizing pulse to −55 mV. Paired t-tests were performed to determine the statistical significance of the differences in current density obtained before and after the exposure of the cells to the test article. Significance was set at P<0.05, where P is the probability that the difference in current density levels is due to chance alone.

EXAMPLE 3

In Vivo Evaluation of the Effects of Crizotinib and Liposomes Plus Crizotinib on Cardiac Electrophysiological Parameters of Rabbit Hearts In vivo evaluation of the effects of Crizotinib and Liposomes plus Crizotinib on cardiac electrophysiological parameters of rabbit hearts. The purpose of this study is to quantify the in vivo effects of Crizotinib and liposomes plus Crizotinib on cardiac electrophysiological (PR, QRS, RR, QT, and QTc intervals) parameters from rabbit hearts.

Adult male rabbits weighing between 3 kg and 4 kg. The Crizotinib was tested at 1, 2 and 3 mg/kg (loading doses) over a 10 minute infusion period at 0.057 mL/kg/min followed by a 15 minute maintenance infusion of 0.4, 0.8 and 1.2 mg/kg (maintenance doses) respectively at 0.037 mL/kg/min. The concentrations were selected based on information available at the time of the design of this study.

The liposomes were injected as an i.v bolus at the ratio of 9:1 of the total dose of crizotinib.

TABLE 11

| Dose tested | | |
|---|---|---|
| Crizotinib loading dose (mg/kg) | Crizotinib maintenance dose (mg/kg) | Liposomes dose (mg/kg) |
| 1 | 0.4 | 12.6 |
| 2 | 0.8 | 25.2 |
| 3 | 1.2 | 28.8 |

Anaesthetise rabbits instrumented with ECG leads. The rabbit was anaesthetized with a mixture of 2.5% isoflurane USP (Abbot Laboratories, Montreal Canada) in 95% $O_2$ and 5% $CO_2$. The left jugular vein was cannulated for the i.v infusion of the test article. ECG leads were placed on the animal. A continuous recording of the ECG was initiated and was stopped at the end of the infusion of the last concentration of test article.

Infusion of each loading dose (1, 2 and 3 mg/kg) lasted 10 minutes and was followed by a 15 minute infusion of the respective maintenance dose (0.4, 0.8 and 1.2 mg/kg). The infusion rate of the loading dose was 0.057 ml/kg/min and 0.037 mg/kg/min for the maintenance dose. Three rabbits were exposed to the crizotinib (n=3).

The liposomes were injected 5 minutes prior to start the infusion of each loading dose.

The liposomes were administered as an i.v bolus in the left ear vein at a ratio of 9:1. Three rabbits were exposed to the liposomes +crizotinib (n=3). Continuous recording of the entire experimental procedure. Significance test performed: Paired Student's t-test with threshold for significance set at p≤0.05. n=3.

Crizotinib. Crizotinib caused statistically significant dose dependent decreases of the heart rate (prolongation of the RR intervals). 2 and 3 mg/kg increased the RR intervals by 67 and 110 ms respectively. Crizotinib as of 2 mg/kg caused a statistically significant prolongation of the PR and QRS intervals. The PR interval was increased by 23 ms and the QRS interval by 13 ms following exposure to 3 mg/kg of crizotinib. Crizotinib caused statistically significant dose dependent prolongation of the QT interval.

When provided at 2 and 3 mg/kg caused a prolongation of the QT intervals of 34 and 48 ms respectively. Once corrected for change in heart rate using Van der Water correction factor, Crizotinib still caused a statistically significant prolongation of 38 ms of the QT intervals which could not be accounted for by a slower heart rate.

Liposomes plus Crizotinib. The liposomes plus Crizotinib (ratio 9:1) as of 2 mg/kg caused a statistically significant decrease of the heart rate (prolongation of the RR intervals). The RR intervals were increased by 61 and 90 ms following exposure to 2 and 3 mg/kg of Crizotinib respectively.

Liposomes plus Crizotinib caused a prolongation of the PR and QRS intervals. The effect of the liposomes+crizotinib on the PR and QRS intervals was statistically significant at the dose of 3 mg/kg only with a prolongation of 15 ms of the PR interval and 7 ms of the QRS interval.

Liposomes plus Crizotinib at 3 mg/kg caused a prolongation of the QT intervals of 24 ms. However; this effect on the QT intervals was not statistically significant when compared to the QT interval measured in baseline conditions. Once corrected for changes in heart rate using Van der Water correction factor, 3 mg/kg caused a prolongation of 15 ms of QT intervals which was still not statistically significant.

This study aimed at evaluating the effects of Crizotinib and liposomes plus Crizotinib on the cardiac electrophysiological parameters of rabbit hearts in vivo. It was found that the Crizotinib alone caused a dose-dependent prolongation RR, PR, QRS and QT intervals of the rabbit hearts in vivo. The effect of crizotinib on the RR and QT intervals was statistically significant as of 1 mg/kg and as of 2 mg/kg on the PR and QRS intervals.

The liposomes plus Crizotinib caused a prolongation RR, PR and QRS intervals of the rabbit hearts in vivo. The effect of liposomes plus Crizotinib on the RR interval was statistically significant as of 2 mg/kg while it was statistically significant on the PR and QRS intervals at 3 mg/kg only. The liposomes plus crizotinib did not cause any statistically significant prolongation of the QT intervals of the rabbit hearts in vivo.

The following table summarizes the index of protection afforded by the presence of liposomes.

TABLE 12

Comparison of the maximal in vivo effect on the electrophysiological parameters of the hearts caused by 3 mg/kg of Crizotinib vs 3 mg/kg of Crizotinib precede by i.v. injection of the liposomes.

| | Liposomes + Crizotinib | Crizotinib | Protection factor |
|---|---|---|---|
| RR interval prolongation (ms) | 110 | 91 | 1.2 |
| PR interval prolongation (ms) | 23 | 15 | 1.5 |
| QRS interval prolongation (ms) | 13 | 7 | 1.9 |
| QTc interval prolongation (ms) | 38 | 16 | 2.4 |

TABLE 13

In vivo effect of Crizotinib on RR interval (ms) of rabbit heart.

| Condition | RR Intervals (ms) | SEM | p values | n = |
|---|---|---|---|---|
| Baseline | 257 | 22.79 | n/a | 3 |
| Crizotinib, 1 mg/kg | 294* | 27.28 | 0.040 | 3 |
| Crizotinib, 2 mg/kg | 324* | 26.12 | 0.004 | 3 |
| Crizotinib, 3 mg/kg | 367* | 34.77 | 0.013 | 3 |

*Mean that the value obtained after exposure to the test article concentration was statistically different from the value in baseline condition. Difference was considered statistically significant when $p \leq 0.05$.

TABLE 14

In vivo effect of Liposomes plus Crizotinib on RR interval (ms) of rabbit heart.

| Condition | RR Intervals (ms) | SEM | p values | n = |
|---|---|---|---|---|
| Baseline (Liposome) | 226 | 12.48 | n/a | 3 |
| Liposome + Crizotinib, 1 mg/kg | 247 | 12.12 | 0.083 | 3 |
| Liposome + Crizotinib, 2 mg/kg | 287* | 13.53 | 0.003 | 3 |
| Liposome + Crizotinib, 3 mg/kg | 317* | 13.97 | 0.000 | 3 |

Figure 20:
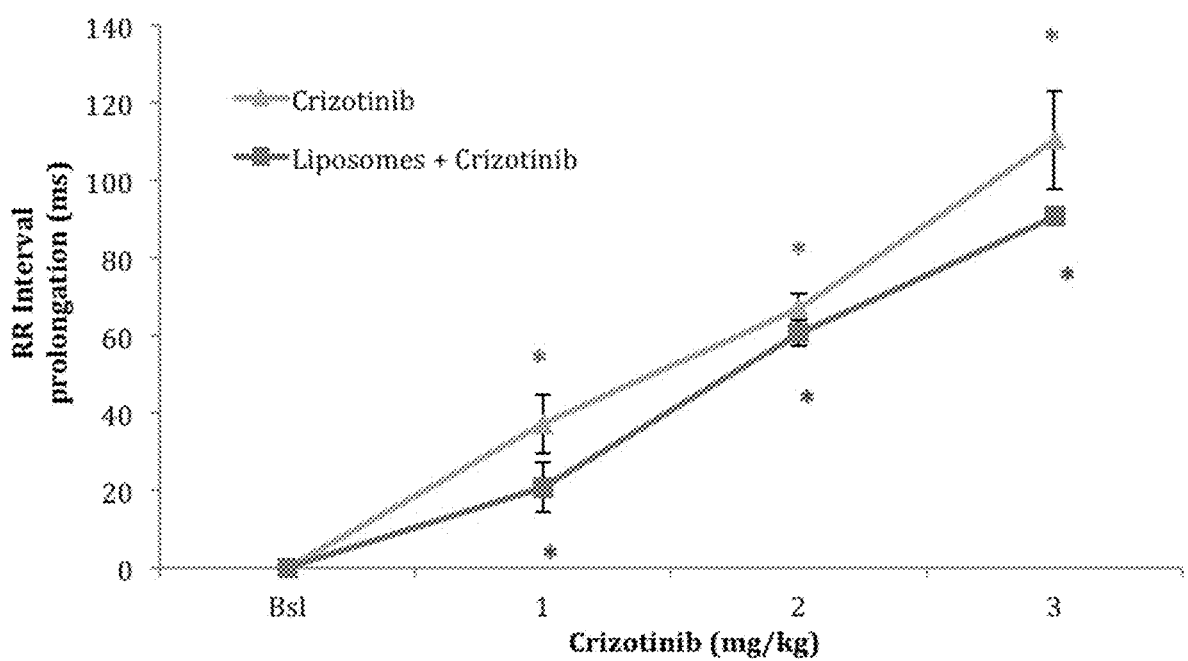
FIG. 20 is a graph that shows the in vivo effect of Crizotinib and Liposomes+Crizotinib on RR interval (ms) of rabbit heart.

FIG. 20: In vivo effect of Crizotinib and Liposomes+Crizotinib on RR interval (ms) of rabbit heart.

TABLE 15

In vivo effect of Crizotinib on PR interval (ms) of rabbit heart.

| Condition | PR Intervals (ms) | SEM | p values | n = |
|---|---|---|---|---|
| Baseline | 78 | 3.71 | n/a | 3 |
| Crizotinib, 1 mg/kg | 81 | 4.14 | 0.280 | 3 |
| Crizotinib, 2 mg/kg | 92* | 4.35 | 0.004 | 3 |
| Crizotinib, 3 mg/kg | 101* | 8.49 | 0.048 | 3 |

TABLE 16

In vivo effect of Liposomes plus Crizotinib on PR interval (ms) of rabbit heart.

| Condition | PR Intervals (ms) | SEM | p values | n = |
|---|---|---|---|---|
| Baseline (Liposome) | 65 | 2.31 | n/a | 3 |
| Liposome + Crizotinib, 1 mg/kg | 70 | 3.67 | 0.096 | 3 |
| Liposome + Crizotinib, 2 mg/kg | 75 | 2.82 | 0.140 | 3 |
| Liposome + Crizotinib, 3 mg/kg | 80* | 3.01 | 0.011 | 3 |

Figure 21:
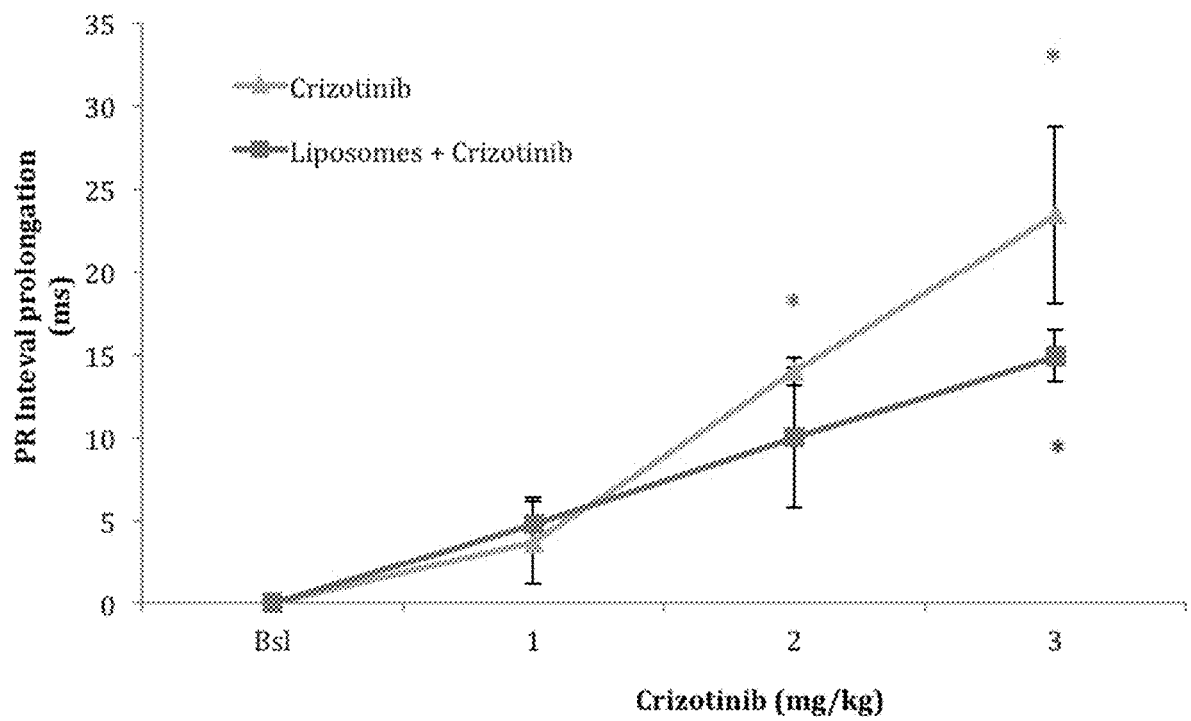
FIG. 21 is a graph that shows the in vivo effect of Crizotinib and Liposomes+Crizotinib on PR interval (ms) of rabbit heart.

FIG. 21: In vivo effect of Crizotinib and Liposomes plus Crizotinib on PR interval (ms) of rabbit heart.

TABLE 17

In vivo effect of Crizotinib on QRS intervals (ms) of rabbit heart.

| Condition | QRS Intervals (ms) | SEM | p values | n = |
|---|---|---|---|---|
| Baseline | 43 | 4.56 | n/a | 3 |
| Crizotinib, 1 mg/kg | 48 | 5.68 | 0.178 | 3 |
| Crizotinib, 2 mg/kg | 53* | 3.44 | 0.033 | 3 |
| Crizotinib, 3 mg/kg | 56* | 3.85 | 0.006 | 3 |

TABLE 18

In vivo effect of Liposomes plus Crizotinib on QRS intervals (ms) of rabbit heart.

| Condition | QRS Intervals (ms) | SEM | p values | n = |
|---|---|---|---|---|
| Baseline (Liposome) | 44 | 2.03 | n/a | 3 |
| Liposome + Crizotinib, 1 mg/kg | 43 | 2.36 | 0.438 | 3 |
| Liposome + Crizotinib, 2 mg/kg | 45 | 3.07 | 0.578 | 3 |
| Liposome + Crizotinib, 3 mg/kg | 51* | 2.91 | 0.039 | 3 |

Figure 22:
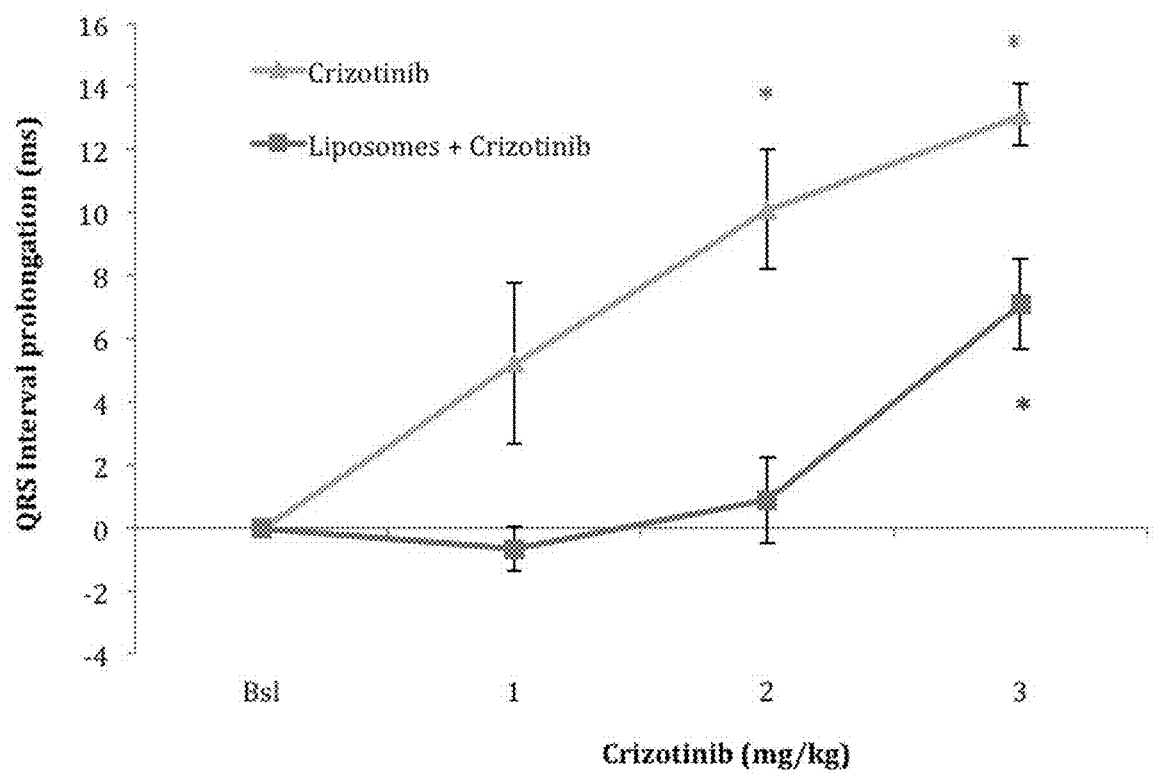
FIG. 22 is a graph that shows the in vivo effect of Crizotinib and Liposomes+Crizotinib on QRS interval (ms) of rabbit heart.

FIG. 22: In vivo effect of Crizotinib and Liposomes plus Crizotinib on QRS interval (ms) of rabbit heart.

TABLE 19

In vivo effect of Crizotinib on QT interval (ms) of rabbit heart.

| Condition | QT Intervals (ms) | SEM | p values | n = |
|---|---|---|---|---|
| Baseline | 171 | 13.75 | n/a | 3 |
| Crizotinib, 1 mg/kg | 189* | 12.88 | 0.012 | 3 |
| Crizotinib, 2 mg/kg | 205* | 12.87 | 0.016 | 3 |
| Crizotinib, 3 mg/kg | 218* | 13.06 | 0.000 | 3 |

TABLE 20

In vivo effect of Liposomes plus Crizotinib on QT interval (ms) of rabbit heart.

| Condition | QT Intervals (ms) | SEM | p values | n = |
|---|---|---|---|---|
| Baseline (Liposome) | 175 | 8.92 | n/a | 3 |
| Liposome + Crizotinib, 1 mg/kg | 181 | 8.57 | 0.415 | 3 |
| Liposome + Crizotinib, 2 mg/kg | 190 | 5.10 | 0.175 | 3 |
| Liposome + Crizotinib, 3 mg/kg | 199 | 4.30 | 0.074 | 3 |

Figure 23:
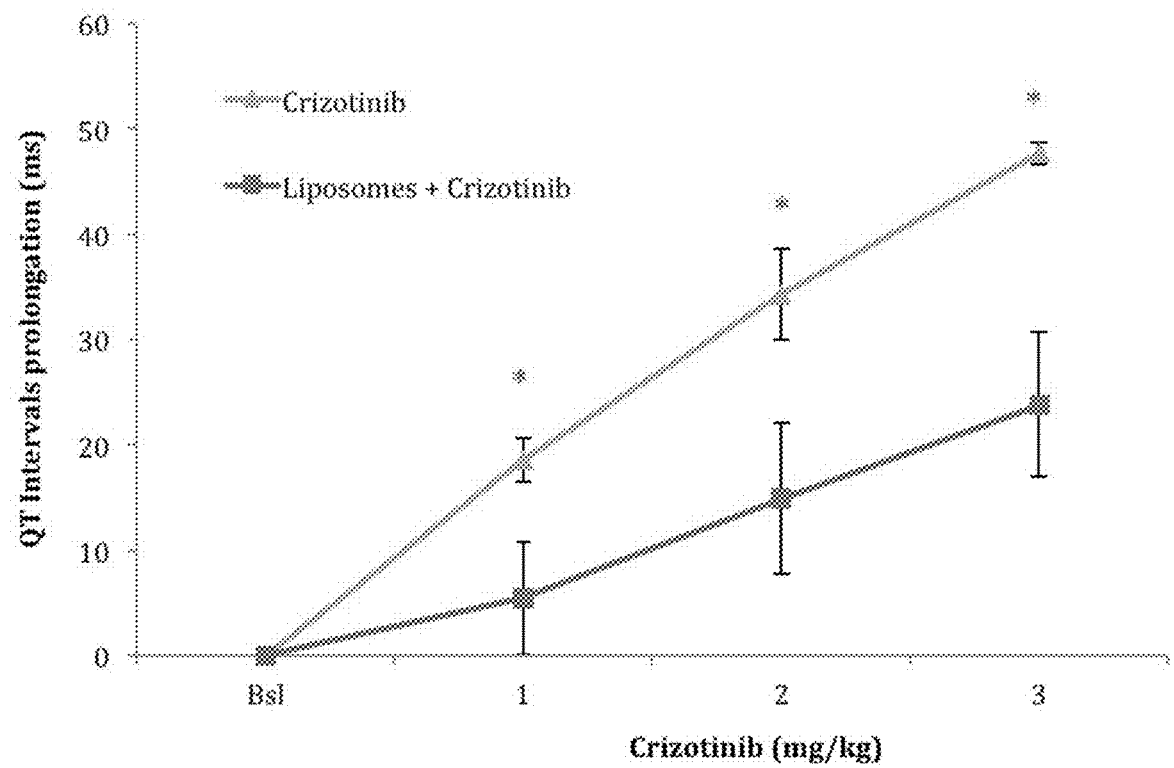
FIG. 23 is a graph that shows the in vivo effect of Crizotinib and Liposomes+Crizotinib on QT interval (ms) of rabbit heart.

FIG. 23: In vivo effect of Crizotinib and Liposomes plus Crizotinib on QT interval (ms) of rabbit heart.

TABLE 21

In vivo effect of Crizotinib on QTc Van der Water interval of rabbit heart.

| Condition | QTc interval (ms) | SEM | p values | n = |
|---|---|---|---|---|
| Baseline | 235 | 11.77 | n/a | 3 |
| Crizotinib, 1 mg/kg | 251* | 10.55 | 0.013 | 3 |
| Crizotinib, 2 mg/kg | 264* | 10.93 | 0.026 | 3 |
| Crizotinib, 3 mg/kg | 273* | 10.18 | 0.003 | 3 |

TABLE 22

In vivo effect of Liposomes + Crizotinib on QTc Van der Water interval of rabbit heart.

| Condition | QTc interval (ms) | SEM | p values | n = |
|---|---|---|---|---|
| Baseline | 243 | 7.84 | n/a | 3 |
| Liposome + Crizotinib, 1 mg/kg | 246 | 7.53 | 0.526 | 3 |
| Liposome + Crizotinib, 2 mg/kg | 252 | 4.30 | 0.309 | 3 |
| Liposome + Crizotinib, 3 mg/kg | 259 | 3.58 | 0.150 | 3 |

Figure 24:
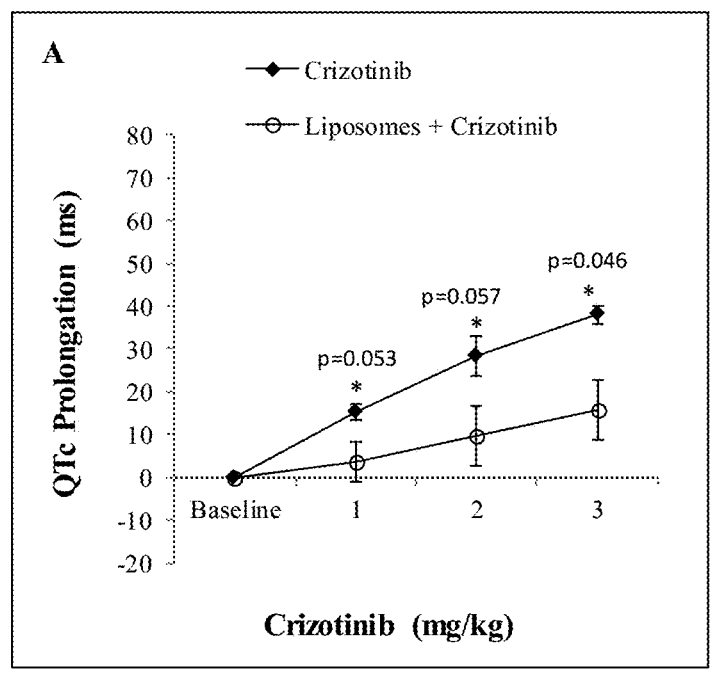
FIG. 24 is a graph that shows the in vivo effect of Crizotinib and Liposomes+Crizotinib on QTc Van der Water intervals of rabbit heart.

FIG. 24: In vivo effect of Crizotinib and Liposomes plus Crizotinib on QTc Van der Water intervals of rabbit heart.

EXAMPLE 4

In Vivo Evaluation of the In Vivo Effects of Nilotinib and Liposomes Plus Nilotinib on Cardiac Electrophysiological Parameters of Rabbit Hearts In vivo evaluation of the In vivo effects of Nilotinib and Liposomes+Nilotinib on cardiac electrophysiological parameters of rabbit hearts. The purpose of this study is to quantify the in vivo effects of Nilotinib and liposomes+Nilotinib on cardiac electrophysiological (PR, QRS, RR, QT, and QTc intervals) parameters from rabbit hearts.

Test System. Adult male rabbits weighing between 3 kg and 4 kg.

Doses tested. The Nilotinib was tested at 2, 4 and 5.5 mg/kg (loading doses) over a 10 minute infusion period at 0.057 mL/kg/min followed by a 15 minute maintenance infusion of 0.14, 0.28 and 0.39 mg/kg (maintenance doses) respectively at 0.037 mL/kg/min. The concentrations were selected based on information available at the time of the design of this study. The liposomes were injected as an i.v bolus at the ratio of 9:1 of the total dose of Nilotinib.

Test performed. Anaesthetise rabbits instrumented with ECG leads. Procedure. In vivo rabbit. The rabbits were anaesthetized with a mixture of 2.5% isoflurane USP (Abbot Laboratories, Montreal Canada) in 95% $O_2$ and 5% $CO_2$. The left jugular vein was cannulated for IV infusion of the test agent. ECG leads were placed on the animal, and the ECG signals were filtered at 500 Hz using an Iso-DAM8A (from Word Precision Instrument, Sarasota, Fla., USA) and digitized at a sampling rate of 2.0 kHz using a Digidata 1322A interface (from Axon Instruments Inc., Foster City, Calif., USA, [now Molecular Devices Inc.]). Continuous recording of the ECG was initiated 5 minutes before beginning infusion of the first dose of the compound and was terminated at the end of infusion of the last dose. Following baseline ECG recording, the infusion of the first loading dose of the compound was started. At the end of the first loading dose, the infusion was switch to the first maintenance dose. The rabbit was exposed to each dose for 25 minutes (10 minutes of loading dose followed by 15 minutes of maintenance dose). The same procedure was applied until the rabbit was exposed to all of the selected doses of test agent or vehicle equivalent. The liposomes were injected 5 minutes prior to the start of infusion of each loading dose. The liposomes were administrated as an IV bolus in the left ear vein at a ratio of 9:1 (µg/mL basis). ECG parameters were analyzed and presented in the same manner as for the in vitro heart experiment.

TABLE 23

| Dose tested | | |
|---|---|---|
| Nilotinib loading dose (mg/kg) | Nilotinib maintenance dose (mg/kg) | Liposomes dose (mg/kg) |
| 2 | 0.14 | 25.6 |
| 4 | 0.28 | 51.1 |
| 5.5 | 0.39 | 70.7 |

Data analysis and acquisition. Continuous recording of the entire experimental procedure. Statistical analysis. A paired one-way t-test was performed to determine the statistical significance of the differences in baseline values compared to each treatment. An unpaired one-way t-test, assuming unequal variances, was done to compare crizotinib or nilotinib alone with crizotinib or nilotinib plus liposomes. Significance test performed: Paired Student's t-test with threshold for significance set at p≤0.05. n=3.

Nilotinib caused dose dependent decreases of the heart rate (prolongation of the RR intervals). 5.5 mg/kg of Nilotinib caused a statistically significant prolongation of the RR intervals of 78 ms.

Liposomes plus Nilotinib at concentration up to 5.5 mg/kg did not cause any statistically significant effect on the PR intervals.

As of 2 mg/kg Nilotinib caused a statistically significant prolongation of the QRS intervals. 5.5 mg/kg of Nilotinib caused a prolongation of the QRS intervals of 7 ms.

Nilotinib caused statistically significant dose dependent prolongation of the QT interval. 4 and 5.5 mg/kg caused a prolongation of the QT intervals of 41 and 66 ms respectively. Once corrected for change in heart rate using Van der Water correction factor, Nilotinib still caused a statistically significant prolongation of the QT intervals which could not be accounted for by a slower heart rate.

Liposomes plus Nilotinib. The liposomes plus Nilotinib (ratio 9:1) at 5.5 mg/kg caused a statistically significant decrease of the heart rate (prolongation of the RR intervals). The RR intervals were increased by 69 ms following exposure to 5.5 mg/kg of Nilotinib.

Liposomes plus Nilotinib at concentration up to 5.5 mg/kg did not cause any statistically significant effect on the PR, QRS and QT intervals.

This study evaluated the effects of Nilotinib and Liposomes plus Nilotinib on the cardiac electrophysiological parameters of rabbit hearts in vivo.

It was found that the Nilotinib alone caused a dose-dependent prolongation RR, QRS and QT intervals of the rabbit hearts in vivo. The effect of Nilotinib on the RR intervals was statistically significant at 5.5 mg/kg only while it was statistically significant the QRS and QT intervals as of 2 mg/kg.

The Liposomes plus Nilotinib caused a prolongation RR interval of the rabbit hearts in vivo. The effect of liposomes plus Nilotinib on the RR interval was statistically significant at 5.5 mg/k. The liposomes plus Nilotinib did not cause any statistically significant prolongation of the PR, QRS and QT intervals of the rabbit hearts in vivo.

The following table summarizes the index of protection afforded by the presence of liposomes.

TABLE 24

Comparison of the maximal in vivo effect on the electrophysiological parameters of the hearts caused by 4 mg/kg of Nilotinib vs 4 mg/kg of Nilotinib preceded by i.v. injection of the liposomes.

|  | Nilotinib | Liposomes plus Nilotinib | Protection factor |
|---|---|---|---|
| RR interval prolongation (ms) | 54 | 37 | 1.5 |
| QRS interval prolongation (ms) | 6 | 3 | 2 |
| QTc interval prolongation (ms) | 36 | 8 | 4.5 |

TABLE 25

In vivo effect of Nilotinib on RR interval (ms) of rabbit heart.

| Condition | RR Intervals (ms) | SEM | p values | n = |
|---|---|---|---|---|
| Baseline | 253 | 15.10 | n/a | 3 |
| Nilotinib, 2 mg/kg | 273 | 4.68 | 0.265 | 3 |
| Nilotinib, 4 mg/kg | 307 | 9.31 | 0.132 | 3 |
| Nilotinib, 5.5 mg/kg | 331* | 2.70 | 0.047 | 3 |

*Mean that the value obtained after exposure to the test article concentration was statistically different from the value in baseline condition. Difference was considered statistically significant when $p \leq 0.05$.

TABLE 26

In vivo effect of Liposomes plus Nilotinib on RR interval (ms) of rabbit heart.

| Condition | RR Intervals (ms) | SEM | p values | n = |
|---|---|---|---|---|
| Baseline (Liposome) | 213 | 12.00 | n/a | 3 |
| Liposome plus Nilotinib, 2 mg/kg | 217 | 5.89 | 0.590 | 3 |
| Liposome plus Nilotinib, 4 mg/kg | 250 | 14.66 | 0.068 | 3 |
| Liposome plus Nilotinib, 5.5 mg/kg | 282* | 21.52 | 0.041 | 3 |

Figure 25:
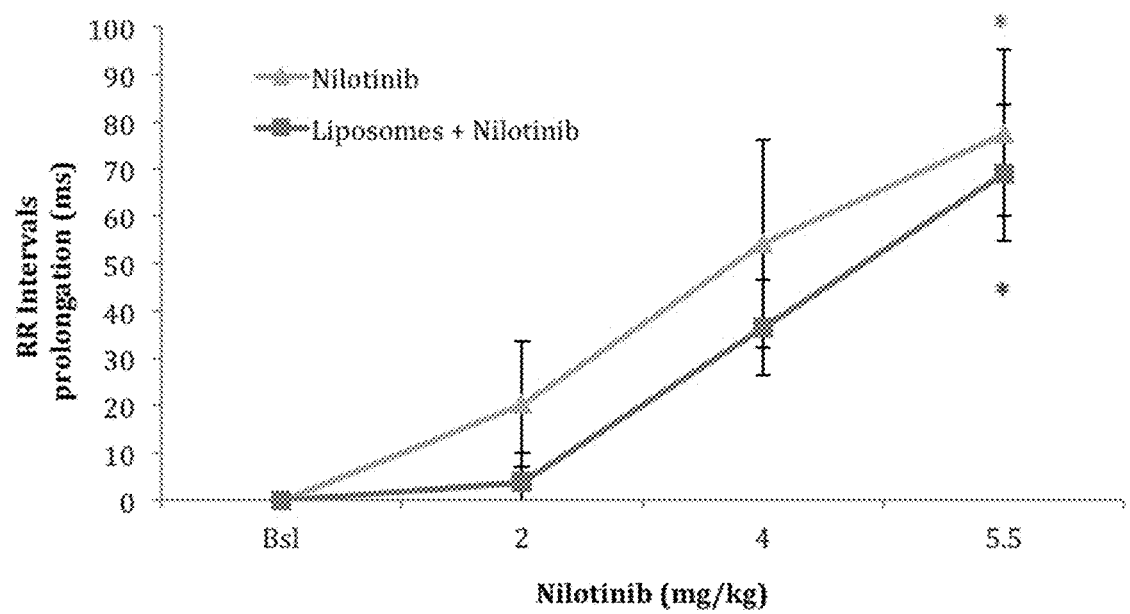
FIG. 25 is a graph that shows the in vivo effect of Nilotinib and Liposomes plus Nilotinib on RR interval (ms) of rabbit heart.

FIG. 25 is a graph that shows the in vivo effect of Nilotinib and Liposomes plus Nilotinib on RR interval (ms) of rabbit heart.

TABLE 27

In vivo effect of Nilotinib on PR interval (ms) of rabbit heart.

| Condition | PR Intervals (ms) | SEM | p values | n = |
|---|---|---|---|---|
| Baseline | 79 | 7.85 | n/a | 3 |
| Nilotinib, 2 mg/kg | 78 | 5.74 | 0.632 | 3 |
| Nilotinib, 4 mg/kg | 80 | 5.00 | 0.947 | 3 |
| Nilotinib, 5.5 mg/kg | 82 | 6.84 | 0.159 | 3 |

TABLE 28

In vivo effect of Liposomes plus Nilotinib on PR interval (ms) of rabbit heart.

| Condition | PR Intervals (ms) | SEM | p values | n = |
|---|---|---|---|---|
| Baseline (Liposome) | 65 | 2.22 | n/a | 3 |
| Liposome plus Nilotinib, 2 mg/kg | 65 | 0.91 | 0.890 | 3 |
| Liposome plus Nilotinib, 4 mg/kg | 68 | 1.15 | 0.076 | 3 |
| Liposome plus Nilotinib, 5.5 mg/kg | 71 | 1.42 | 0.055 | 3 |

Figure 26:
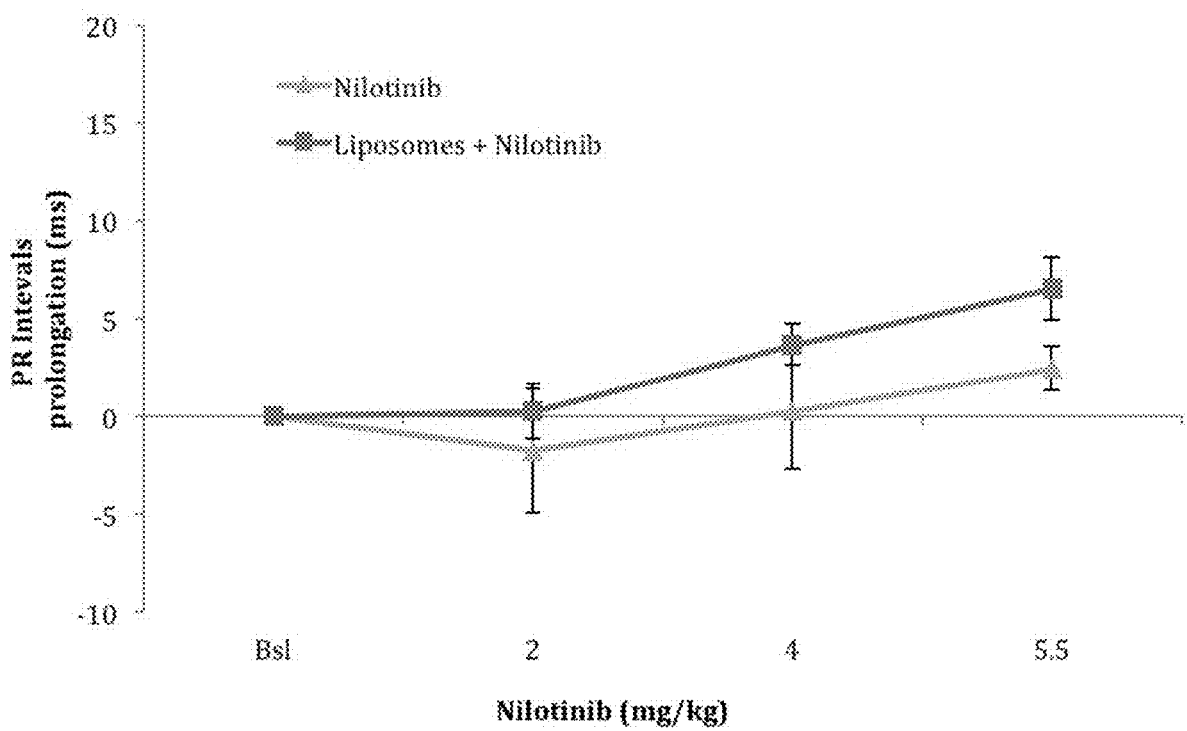
FIG. 26 is a graph that shows the in vivo effect of Nilotinib and Liposomes plus Nilotinib on PR interval (ms) of rabbit heart.

FIG. 26 is a graph that shows the in vivo effect of Nilotinib and Liposomes plus Nilotinib on PR interval (ms) of rabbit heart.

TABLE 29

In vivo effect of Nilotinib on QRS intervals (ms) of rabbit heart.

| Condition | QRS Intervals (ms) | SEM | p values | n = |
|---|---|---|---|---|
| Baseline | 40 | 5.96 | n/a | 3 |
| Nilotinib, 2 mg/kg | 44* | 6.66 | 0.046 | 3 |
| Nilotinib, 4 mg/kg | 46* | 6.23 | 0.014 | 3 |
| Nilotinib, 5.5 mg/kg | 47* | 6.07 | 0.000 | 3 |

TABLE 30

In vivo effect of Liposomes plus Nilotinib on QRS intervals (ms) of rabbit heart.

| Condition | QRS Intervals (ms) | SEM | p values | n = |
|---|---|---|---|---|
| Baseline (Liposome) | 36 | 1.35 | n/a | 3 |
| Liposome plus Nilotinib, 2 mg/kg | 37 | 1.74 | 0.069 | 3 |
| Liposome plus Nilotinib, 4 mg/kg | 39 | 2.14 | 0.086 | 3 |
| Liposome plus Nilotinib, 5.5 mg/kg | 40 | 2.01 | 0.069 | 3 |

Figure 27:
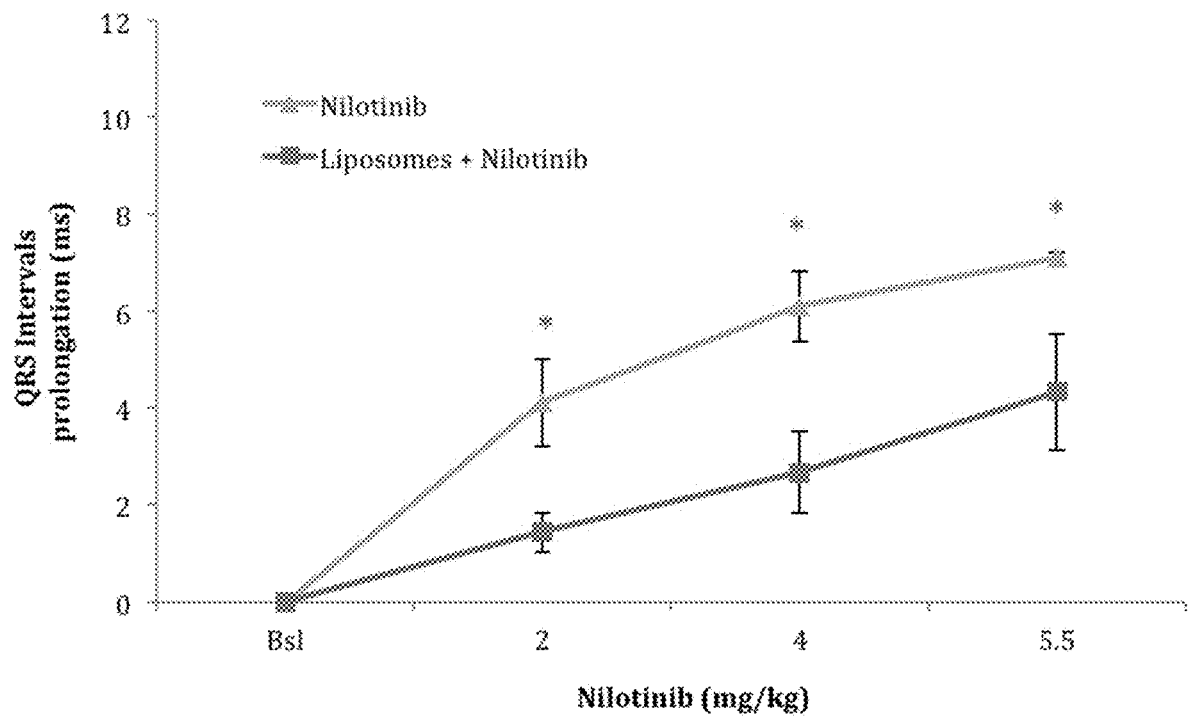
FIG. 27 is a graph that shows the in vivo effect of Nilotinib and Liposomes plus Nilotinib on QRS interval (ms) of rabbit heart.

FIG. 27 is a graph that shows the in vivo effect of Nilotinib and Liposomes plus Nilotinib on QRS interval (ms) of rabbit heart.

TABLE 31

In vivo effect of Nilotinib on QT interval (ms) of rabbit heart.

| Condition | QT Intervals (ms) | SEM | p values | n = |
|---|---|---|---|---|
| Baseline | 161 | 2.26 | n/a | 3 |
| Nilotinib, 2 mg/kg | 182* | 4.14 | 0.042 | 3 |
| Nilotinib, 4 mg/kg | 201* | 5.17 | 0.025 | 3 |
| Nilotinib, 5.5 mg/kg | 227* | 12.37 | 0.040 | 3 |

TABLE 32

In vivo effect of Liposomes plus Nilotinib on QT interval (ms) of rabbit heart.

| Condition | QT Intervals (ms) | SEM | p values | n = |
|---|---|---|---|---|
| Baseline (Liposome) | 153 | 6.73 | n/a | 3 |
| Liposome plus Nilotinib, 2 mg/kg | 148 | 1.53 | 0.473 | 3 |

TABLE 32-continued

In vivo effect of Liposomes plus Nilotinib
on QT interval (ms) of rabbit heart.

| Condition | QT Intervals (ms) | SEM | p values | n = |
|---|---|---|---|---|
| Liposome plus Nilotinib, 4 mg/kg | 164 | 9.17 | 0.429 | 3 |
| Liposome plus Nilotinib, 5.5 mg/kg | 185 | 9.83 | 0.089 | 3 |

Figure 28:
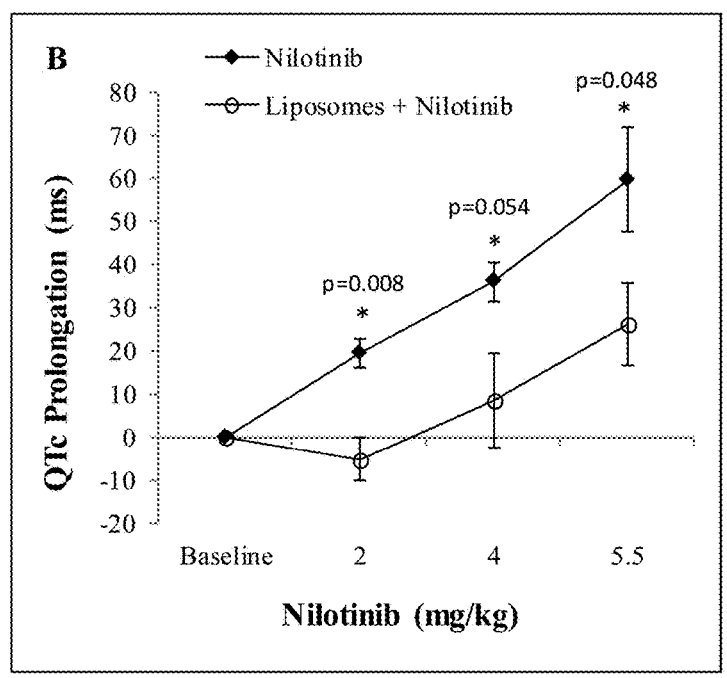
FIG. 28 is a graph that shows the in vivo effect of Nilotinib and Liposomes plus Nilotinib on QT interval (ms) of rabbit heart.

FIG. 28 is a graph that shows the in vivo effect of Nilotinib and Liposomes plus Nilotinib on QT interval (ms) of rabbit heart.

TABLE 33

In vivo effect of Nilotinib on QTc Van
der Water interval of rabbit heart.

| Condition | QTc Intervals (ms) | SEM | p values | n = |
|---|---|---|---|---|
| Baseline | 226 | 1.27 | n/a | 3 |
| Nilotinib, 2 mg/kg | 245* | 3.91 | 0.029 | 3 |
| Nilotinib, 4 mg/kg | 262* | 4.42 | 0.016 | 3 |
| Nilotinib, 5.5 mg/kg | 285* | 12.14 | 0.039 | 3 |

TABLE 34

In vivo effect of Liposomes plus Nilotinib on
QTc Van der Water interval of rabbit heart.

| Condition | QTc Intervals (ms) | SEM | p values | n = |
|---|---|---|---|---|
| Baseline (Liposome) | 221 | 5.73 | n/a | 3 |
| Liposome plus Nilotinib, 2 mg/kg | 216 | 1.25 | 0.409 | 3 |
| Liposome plus Nilotinib, 4 mg/kg | 230 | 8.71 | 0.531 | 3 |
| Liposome plus Nilotinib, 5.5 mg/kg | 247 | 8.69 | 0.113 | 3 |

Figure 29:
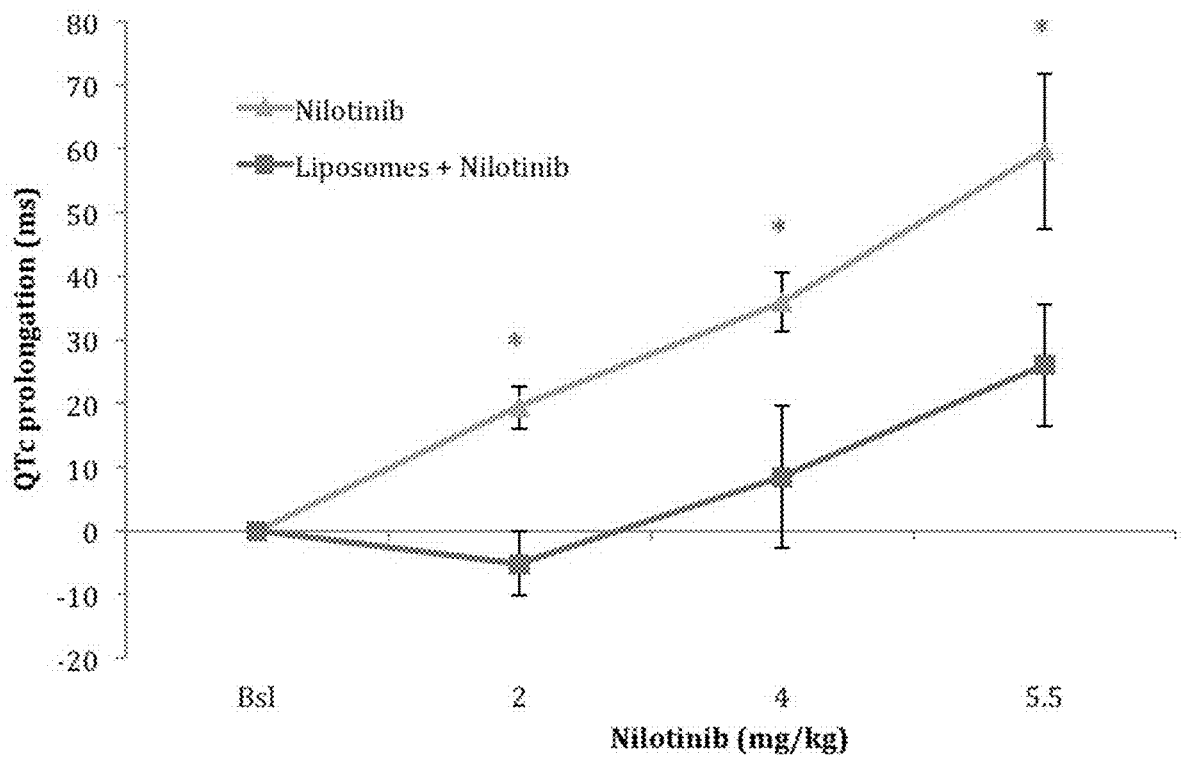
FIG. 29 is a graph that shows the in vivo effect of Nilotinib and Liposomes plus Nilotinib on QTc Van der Water intervals of rabbit heart.

FIG. 29 is a graph that shows the in vivo effect of Nilotinib and Liposomes plus Nilotinib on QTc Van der Water intervals of rabbit heart.

Tables 35 and 36 summarize the results above, and provide further information about the effects of the present invention.

TABLE 35

Concentrations that caused fifty percent inhibition of the $I_{Kr}$ current
density in HEK 293 cells stably transfected with the hERG.

| Treatment | Drug | |
|---|---|---|
| | Crizotinib | Nilotinib |
| Liposomes alone | >225 µg/mL[a] | >4.5 µg/mL[a] |
| Drug alone | 8.9 µM | 0.08 µM |
| Drug plus Liposomes | 44 µM | >1 µM |

The concentrations that caused fifty percent inhibition of the $I_{Kr}$ current density (IC$_{50}$) were calculated from the data presented in FIGS. 18A-B and 19A-B.
[a]225 and 4.5 µg/mL were the highest concentrations of liposomes alone tested in the assay, for crizotinib and nilotinib, respectively.

TABLE 36

Effects of crizotinib and nilotinib, alone and with liposomes,
on left ventricular pressure, in in vitro rabbit hearts.

| | Concentration of Drug (µM) | Liposomes alone | Drug alone | Liposomes plus Drug |
|---|---|---|---|---|
| Crizotinib | 11 | 1.25 (2.10) | −7.34 (6.19) | −1.03 (0.62) |
| | 56 | 0.67 (1.87) | −8.22 (6.23) | −1.15 (0.37) |
| Nilotinib | 14 | −0.98 (1.56) | −0.45 (1.51) | −0.32 (0.93) |
| | 28 | 0.47 (2.01) | −9.80 (0.19) | −3.30 (0.34) |

Values are the change from baseline (mmHg).
Values are the mean (SEM), of 3 hearts per group.

In Vitro $I_{Kr}$ Current.

It was found that Crizotinib, at concentrations of 11 and 56 µM, caused 57 and 89% inhibition, respectively, of the $I_{Kr}$ tail current density at 20 mV (FIG. 18A). Paired student's t-tests showed that the difference in normalized current density measured at baseline and in the presence of 11 and 56 µM of crizotinib reached the selected threshold for statistical significance (p 0.05). The IC$_{50}$ was 8.9 µM with crizotinib alone (Table 35). When crizotinib was mixed with liposomes at a ratio of 9:1, only the highest concentration of 56 µM crizotinib reached a statistically significant inhibition compared to baseline (59%). The IC$_{50}$ was 44 µM. Liposomes plus crizotinib at 11 µM did not have any effects on the $I_{Kr}$ tail current density. Liposomes plus crizotinib at 56 µM did have a significant effect on the $I_{Kr}$ tail current density when compared to baseline. However, when comparing the current density between crizotinib at 11 and 56 µM, and liposomes plus crizotinib, there was a significant inhibition of the effects of crizotinib when mixed with liposomes. The liposomes alone did not have any effects on the $I_{Kr}$ tail current density (FIG. 18A).

Nilotinib, at concentrations of 0.1 and 1 µM, caused statistically significant inhibition of the $I_{Kr}$ tail current density at 20 mV, when compared to baseline; 54 and 74%, respectively (FIG. 19A). The IC$_{50}$ was 0.08 µM with nilotinib alone (Table 35). When nilotinib was vortexed for 10 minutes at room temperature with liposomes at a ratio of 9:1, there were no effects of nilotinib on the $I_{Kr}$ channel, even at the highest concentrations of 1 µM. The IC$_{50}$ was >1 µM. When comparing the current density between nilotinib, and liposomes plus nilotinib, there was a significant inhibition of the effects of 0.1 and 1 µM nilotinib when mixed with liposomes. The liposomes alone did not have any effects on the $I_{Kr}$ tail current density (FIG. 19A).

The current-voltage relationships of the rectifying inward current showed that the inhibitions observed on the tail current were not voltage dependent for both crizotinib and nilotinib (FIGS. 18B and 19B, respectively).

The positive control, E-4031, produced a statistically significant decreases in current density at a concentration of 100 nM. E-4031 was tested twice, with results of 67 and 79% inhibitions observed (data not shown).

In Vitro Rabbit Heart QTc Intervals.

Figure 30A:
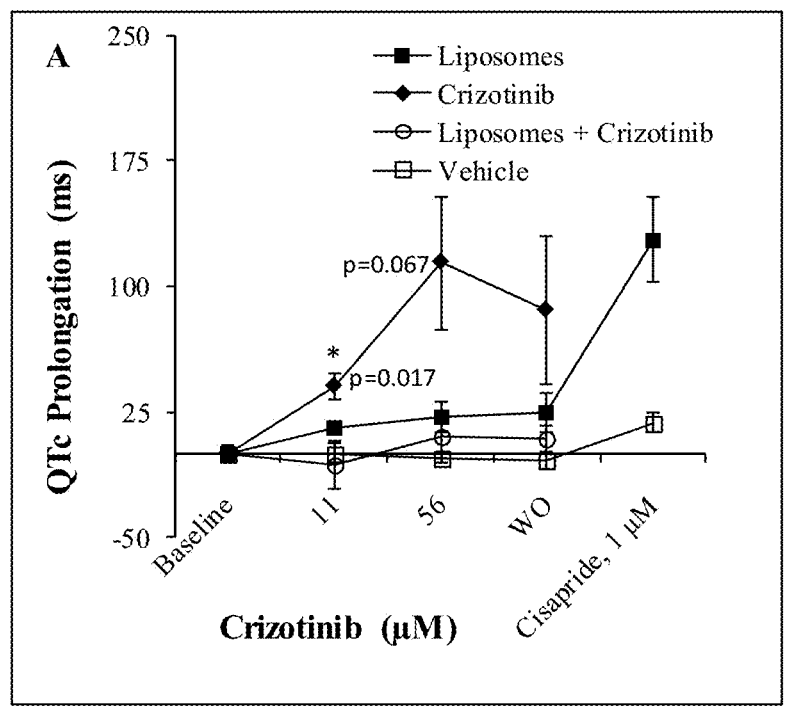
FIGS. 30A and 30B are graphs that show QTc prolongation in rabbits treated with crizotinib, nilotinib, crizotinib plus liposomes, and nilotinib plus liposomes. Animals were given an IV loading dose over a 10 minute period, followed by a maintenance dose over a 15 minute period. Liposomes were dosed IV 5 minutes before the loading dose of the drugs. The loading and maintenance doses for crizotinib were 1, 2 and 3 mg/kg, and 0.4, 0.8 and 1.2 mg/kg, respectively (FIG. 30A). The doses for nilotinib were 2, 4 and 5.5 mg/kg, and 0.14, 0.28 and 0.39 mg/kg, respectively (FIG. 30B). The doses of liposomes were 9-fold higher than the doses of drug, on a mg/kg basis. The values plotted are the mean+standard error of the mean, for 3 rabbits per group. Statistical comparisons were done as described in FIGS. 23 and 28.
Figure 30B:
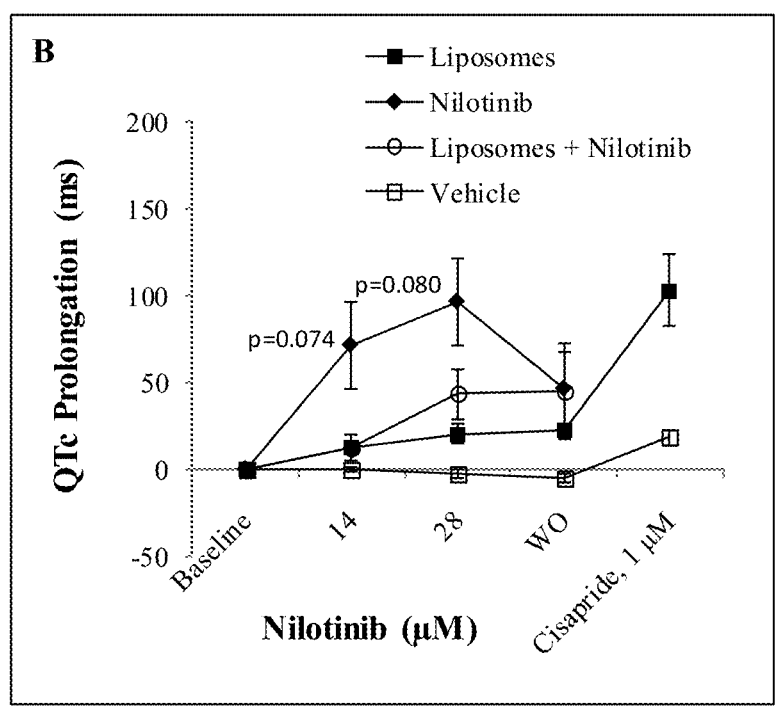

Crizotinib, at concentrations of 11 and 56 µM, caused a dose dependent prolongation of the QTc interval (FIG. 30A). Mixing crizotinib with liposomes at a ratio of 9:1, resulted in a significant inhibition of the crizotinib-induced QTc prolongation. Nilotinib, at concentrations of 14 and 28 µM, also caused a dose dependent prolongation of the QTc interval (FIG. 30B). As with crizotinib, mixing nilotinib with liposomes, resulted in a significant inhibition of the nilotinib-induced QTc prolongation. The cisapride positive control showed the expected prolongation of the QTc interval.

The effects of crizotinib and nilotinib on ECGs were associated with effects on LVP (Table 36). When hearts were exposed to crizotinib or nilotinib alone, there was a decrease in LVP. When liposomes were mixed with crizotinib or nilotinib, the effects on LVP were reversed.

Rabbit QTc Intervals after In Vivo Dosing.

Rabbits given crizotinib at 1, 2 and 3 mg/kg by IV infusions over 10 minutes, followed by a maintenance dose for 15 minutes, showed a dose-dependent prolongation of the QTc interval (FIG. 23). Injecting liposomes 5 minutes prior to treatment with crizotinib resulted in a significant inhibition of the crizotinib-induced QTc prolongation. Rabbits given nilotinib at 2, 4 and 5.5 lmg/kg by IV infusions over 10 minutes, followed by a maintenance dose for 15 minutes, showed a dose-dependent prolongation of the QTc interval (FIG. 28). As with crizotinib, injecting liposomes 5 minutes prior to treatment with nilotinib, resulted in a significant inhibition of the nilotinib-induced QTc prolongation.

These data demonstrated that liposomes protect against the inhibitory effect of these kinase-inhibitor drugs on the $I_{Kr}$ channel using stably hERG transfected HEK 293 cells, and ameliorate cardiac QTc prolongation resulting from both in vitro and in vivo exposure. These results demonstrate that mixing of these drugs with liposomes prevents interactions of these inhibitory drugs with the $I_{Kr}$ channel allowing more normal gating kinetics to occur, and decreasing the degree and incidence of QTc prolongation that may occur in the clinic.

Other tyrosine kinase inhibitors have also been shown to have effects on the QTc interval, including lapatinib, sunitinib and vandetanib (Shah et al., 2013). The most studied in vitro is lapatinib (Lee et al., 2010). Lapatinib was shown to prolong action potential duration of isolated rabbit Purkinje fibers at 5 µM. This was associated with an inhibitory effect on the $I_{Ke}$ channel with an $IC_{50}$ of 0.8 µM, and a slight effect on the $I_{Ks}$ amplitude at 5 µM. No effects were observed on the $I_{Na}$, $I_{K1}$ or $I_{Ca}$ channels.

In the clinic, crizotinib is given at doses as high as 500 mg/day (250 mg twice a day [BID]), which is about 4.2 mg/kg or 156 mg/m$^2$, BID. From the FDA's review of the new drug application for crizotinib, steady state $C_{max}$ in cancer patients given 500 mg BID averaged 650 ng/mL, or 1.5 µM (Xalkori, 2011b). Mossé et al. (2013) reported steady state $C_{max}$ in children with cancer to be 630 ng/mL (1.4 µM) after dosing 280 mg/m$^2$ BID. This is well within the range of effects on the in vitro $I_{Kr}$ channel with an $IC_{50}$ of 8.9 µM reported in the represent study, and 1.1 µM reported during the development of crizotinib (Xalkori, 2011 a). Nilotinib is dosed as high as 600 mg/day (300 mg BID), which is about 5 mg/kg or 188 mg/m$^2$, BID. Cancer patients given 400 mg BID had steady state $C_{max}$ of 1754 ng/mL, or 3.3 µM (Kim et al., 2011). Chinese patients given 400 mg BID had steady state $C_{max}$ 2161 ng/mL, or 4.1 µM (Zhou et al., 2009). The present study showed an $IC_{50}$ in the $I_{Kr}$ assay of 0.08 µM, and 0.13 µM was reported during the development of nilotinib (Tasigna®, 2007a).

It has previously been reported that liposomes mitigate inhibitory effects of curcumin on the $I_{Kr}$ channel (Helson et al., 2012). Curcumin alone inhibited the $I_{Kr}$ channel with an $IC_{50}$ of 4.9 µM, with the highest concentration tested (11.4 µM) resulting in 80% inhibition. When mixed with the same liposomes, and same ratio, as in the present study, the highest dose of curcumin tested (11.4 µM) only reached 45% inhibition. Curcumin that was encapsulated in the liposomes, and not just mixed, also resulted in inhibition of curcumin-induced $I_{Kr}$ inhibition; 25% inhibition at the high concentration of 11.4 µM. In this study, when the positive control E-4031 was tested alone, the $IC_{50}$ was 56 nM. When E-4031 was mixed with liposomes, the $IC_{50}$ increased to 210 nM.

Tartar emetic is a trivalent antimonial drug that causes QT interval elongation in rats and humans. When tartar emetic was encapsulated in liposomes, the QT effects were abolished (Maciel et al., 2010). One important difference between the tartar emetic study and the present study is the composition of the liposomes that were used. The liposomes used in the tartar emetic study were composed of L-a-distearoylphosphatidylcholine, cholesterol and polyethylene glycol 2000 distearoylphosphatidyl-ethyanolamine. Another difference is the present study showed that simply mixing the drugs with the liposomes, or injecting them prior to treatment with QT-prolonging drugs, and not encapsulating them, resulted in the inhibitory effects.

One clinical trial in healthy volunteers has shown that encapsulation with liposomes abolished QT-prolongation effects. When bupivacaine, which increases QT interval in humans and laboratory animals, is encapsulated in liposomes (Exparel®), it did not cause QT prolongation at doses as high as 750 mg given subcutaneously (Naseem et al., 2012). As with the tartar emetic study, here the drug was encapsulated and the components of the liposome were different than the in the present study: cholesterol, 1,2-dipalmitoyl-sn-glycero-3 phospho-rac-(1-glycerol), tricaprylin, and 1,2-dierucoylphosphatidylcholine.

The in vitro assay assessing the effects of drugs on the $I_{Kr}$ (hERG) current is used extensively to help predict potential effects of a drug on QTc interval in the clinic (Witchel, 2001). This has been a useful assay, but sometime results in false positives. The present study demonstrates an example where this in vitro assay was very predictive of in vivo QTc prolongation in both animals and humans.

Surprisingly, based upon the data in the present study, and the data with curcumin (Helson et al., 2012), it does not appear necessary to encapsulate a drug in the DMPC/DMPG liposome to mitigate $I_{Kr}$ suppression by crizotinib and nilotinib, and possibly other QTc-prolonging agents. A simple mixing of the compound with the liposomes may be sufficient. The present invention demonstrates that for orally administered QT-prolonging agents, a concurrent subcutaneous administration of an extended release formulation of liposomes may suffice. Using the methods and techniques demonstrated herein it is possible to study QT-prolonging drugs in in vivo animal models of QTc prolongation.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least +1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES—EXAMPLE 1

U.S. Patent Application Publication No. 2010/0004549: System and Method of Serial Comparison for Detection of Long QT Syndrome (LQTS).

U.S. Patent Application Publication No. 2008/0255464: System and Method for Diagnosing and Treating Long QT Syndrome.

U.S. Patent Application Publication No. 2007/0048284: Cardiac Arrhythmia Treatment Methods.

U.S. Patent Application Publication No. 2001/00120890: Ion Channel Modulating Activity I.

Anderson CL, Delisle B P, Anson B D, et al.: Most LQT2 Mutations Reduce Kv11.1 (hERG) Current by a Class 2 (Trafficking Deficient) Mechanism. Circulation 2006 113: 365-373.

Compton S J, Lux R L, Ramsey M R, et al.: Genetically defined therapy of inherited long QT syndrome. Correction of abnormal repolarization by potassium. 1996 94:1018-1022.

Djeddi D, Kongolo G, Lefaix C, Mounard J, Leke A: Effect of domperidone on QT interval in neonates. J Pediatrics 2008 153(5): 596-598.

Ducroq J., Printemps R, Le Grand M.: Additive effects ziprasidone and D, L-sotalol on the action potential in rabbit purkinje fibers and on the hERG potassium current. J.Pharmacol. Toxicol Methods 2005 52:115-122.

Etheridge S P, Compton S J, Tristani-Firouzi M, Mason J W: A new oral therapy for long QT syndrome: long term oral potassium improves repolarization in patients with hERG mutations. JAM Coll Cardiol 2003 42:1777-1782.

Fauchier L, Babuty D Poret P, Autret M L, Cosnay P, Fauchier J P: Effect of Verapamil on QT interval dynamicity. AM J Cardiol. 1999 83(5):807-808 A10-1.

Fowler N O, McCall D, Chou T C, Hilmes J C, Hanenson I B,: Electrocardiographic changes and cardiac arrhythmias in patients receiving psychotropic drugs. Am J Cardiol 1976 37(2): 223-230.

Jervell A, Lang-Nielson F: Congenital deaf-mutism, functional heart disease with prolongation of the QT interval and sudden death. Am Heart J. 1957 54: 59-68.

Kang J, Chen X L, Wang H, et al.: Discovery of a small molecule activator of the human ether-a-go-go-related gene (HERG) cardiac K+ channel. Mol Pharmacol 2005 67: 827-836.

Katchman A N, Koerner J, Tosaka T, Woosley R L, Eberty S N: Comparative evaluation of HERG currents and QWT intervals following challenge with suspected torsadogenic and non-torsdogenic drugs. J Pharmacol Exp Ther. 2006 316(3):1098-1106.

Layton D, Key C, Shakir S A: Prolongation of the QT interval and cardiac arrhythmias associated with cisapride: limitations of the pharmacoepidemiological studies conducted and proposals for the future. Pharmacoepidemiol Drug Saf. 2003 12(1):31-40.

Maciel N R, Reis P G, Kato K C et al: Reduced cardio-vascular alterations of tarter emetic administered in long-circulating liposomes in rats. Toxicology Letters. 2010 199 (3): 234-238.

Mehta R T, Hopfer R L, Gunner L A, Juliano R L, Lopez-Berestein G: Formulation, toxicity ,and antifungal activity in vitro of liposomal-encapsulated nystatin as therapeutic agent for systemic candidiasis. Antimicrob Agents Chemother. 1987 31(12):1897-1900.

Moha ou Maati H, Ducroq J, Rivet J Faivre J. F. Le Grande M, Bois P: Curcumin blocks the recombinant human cardiac KCNQ1/KCNE1 channels (IKs) stably expressed in HEK 293 cells. Congress de Physiologie,de Pharmacologie et de Therapeutique, Clermont-Ferrand, France, 9-11 Avril. 2008 Fund. Clin. Pharmacol. 22(Supp1.1).

Shimizu W Antzelevitch C: Sodium channel block with mexiletine is effective in reducing dispersion of repolarization and preventing torsade de pointes in LQT2 and LQT3 models of the long QT syndrome. 1997 Circulation 96: 2038-2047.

Shimizu W Antzelevitch C: Effects of a K(+) channel opener to reduce transmural dispersion of repolarization and prevent torsade de pointes LQT1, LQT2, and LQT3 models of the long QT syndrome. Circulation, 2000 102: 702-712.

Stansfeld P J, Gedeck P, Gosling M, Cox B, Mitcheson J S, Sutclif M J: Drug block of the hERG potassium Channel: insight from modeling. Proteins 2007 68(2): 568-580.

Quan X Q, Bai R, Liu N, Chen B D, Zhang C T. Increasing gap junction coupling reduces transmural dispersion of repolarization and prevents torsades de points in rabbit LQT3 model. J Cardiovasc Electrophysiol 2007 18:1184-1189.

Zavhariae U, Giordanetto F, Leach A G: Side chain flexabilities in the human ether-a-go-go related potassium channel (hERG) together with matched-pair binding studies suggest a new binding mode for channel blockers. J Med Chem 2009 52(14): 4266-4276.

Zhou Z, Gong Q, January C T: Correction of defective protein trafficking of a mutant HERG potassium channel in human long QT syndrome: Pharmacological and temperature effects. J Biol Chem.1999 274: 31123-31126.

REFERENCES—EXAMPLE 2

1. Yap Y G, Camm A J. Drug induced QT prolongation and torsades de pointes. Heart. 2003; 89:1363-1372.

2. FDA Pharmacology Review of Xalkori® (crizotinib), IND No. 202570, 2011a, www.accessdata.fda.gov/drugsatfda_docs/nda/2011/202570Orig1s000PharmR.pdf (accessed Oct. 9, 2013).

3. FDA Clinical Pharmacology and Biopharmaceutics Review of Xalkori® (crizotinib), IND No. 202570, 2011b, www.accessdata.fda.gov/drugsatfda_docs/nda/2011/202570Orig1s000ClinPharmR.pdf (accessed Oct. 9, 2013).

4. Xalkori (2013) [package insert], Pfizer Laboratories, New York, N.Y., revised February 2013.

5. FDA Pharmacology Review of Tasigna® (nilotinib), IND No. 22-068, 2007a, www.accessdata.fda.gov/drugsatfda_docs/nda/2007/022068s000_PharmR_P1.pdf and www.accessdata.fda.gov/drugsatfda_docs/nda/2007/022068s000_MedR_P2.pdf, (accessed Oct. 25, 2013).

6. FDA Clinical Pharmacology and Biopharmaceutics Review of Tasigna® (nilotinib), IND No. 22-068, 2007b, www.accessdata.fda.gov/drugsatfda_docs/nda/2007/022068s000_ClinPharmR.pdf, (accessed Oct. 24, 2013).

7. Tasigna (2013), Package insert, Novartis Pharmaceuticals, East Hanover, N.J., revised September 2013.

8. Doherty K R, Wappel R L, Talbert D R, Trusk P B, Moran D M, Kramer J W, Brown A M, Shell S A, Bacus S. Multi-parameter in vitro toxicity testing of crizotinib, sunitinib, erlotinib, and nilotinib in human cardiomyocytes. Toxicol Appl Pharmacol. 2013; 272(1):245-55.

9. Helson L, Shopp G, Bouchard A, Majeed M. Liposome mitigation of curcumin inhibition of cardiac potassium delayed-rectifier current. J Recep Lig Channel Res. 2012; 5:1-8.

10. Maciel N R, Reis P G, Kato K C, et al. Reduced cardio-vascular alterations of tarter emetic administered in long-circulating liposomes in rats. Toxicol Lett. 2010; 199 (3): 234-238.

11. Naseem A, Harada T, Wang D, Arezina R, Lorch U, Onel E, Camm A J, Taubel J. Bupivacaine extended release liposome injection does not prolong QTc interval in a thorough QT/QTc study in healthy volunteers. J Clin Pharmacol. 2012; 52(9):1441-7.

ADDITIONAL REFERENCES

Crouch, M. A., Limon, L., and Cassano, A. T. (2003). Clinical relevance and management of drugs-related QT interval prolongation. Pharmacotherapy. 23(7):881-908.

Kim, K. P., Ryu, M. H., Yoo, C., et al. (2011). Nilotinib in patients with GIST who failed imatinib and sunitnib: importance of prior surgery on drug availability. Cancer Chemother. Pharmacol. 68(2):285-291.

Lee, H. A., Kim, E. J., Hyun, S. A., Park, S. G., and Kim, K. S. (2010). Electrophysiological effects of the anti-cancer drug lapatinib on cardiac repolarization. Basic Clin. Pharmacol. Toxicol. 107(1):614-618.

Mossé, Y. P., Lim, M. S., Voss, S. D., et al. (2013). Safety and activity of crizotinib for pediatric patients with refractory solid tumors or anaplastic large-cell lymphoma: a Children's Oncology Group phase 1 consortium study. Lancet Oncol. 14(16): 472-480.

Shah, R. R., Morganroth, J., and Shah, D. R. (2013). Cardiovascular safety of tyrosine kinase inhibitors: with a special focus on cardiac repolarization (QT interval). Drug Saf. 36(5)295-316.

Tasigna®. (2007a). FDA Pharmacology Review of Tasigna® (nilotinib), IND No. 22-068, http://www.accessdata.fda.gov/drugsatfda_docs/nda/2007/022068s000_PharmR_P1.pdf and http://www.accessdata.fda.gov/drugsatfda_docs/nda/2007/ 022068s000_MedR_P2.pdf, (accessed Oct. 25, 2013).

Tasigna. (2007b). FDA Clinical Pharmacology and Biopharmaceutics Review of Tasigna (nilotinib), IND No. 22-068, http://www.accessdata.fda.gov/drugsatfda_docs/nda/2007/022068s000_ClinPharmR.pdf, (accessed Oct. 24, 2013).

Van de Water, A., Verheyen, J., Xhonneux, R., and Reneman, R. S. (1989). An improved method to correct the QT interval of the electrocardiogram for changes in heart rate. J. Pharmacol. Methods, 22, 207-217.

Witchel, H. J. (2011). Drug-induced hERG block and QT syndrome. *Cardiovasc Ther.* 29(4):251-259.

Xalkori®, (2011a). FDA Pharmacology Review of Xalkori® (crizotinib), IND No. 202570, www.accessdata.fda.gov/drugsatfda_docs/nda/2011/202570Orig1s000PharmR.pdf (accessed Oct. 9, 2013).

Xalkori. (2011b). FDA Clinical Pharmacology and Biopharmaceutics Review of Xalkori (crizotinib), IND No. 202570, www.accessdata.fda.gov/drugsatfda_docs/nda/2011/202570Orig1s000ClinPharmR.pdf (accessed Oct. 9, 2013).

Zhou, L., Meng, F., Yin, O., et al. (2009). Nilotinib for imatinib-resistant or -intolerant chronic myeloid leukemia in chronic phase, accelerated phase, or blast crisis: a single- and multiple-dose, open-label pharmacokinetic study in Chinese patients. Clin. Ther. 31(7):1568-1575.

What is claimed is:

1. A composition for treating or preventing one or more cardiac channelopathies or conditions resulting from irregularities or alterations in cardiac patterns, or both, in a human or animal subject consisting of:
    one or more pharmacologically active agents provided in an amount that inhibits the activity of an ether-a-go-go-related gene (hERG), wherein the one or more pharmacologically active agents are kinase inhibitors selected from crizotinib and nilotinib, wherein the amount of the one or more pharmacologically active agents is sufficient to treat a cancer, wherein the cancer is selected from non-small cell lung cancer or chronic myeloid leukemia;
    one or more empty liposomes, wherein the empty liposomes are administered prior to, concomitantly, or after administration of the pharmacologically active agent, wherein the one or more empty liposomes are provided in an amount effective to reduce the cardiac channelopathies or conditions resulting from irregularities or alterations in cardiac patterns, and the empty liposomes consist of at least one liposome selected from at least one of phosphatidylserine, phosphatidylinositol, sphingomyelin, cardiolipin, phosphatidic acid, cerebrosides, dicetylphosphate, dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, diacylglycerol, diacylglycerol-succinate, DMPC (1,2-dimyristoyl-sn-glycero-3-phosphocholine), or DMPG (1,2-dimyristoyl-sn-glycero-3-phospho-rac-[1-glycerol]).

2. The composition of claim 1, wherein the composition is used for the treatment or prevention of non-cardiac diseases of hERG.

3. The composition of claim 1, wherein the composition is adapted for enteral, parenteral, intravenous, intraperitoneal, or oral administration.

4. The composition of claim 1, wherein the active agent and the one or more empty liposomes may be bound or conjugated together.

5. The composition of claim 1, wherein the one or more empty liposomes consist essentially of anionic, cationic, or neutral lipids.

6. The composition of claim 1, wherein the composition further comprises a pharmaceutically acceptable dispersion medium, solvent, or vehicle, wherein the active agent, the one or more empty liposomes or both are dissolved, dispersed, or suspended in the medium, the solvent, or the vehicle.

7. A composition for preventing or treating one or more adverse reactions arising from administration of a therapeutically active agent or a drug in a human that inhibits the activity of an ether-a-go-go-related gene (hERG) consisting of:
    one or more pharmacologically active agents provided in an amount that causes at least one of IKr channel inhibition or QT prolongation and one or more empty liposomes, wherein the one or more pharmacologically active agents are kinase inhibitors selected from crizotinib and nilotinib, wherein the amount of the one or more pharmacologically active agents is sufficient to treat a cancer, wherein the cancer is selected from non-small cell lung cancer or chronic myeloid leukemia; and one or more empty liposomes are administered prior to, concomitantly, or after administration of the therapeutically active agent or the drug in an amount effective to reduce the adverse reactions arising from administration of the therapeutically active agent or drug, and the one or more empty liposomes consist essentially of one or more lipids selected from phosphatidylserine, phosphatidylinositol, sphingomyelin, cardiolipin, phosphatidic acid, cerebrosides, dicetylphosphate, dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, diacylglycerol, diacylglycerol-succinate, DMPC (1,2-dimyristoyl-sn-glycero-3-phosphocholine), or DMPG (1,2-dimyristoyl-sn-glycero-3-phospho-rac-[1-glycerol]).

8. The composition of claim 7, wherein the therapeutically active agent or a drug is used in a prevention or a treatment of one or more cardiac or non-cardiac diseases in the human or animal subject.

9. The composition of claim 7, wherein the composition is used for the treatment or prevention of non-cardiac related diseases of hERG.

10. The composition of claim 7, wherein the composition is adapted for enteral, parenteral, intravenous, intraperitoneal, or oral administration.

11. The composition of claim 7, wherein the active agent and the one or more empty liposomes may be bound or conjugated together.

12. The composition of claim 7, wherein the one or more empty liposomes consist essentially of anionic, cationic, or neutral lipids.

13. The composition of claim 7, wherein the one or more empty liposomes comprise DMPC (1,2-dimyristoyl-sn-glycero-3-phosphocholine) and DMPG (1,2-dimyristoyl-sn-glycero-3-phospho-rac-[1-glycerol]).

* * * * *